(12) United States Patent
Donald et al.

(10) Patent No.: US 7,671,181 B2
(45) Date of Patent: Mar. 2, 2010

(54) POLYNUCLEOTIDES ENCODING COCCIDIAN PARASITE CASEIN KINASE I, A CHEMOTHERAPEUTIC TARGET FOR ANTIPROTOZOAL AGENTS

(75) Inventors: Robert G. K. Donald, South Orange, NJ (US); Paul Liberator, Holmdel, NJ (US); Xiaotian Zhong, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 638 days.

(21) Appl. No.: 10/586,374

(22) PCT Filed: Jan. 12, 2005

(86) PCT No.: PCT/US2005/000955

§ 371 (c)(1),
(2), (4) Date: Jul. 14, 2006

(87) PCT Pub. No.: WO2005/070180

PCT Pub. Date: Aug. 4, 2005

(65) Prior Publication Data

US 2008/0280313 A1 Nov. 13, 2008

Related U.S. Application Data

(60) Provisional application No. 60/537,094, filed on Jan. 16, 2004.

(51) Int. Cl.
*C07H 21/04* (2006.01)
*C12N 15/63* (2006.01)
*C12N 1/20* (2006.01)
*C12P 21/00* (2006.01)

(52) U.S. Cl. .................. 536/23.1; 536/23.2; 435/320.1; 435/252.3; 435/71.1

(58) Field of Classification Search ........................ None
See application file for complete search history.

(56) References Cited

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Guo et al, Protein tolerance to random amino acid change. Proc Natl Acad Sci U S A. Jun. 22, 2004;101(25):9205-9210. Epub Jun. 14, 2004.*
McDonagh et al., Production of caseinophosphopeptides (CPPs) from sodium caseinate using a range of commercial protease preparations. International Dairy Journal (1998), 8(1), 39-45.*
Donald, Robert, G.K., et al., Molecular & Biochemical Parasitology, "Characterization of two *T. gondii* CK1 isoforms", vol. 141, pp. 15-27, 2005.
Knockaert, M., et al., Chemistry & Biology, "Intracellular targets of cyclin-dependent kinase inhibitors: idenitification by affinity chromatography using immobilised inhibitors", vol. 7, pp. 411-422, 2000.
NCBI Sequence, Nucleotide Database, GenBank Accession No. BM175598, 2001.
NCBI Sequence, Nucleotide Database, GenBank Accession No. T62400, 1995.
NCBI Sequence, Protein Database, GenBank Accession No. AAS46019, 2004.
NCBI Sequence, Protein Database, GenBank Accession No. AAS46020, 2004.
NCBI Sequence, Protein Database, GenBank Accession No. AAS46021, 2004.
Allen, P.C., et al., Clinical Microbiology Reviews, "Recent advances in biology and immunobiology of *Eimeria* species and in diagnosis and control of infection with these coccidian parasites of poultry", vol. 15, No. 1, pp. 58-65, 2002.
Barik, Sailen, et al., The Journal of Biological Chemistry, "Identification, cloning, and mutational analysis of the casein kinase 1 cDNA of the malaria parasite, *Plasmodium falciparum*", vol. 272, No. 42, pp. 26132-26138, 1997.
Behrend, Lars, et al., European Journal of Cell Biology, "Interaction of casein kinase 1 detla (ck1) with post golgi structures, microtubules and the spindle apparatus", vol. 79, pp. 240-251, 2000.
Calabokis, Maritza et al., Parasitology International, "Biochemical and enzymatic characterization of partially purified casein kinase-1 like activity from *Trypanosoma cruzi*", vol. 51, pp. 25-39, 2002.
Cohen, Philip, et al., Nature Reviews, Drug Discovery, "Protein kinases-the major drug targets of the twenty-first century?" vol. 1, pp. 309-315, 2002.
Coombs, G.H., et al., International Journal for Parasitology, "Recent advances in the search for new anti-coccidial drugs", vol. 32, pp. 497-508, 2002.
Donald, Robert G.K., et al., Eukaryotic Cell, "*Toxoplasma gondii* cyclic GMP-dependent kinase: chemotherapeutic targeting of an essential parasite protein kinase", vol. 1, No. 3, pp. 317-328, 2002.
Donald, Robert, G.K., et al., Molecular & Biochemical Parasitology, "Molecualr characterization of a coccidian parasite cGMP dependent protein kinase", vol. 120, pp. 165-175, 2002.
NCBI ESI Sequence, Nucleotide Database, Accession No. CD345581, 2003.
Gross, Stefan D., et al., Cell. Signal., "Casein kinase I: spatial organization and postioning of a multifunctinoal protein kinase family", vol. 10, No. 10, pp. 699-711, 1998.

(Continued)

Primary Examiner—Sheridan Swope
(74) Attorney, Agent, or Firm—Laura M. Ginkel; Sheldon O. Heber

(57) ABSTRACT

Isolated nucleic acid molecules encoding coccidian casein kinase I, CKI, enzymes from the species *Eimeria tenella* and *Toxoplasma gondii* are disclosed. The isolation of these coccidian CKI cDNA sequences results in the disclosure of purified forms of *E. tenella* and *T. gondii* CKI proteins, recombinant vectors and recombinant hosts which express coccidian CKI.

9 Claims, 15 Drawing Sheets

OTHER PUBLICATIONS

Gurnett, Ann M., et al., The Journal of Biological Chemistry, "Purification and molecular characterization of cGMP-dependent protein kinase from Apicomplexan parasites", vol. 277, No. 18, pp. 15913-15922, 2002.

Hopkins, Andrew L., et al., Nature Reviews, Drug Discovery, "The druggable genome", vol. 1, pp. 727-730, 2002.

Kappes, B., et al., Parasitology Today, "An overview of Plasmodium protein kinases", vol. 15, No. 11, pp. 449-454, 1999.

Klimczak, Leszek J., et al., Plant Physiol., "Multiple isoforms of Arabidopsos casein kinase I combine conserved catalytic domains with variable carboxyl-terminal extensions", vol. 109, pp. 687-696, 1995.

Li, Li, et al., Genome Research, "Gene discovery in the Apicomplexa as revealed by EST sequencing and assembly of a comparative gene database", vol. 13, pp. 443-454, 2003.

Moreno-Bueno, Gema, et al., Biochem. Journal, "Isolation and characterization of casein kinase I from *Dictyostelium discoideum*", vol. 349, pp. 527-537, 2000.

Nare, Bakela, et al., Antimicrobial Agents and Chemotherapy, "Evaluation of cyclic GMP-dependent protein kinase inhibitor in treatment of murine toxoplasmosis: gamma interferon is required for efficacy", vol. 46, No. 2, pp. 300-307, 2002.

Ng, Szu-Ting, et al., Experimental Parasitology, "Comparative EST analyses provide insights into gene expression in two asexual developmental stages of *Eimeria tenella*", vol. 101, pp. 168-173, 2002.

Robinson, Lucy C., et al., Molecular Biology of the Cell, "The Yck2 yeast kinase 1 isoform shows cell cycle-specific localization to sites of polarized growth and is required for proper septin organization", vol. 10, pp. 1077-1092, 1999.

Sacerdoti-Sierra, Nina, et al., The Journal of Biological Chemistry, "Release of ecto-protein kinases by the protozoan parasite *Leishmania major*", vol. 272, No. 49, pp. 30760-30765, 1997.

Spadafora, Carmenza, et al., Molecular & Biochemical Parasitology, "Two casein kinase 1 isoforms are differentially expressed in *Trypanosoma cruzi*", vol. 124, pp. 23-26, 2002.

Viera, Lita, L., et al., International Journal for Parasitology, "Effect of pH and temperature on protein kinase release by *Leishmania donovani*", vol. 32, pp. 1085-1093, 2002.

Vielhaber, Erica, et al., IUBMB *Life*, "Casein kinase I: from obscurity to center stage", vol. 51, pp. 73-78, 2001.

Yu, Sidney, et al., Molecular Biology of the Cell, "Casein kinase I regulates membrane binding by ARF GAP1", vol. 13, pp. 2559-2570, 2002.

* cited by examiner

```
   1 GCGGCCGCGT CGACGTCTTT GCTGCCGCAC AGGGAGCAGC AGCAGCCGCC GACCCGATCC
  61 CTTGGGAGCC CACCAAGTGC TGCGCTTGCT TAGCAGCTAC AGGAGCTGCC GCGGGGTTGC
 121 TCCCTGAGGC AGCGTGCATG TATGGTCCGG CAGCCAGCTT GGTGTCGCAG CCGTACTTCT
 181 TGGAAGCGAG AGAGACTGTG GGAGAGCGCA AATCACTCCA GCCGCTTCCA GGGGAGTCTG
 241 GGGACCGCAG GAGCGTTGGA GGCTGCCTGC CGGCATAAAC AGGAACAAGC GCATTCTTAT
 301 TCTTCTGTGG TTGCTGAGTT CTGGCTGCGT TCAAGGGGGT TCACCTCTTC CCCTTCTGGC
 361 GAGTTTTTGC TGCGTCTTTC CCTAAGAAGC AGCGCCACGT GCGTGGCGTG CCTCAGCCTG
 421 ACGCGGTGCA CCTTTTACGT AAGAGCGTCG ATAGCATCGG TCATCTACAG CAGCGTGCTG
 481 CTGCTTCCGT GACCTTTACA CTGCTTGTGG CGGGCCGTCT TGTAGAGGGG CCATCTGCTT
 541 GTTCGCTGCT GGACGCAGAC CCGGCGCCCG ACATTTCCGG CAGCCGGGCA GTTGAGATAA
 601 ACCGGCTGCC CGGTGGCCGT CGAAATTGAA GCAGGATCTC TACAGTAAGG AACAAATCGC
 661 GCTATTTTTA AGGAGTGTGT ATACTTGGGG CGTTACTCGT GAGTATTGCT GATGATGGAC
 721 GTCCGTGTGG GGGGTAAGTA TCGTTTGGGG AGGAAGATTG GGAGCGGATC CTTCGGCGAC
 781 ATCTACCTTG GTACGAACAT CTCAACAGGA GATGAAGTCG CTATCAAATT GGAAAGCGTG
 841 CGGTCTAGGC ATCCACAACT AATCTATGAA AGCAAGCTGT ACAAAATCCT AACGGGTGGA
 901 ATCGGAATCC CGACTCTTTA CTGGTATGGG ATCGAGGGGG ATTACAACGT TATGATTATT
 961 GAGCTTTTGG GCCCGTCTCT TGAGGACCTC TTCAGCATTT GCAACAGAAA GCTTTCTTTG
1021 AAGACTGTTC TGATGCTCGC CGACCAAATG CTAAATCGTA TTGAGTTCGT CCACAGCAGA
1081 CATTTCATCC ATCGAGACAT CAAGCCTGAC AATTTTTTGA TCGGTAGGGG CAAAAAGATG
1141 TCCATTGTTT TTGCTATCGA CTTTGGCCTC GCAAAGAAGT ACAGAGATCC CAGAACACAG
1201 TCCCATATTC CTTATCGAGA AGGGAAGAAC CTGACAGGTA CCGCGAGGTA CGCCTCTGTG
1261 AACACCCACT TGGGAATAGA ACAGAGCAGG CGCGATGATC TGGAAGCGCT CGGCTACGTC
1321 TTAATGTACT TCAACAGAGG TTCCTTACCC TGGCAAGGAT TAAAGGCCAC TACGAAGAAA
1381 GATAAATATG ACAAGATTAT GGAGAAGAAG ATGTCCACCC CTATTGAAGT CCTTTGCAAA
1441 CAATTTCCAT TTGAGTTTAT CACATATCTG AACTATTGCC GGTCTCTGCG ATTCGAAGAT
1501 CGCCCGGACT ATTCCTATTT GAGACGGTTG TTCAAGGATC TTTTCTTCCG TGAGGGATAC
1561 CAGTATGACT TTATATTCGA TTGGACATTT CTGCATGCTG AGAGAGAGCG CGAGCGTCAA
1621 AGACGATCGA TGGTCAACCA AGGCGCAGAA TCAGGGAACC AGTGGAGACG AGACGCGTCG
1681 GGCAGAGATC CACTTGGACG GTTGCCTCAG TTAGAACCGT AATCTCTTTA CGGGCAGATT
1741 GCCGTACGGG TCTTCTGCTC ATTCAGTGGC AGTGCCACCG CAGTGCTATC TGAGGCTGTG
1801 GCTTCAGGAT GTGGTAGCCA GTTACCATGG TCACTTGCCC TCGCTAGGAC AGCCTTCGCA
1861 GGGAAATGTC ACAGTAGCCT GCATTATGTG GTGTGAGAAC TGCTAGCGCA TTCCTGTAGT
1921 TGCTTTTACG AAGCAGGATA CGCAGCGTGC ATCACGCGGT GGTTCGAGCG CTCGCTACGC
1981 ATCACAGGGC TGTGAGGCAA GTTAGTATCT TTGGGGACG AGTTGAGAGT GTCAGAATCG
2041 ATAGTCTCAG GGCATGCAGG CGAAATGGAG GCTGCGCCAG TAGTGCCAGC CGGTGGCGAA
2101 GGCGTCAAAT TTACTTTTTT TGTTGCTGGG GATATTGTTA GAGCAACAAC TTGGGTCTAG
2161 ATGCTACTGA TAAAAAAAAA AA (SEQ ID NO:1).
```

FIG. 1

```
   1 CCTCGTTTTG CTTCATTCCC CGCCTTTTCT CTGTAGCTAA CCAAAGGAAC AAAGTCAGCG
  61 GTAGAAGCCG TTTCTTCTGT CCGCTTCCCA CTCTTCCCGT TCGGCTGCCC CTGCAGAGCG
 121 CCCTTTCTAT GCGTTGCCAC CCGTCTGCAA GTATCGCGTC TTTCGTCTCA TCAGTGATTT
 181 TCTTTGCGTG TCGCGTTCGG GACGCCCTTT TCTCTCCTCA ACTAACTAGC AGACGTTTCT
 241 TCCGTCCCGC ATGCGACAGC GAAGGGCACG TCCCCCCAGT TCTTCATCGC CCACCTGTTG
 301 TGCAACTTGT CGCCCGTCGT TCTTCACTTC TTCTCTCCCA TCCTCTCGTG ACTCTTCCTC
 361 TCGAGAACTC TTTCTGTCGA ACTCTCAACC CCCACGACTG CTGGTTTCGT GGCCGTCCCG
 421 CATGCACCTT GTGTCCCGCC GCCTTGGCGC AAACACCCGC TTTCTCTGCT GTCCGCCTCC
 481 CGGTGGACTT CTCTCCGTGT TTTTTCGTGT TGCCAAAAGT TTGTCTGCTT TGACGTTTCT
 541 CTGCTCACCC ATTGCCCGCT CTTGATGAGG AACGCTCCAC ATTGACAGCG AACTCACAGC
 601 ACGCACCCTC CGCGAGCGGA CTTTCACGAG CGAGGCAAGA ATCCATCGTC ACCCCGCCTA
 661 CACGTACACT ACTCCACTTG GGTGCCCACG CGCGGCTTCT GGGAGACAGA GACGGTCCTC
 721 GTTTTCCGTG TCAGAACTTT GTCGAGGAAA CGCTGCTGCT GGCAGCGGGG ATTGTGACCC
 781 CCCTCGGCGA ACGGGCGAAG CCGCCCTGTC GCGCGTCGCG ACTCAGCTGA GGCGACAGGC
 841 GGTCGGCGGC GTGACCTCTC TTTCTTTTTG CATTCGGCCC TGATTGCAGC ACGAAGGATG
 901 GAGGTCAGGG TCGGAGGCAA GTACCGACTT GGTCGGAAGA TCGGCAGCGG GTCATTCGGT
 961 GATATTTATA TCGGTGCAAA CATTTTGACG GGGGATGAGG TGGCGATCAA GTTGGAGTCT
1021 ATCAAGTCGA AGCACCCGCA GCTGCTCTAT GAGTCGAAGC TGTACAAACT GCTGGCTGGC
1081 GGCATTGGGA TTCCCATGGT CCACTGGTAC GGCATCGAAG GAGACTACAA TGTTATGGTT
1141 ATCGACCTTC TCGGCCCTTC TCTGGAGGAC CTTTTCAGTA TCTGCAATCG CAAACTCTCT
1201 CTCAAGACGG TGTTGATGCT CGCAGACCAG ATGCTCAACC GCATCGAGTT TGTCCATAGC
1261 AAGAACTTCA TCCATCGCGA TATCAAACCC GACAACTTCC TCATTGGCCG TGGAAAGAAG
1321 ATGTCCGTCG TCTACATCAT CGATTTCGGT TTGGCAAAGA AATATCGAGA CCCAAAGACT
1381 CAGCAACATA TCCCATACAG GGAAGGCAAG AACCTAACAG GCACAGCGCG TTACGCTTCC
1441 ATCAACACCC ACCTGGGGAT CGAGCAGAGT CGGCGAGACG ACCTAGAGGC GCTCGGTTAC
1501 GTTCTCATGT ACTTCAATAG AGGTTCTCTT CCGTKGCAGG GTCTGAAGGC GACGACGAAG
1561 AAGGACAAAT ACGACAAGAT TATGGAGAAG AAAATGTCTA CTCCCATCGA AATTTTGTGC
1621 AAGCATTTCC CATTCGAGTT CATCACCTAC TTGAATTACT GCCGGTCCCT GCGCTTCGAG
1681 GATCGTCCTG ACTACGCATA CTTGCGACGC CTGTTCAAAG ACTTGTTTTT TAGAGAGGGA
1741 TATCAGTACG ACTTCATCTT CGACTGGACT TTCATCAACA CGGAGAAGGA TCGCGCGAGT
1801 CGAAGAAGCC AGCAAGTTTA TGTGGAAGAC AACCGGCAAG TTGAGGAGAA TCAGAACGAG
1861 TTGCCGATGT AGGGTGGTCG GTGTGCGGAG GCCGGCGGGG AGCGTGGAGT CCGCTGAGTC
1921 TGGAAGTCTG CAGACTGTGC TCTGGCACTC GACCCACTTG TTTGTGTTTC CCTCGACTCG
1981 CGCAGGTCGA GGAAAACAGA GACGAACAGG TTACCCAGGA GTGTTTTTGG TCAGGACGCG
2041 CGTCTCCCTC TGAGTTTCGC AAAGTTGCCC CTGGAA (SEQ ID NO:3).
```

FIG. 2

```
   1 TTAACCCTCA CTAAAGGGAA CAAAAGCTGG AGCTCCACCG CGGTGGCGGC GCACCGAGGA
  61 AAACGCAGCT CGTAAGAGAC AGTTCTCTCG GTGAGAAGAG CTATCCGAGA AGGACACCAT
 121 GGCGCACCAT CAAGACACCC GCAACCACAC GGGGGTCGGA CCCTCTTCGT CTATCCCTCT
 181 GAAAGATTTG AAGATCGCCG GCGTCTGGAA AATCGGCAGA AAAATCGGAT CCGGTTCCTT
 241 CGGCGACATA TACAAAGGCC TGAATTCTCA GACCGGTCAG GAGGTGGCGC TGAAGGTCGA
 301 AAGCACCAAG GCGAAGCATC CGCAGTTGCT GTACGAATAC AAACTTTTGA AGCATTTGCA
 361 GGGAGGAACG GGCATTGCTC AAGTGTTCTG TTGCGAGACT GCGGGCGACC ATAACATCAT
 421 GGCCATGGAG TTGCTCGGAC CTTCTTTAGA GGACGTCTTC AACTTGTGCA ATCGCACCTT
 481 CTCTCTCAAA ACCATTCTTC TTCTCGCCGA CCAGTTTCTG CAACGCGTCG AGTACATCCA
 541 CTCCAAGAAT TTCATTCACA GAGATATCAA ACCAGATAAC TTTCTTCTCG GCGGTGCCGG
 601 CAATCAAAAC ACGATCTACG TGATCGACTT CGGCCTGGCG AAGAAGTTTC GCGATCCGAA
 661 AACGCACCAA CATATTCCGT ACAGAGAAAA CAAGAATCTC ACGGGAACGG CGCGCTACGC
 721 GTCCATCAGT GCGCATCTGG GTTCCGAGCA GAGTCGCCGA GATGACCTCG AAGCAGTCGG
 781 CTACGTTCTC ATGTACTTCT GTCGAGGAGG CACGCTGCCT TGGCAGGGCA TCAAAGCGAA
 841 TACCAAACAG GAGAAGTACC ACAAGATCAT GGAGAAGAAG ATGTCGACGC CGTCGAGGT
 901 GCTATGCAAG GGATATCCAA GCGAATTTGC CACATACTTG CACTACTGCC GCTCCTTGCG
 961 ATTCGAGGAC CGACCGGACT ACGCCTACCT CAAGCGACTC TTTCGAGATC TCTACATCAA
1021 AGAGGGCTAC GATGACAGTG ACCGCGAATT CGACTGGACA GTGAAACTTT CGTCGCGCAG
1081 TCTCGGACCG CCAAGCAGTC GAGCGCAACA TGTTTTACTG AGTCAAGACA CCCGAACGCG
1141 AGGGAAGCGG GAGACAGATC GACCTGTCGC TGCGCGGAGT GGCGACCGCG AACGAGGAAT
1201 CCATTTCAGC AACGGGAACG TGGGCAATCC TTCGATGGCA ACGAACCCCG GCGGCCTGTC
1261 AGTCATGGTG CATGAACGCA CGAGTCTGGT GGATCAGGGA GACCGTGGGT CGCGCGAAAC
1321 TTCTACGCGG AAAGAAGACG CGAAGGACGG CAGATGGCCA GGAGGCAGAT TTTCTTGTCT
1381 TCCACTGTTA TGTCGGCGCT CTCCGACGAA GGCCTAGATG AACTGCGGAG GCGCTCCTGT
1441 CCCCGCAGTT GGCATCTCTC TCCTTCATTG TCGTTGTTCC CCTGCAACTC GAGTCCACCC
1501 TTGACATCCT CGTCTCTCTC TTCCTGTCGG TTTCCTCTTT CTCGTCCTCT CCCCCCTAGC
1561 TTCGTTCTCT CCTTTCTATC CTGCTTCGGC GTCGCCTCAC TTCTCTCCTC ACTTCTCTCC
1621 CTTTTGTTTT TCTTCGCGGC GTCTCTCCTT CACTCTGTCT CCGCCTCTGA CGCCGCGCGG
1681 GAGCCGTTTC CTGCAGGCAG CTCAGGCAAT ACTGCCTGC AGGTGCCTCT CCTTTTTGAG
1741 CGTCTCTCTT TCCTCGTCGA AACGGTCCTC ACAGCTTCCT CTCCCTGGGG ACGCCGTGGG
1801 CGTAAGTTCT TTTTTTGACG GTCCCGGTGG GCTGGCGTTG TTCGCCTGCC TTCCGCGCAT
1861 GCACTCCGAG CATTTTTGCC TGGCCTGGAC TTCTCCGAGC GAGAGTTGCG GTTTGGCTTC
1921 TGCATCGTCT CCTGCGCTGC TTTCATTTCT CTAGGTTTCT GCTTGCGGCC TCCGTGTACA
1981 GAAATCGGAA GGTGAAGGCG TAGTGGCCAG AGAACGAAGC AAACGAGAGA ACCACGTTCC
2041 ACCTTGTGCG CACGCATGCA TCTACGCATG CACGGTATTT AAGCCGATTT TTTGTGTATG
2101 TATATAGATG TATATATATA TGTATCTACA TGTATCTACC TATATATATG TGTGTGTGTA
2161 AGTGGAAGTG TATTTTTGCA TGTGCAGAAA GCTTTCTTTT CCGCTGGCAT GCTGGAAGAA
2221 GGGCAGGAGG CGACGATCCT GCGAGTCAGG GCGTTCCCTT GTTCCAGTG AGTTAACCGA
2281 ATTGTTTATT GATATGCGTT TGCATGCATC GACAATGGAT CCTAGACACG CCCGTTTAAA
2341 ATCAGAGGTA TTCCTAAAAA AAAAAAAAAA AAA (SEQ ID NO:5).
```

FIG. 3

```
                        1   CKIβ-Nt              *                                                          75
TgCKIβ  (SEQ ID NO:6)   (1)   MAHHQDTRNHTGVGPSSSIPLKDLKIAGVWKIGRKIGSGSFGDIYKGLNSQTGQEVALKVESTKAKHPQLLYEYK
TgCKIα  (SEQ ID NO:4)   (1)   ------------------MEVRVGGKYRLGRKIGSGSFGDIYIGANILTGDEVAIKLESIKSKHPQLLYESK
EtCKIα  (SEQ ID NO:2)   (1)   ------------------MDVRVGGKYRLGRKIGSGSFGDIYLGTNISTGDEVAIKLESVRSRHPQLIYESK
PfCKIα  (SEQ ID NO:21)  (1)   ------------------MEIRVANKYALGKKLGSGSFGDIYVAKDIVTMEEFAVKLESTRSKHPQLLYESK
LmCKI-2 (SEQ ID NO:22)  (1)   ------------------MNVELRVGNRYRIGQKIGSGSFGEIPRGTNIQTGDPVAIKLEQVKTRHPQLTYESR
TcCKI-2 (SEQ ID NO:23)  (1)   ------------------MSLELRVGNRFRLGQKIGAGSFGEIPRGTNIQTGETVAIKLEQAKTRHPQLALEAR
                                                **    *  ********  *   *  **  **    ** ***    ****  **
                        76                                                                               150
TgCKIβ  (SEQ ID NO:6)   (76)  LLKHLQGG---TGIAQVFCCETAGDHNIMAMELLGPSLEDVFNLCNRTPSLKTILLLADQFLQRVEYIHSKNFIH
TgCKIα  (SEQ ID NO:4)   (55)  LYKLLAGG---IGIPMVHWYGIEGDYNVMVIDLLGPSLEDLFSICNRKLSLKTVLMLADQMLNRIEFVHSKNFIH
EtCKIα  (SEQ ID NO:2)   (55)  LYKILTGG---IGIPTLYWYGIEGDYNVMIIELLGPSLEDLFSICNRKLSLKTVLMLADQMLNRIEFVHSRHFIH
PfCKIα  (SEQ ID NO:21)  (55)  LYKILGGG---IGVPKVYWYGIEGDFTIMVLDLLGPSLEDLFTLCNRKPSLKTVLMTADQMLNRIEYVHSKNFIH
LmCKI-2 (SEQ ID NO:22)  (57)  FYRILGSGGGAVGIPMMFYHGVEGEPFNVMVIELLGPSLEDLFSPCGRRLSLKTTLMLADQMISRIEFVHSKSVLH
TcCKI-2 (SEQ ID NO:23)  (57)  FYRILNAGGGVVGIPNILFYGVEGEPFNVMVMDLLGPSLEDLFSFCDRKLSLKTTLMLAEQMIARIEFVHSKSVIH
                               *  *    *    ***  *  **  *   *********  *  *  **** *******  *** **** **
                        151                  CKIα-It                                                    225
TgCKIβ  (SEQ ID NO:6)   (148) RDIKPDNFLLGGAGNQNTIYVIDFGLAKKFRDPKTHQHIPYRENKNLTGTARYASISAHLGSEQSRRDDLBAVGY
TgCKIα  (SEQ ID NO:4)   (127) RDIKPDNFLIGRGKKMSVVYIIDFGLAKKYRDPKTQQHIPYREGKNLTGTARYASINTHLGIEQSRRDDLEALGY
EtCKIα  (SEQ ID NO:2)   (127) RDIKPDNFLIGRGKKMSIVPAIDFGLAKKYRDPRTQSHIPYREGKNLTGTARYASVNTHLGIEQSRRDDLEALGY
PfCKIα  (SEQ ID NO:21)  (127) RDIKPDNFLIGRGKKVTLIHIIDFGLAKKYRDSRSHTHIPYKEGKNLTGTARYASINTHLGIEQSRRDDIEALGY
LmCKI-2 (SEQ ID NO:22)  (132) RDIKPDNFLMGTGKKGHHVYIIDFGLAKKYRDPRTHAHIPYKEGKSLTGTARYCSINTHMGVEQGRRDDMEGIGY
TcCKI-2 (SEQ ID NO:23)  (132) RDMKPDNFLMGTGKKGHHVYVVDFGLAKKYRDPRTHQHIPYKEGKSLTGTARYCSINTHLGIEQSRRDDLEGIGY
                              ********* *  **     *********** ***    *   **** *** ******* *******  **
                        226                                                                              300
TgCKIβ  (SEQ ID NO:6)   (223) VLMYFCRGGTLPWQGIKANTKQEKYHKIMEKKMSTPVEVLCKGYPSEFATYLHYCRSLRFEDRPDYAYLKRLFRD
TgCKIα  (SEQ ID NO:4)   (202) VLMYFNRG-SLPWQGLKATTKKDKYDKIMEKKMSTPIEVLCKQFPFEPITYLNYCRSLRFEDRPDYAYLRRLFKD
EtCKIα  (SEQ ID NO:2)   (202) VLMYFNRG-SLPWQGLKATTKKDKYDKIMEKKMSTPIEVLCKQFPFEPITYLNYCRSLRFEDRPDYSYLRRLFKD
PfCKIα  (SEQ ID NO:21)  (202) VLMYFLRG-SLPWQGLKAISKKDKYDKIMEKKISTSVEVLCRNASFEPVTYLNYCRSLRFEDRPDYTYLRRLLKD
LmCKI-2 (SEQ ID NO:22)  (207) ILMYFLRG-SLPWQGLKAHTKQEKYNRISERKQTTPVELLCKGFPPSEFAAYMNYVRALRFEDKPDYSYLKRMFRD
TcCKI-2 (SEQ ID NO:23)  (207) ILMYFLRG-SLPWQGLKAHTKQEKYSRISERKQTTPVETLCKGFPAEFAAYLNYIRSLRFEDKPDYSYLKRLFRE
                              **** **   ********* **   ** ** *   ** * **    **  * *  ** ****** *** *  *
                        301               CKIα-Ct                                                        375
TgCKIβ  (SEQ ID NO:6)   (298) LYIKEGYDDSDREFDWTVKLSSRSLGPPSSRAQHVLLSQDTRTRGKRETDRPVAARSGDRERGIHFSNGNVGNPS
TgCKIα  (SEQ ID NO:4)   (276) LFFREGYQY-DFIFDWIFINTEKDRASFRSQQVYVEDNRQVEENQNELPM
EtCKIα  (SEQ ID NO:2)   (276) LFFREGYQY-DFIFDWIFLHAERERERQRRSMVNQGAESGNQWRRDASGRDPLGRLPQLEP
PfCKIα  (SEQ ID NO:21)  (276) LFIREGFTY-DFLFDWICVYASEKDKKKMLENKNRFDQTADQEGRDQRNN
LmCKI-2 (SEQ ID NO:22)  (281) LFVREGYHV-DYVFDWTLKRIHESLQBQQSPPGGSNGGGAAGNGSPVNQSPAQGGNGGAPNSANNQESGAPEQQ
TcCKI-2 (SEQ ID NO:23)  (281) LFIREGYHV-DYVFDWTLKRIHENLKAEGSGQQEQKQQQQQQRERGDVEQA
                              ** ****  * ****
                        376               CKIβ-Ct                                                        435
TgCKIβ  (SEQ ID NO:6)   (373) MATNPGGLSVMVHERTSLVDQGDRGSRETSTRKEDAKDGRWPGGRFSCLPLLCRRSPTKA
```

*Brackets mark the catalytic core region

FIG. 4

|        | TgCKIβ | TgCKIα | EtCKIα | PfCK1α | LmCKI-2 | TcCKI-2 |
|--------|--------|--------|--------|--------|---------|---------|
| TgCKIβ | 100    | 48     | 48     | 45     | 44      | 42      |
| TgCKIα |        | 100    | 81     | 68     | 58      | 62      |
| EtCKIα |        |        | 100    | 67     | 59      | 60      |
| PfCK1α |        |        |        | 100    | 52      | 55      |
| LmCKI-2|        |        |        |        | 100     | 75      |
| TcCKI-2|        |        |        |        |         | 100     |

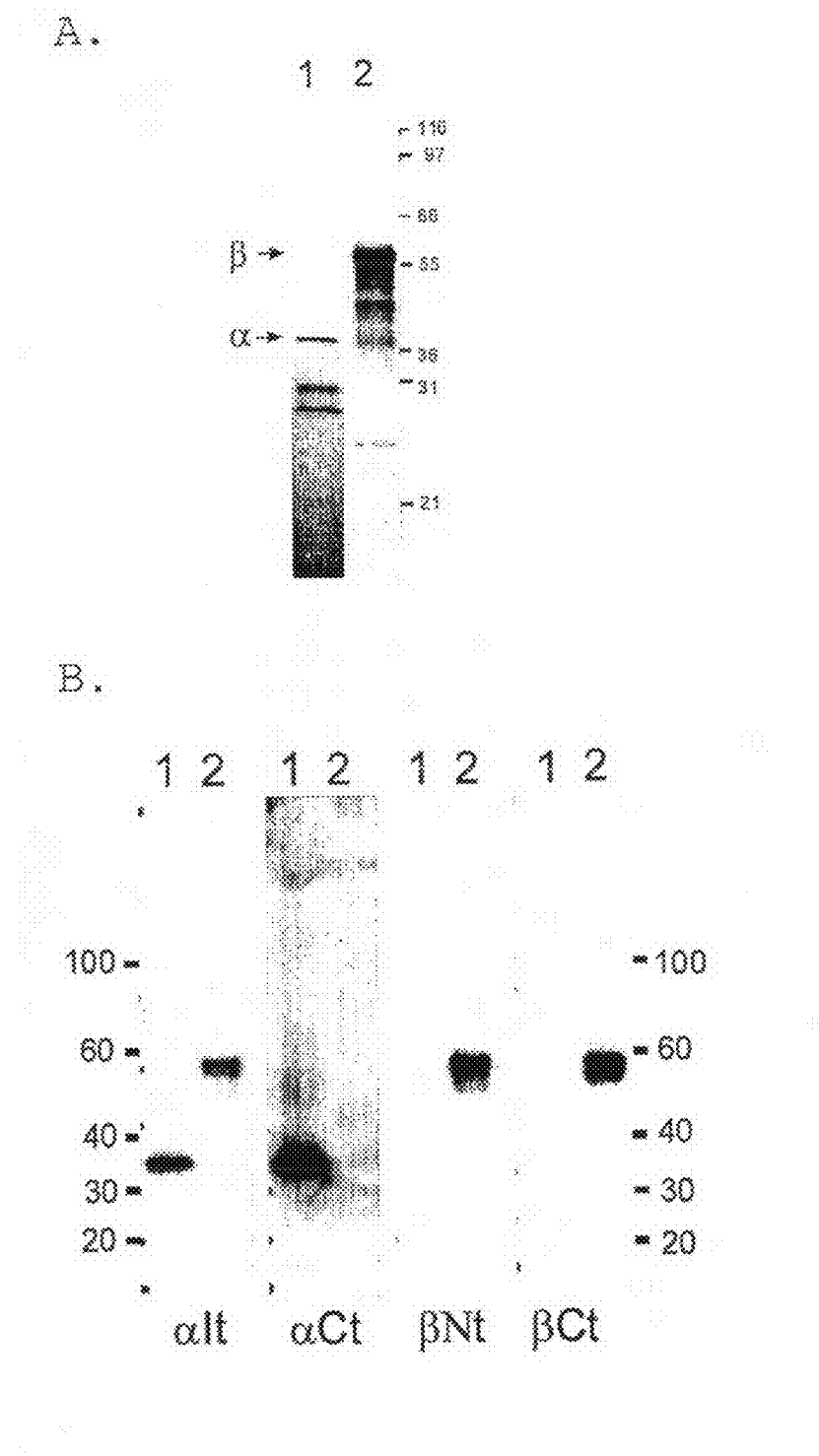
FIG. 8A-B

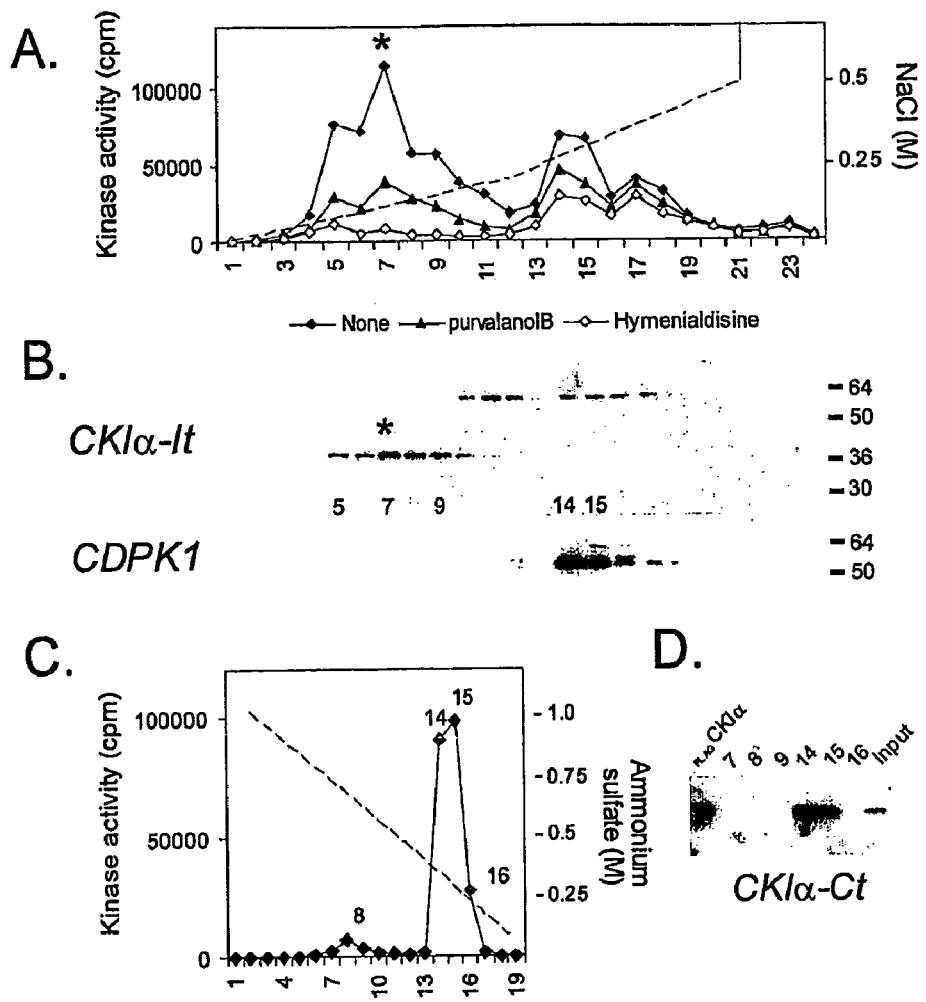
FIG. 9A-D

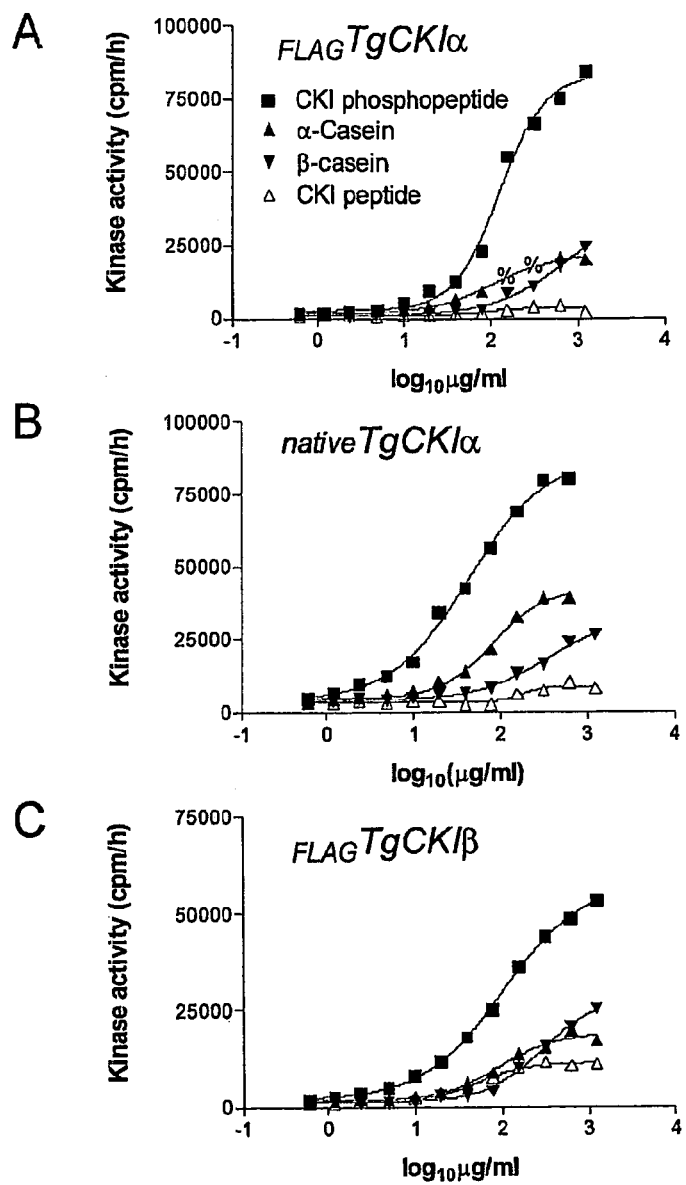
FIG. 10A-C

A.
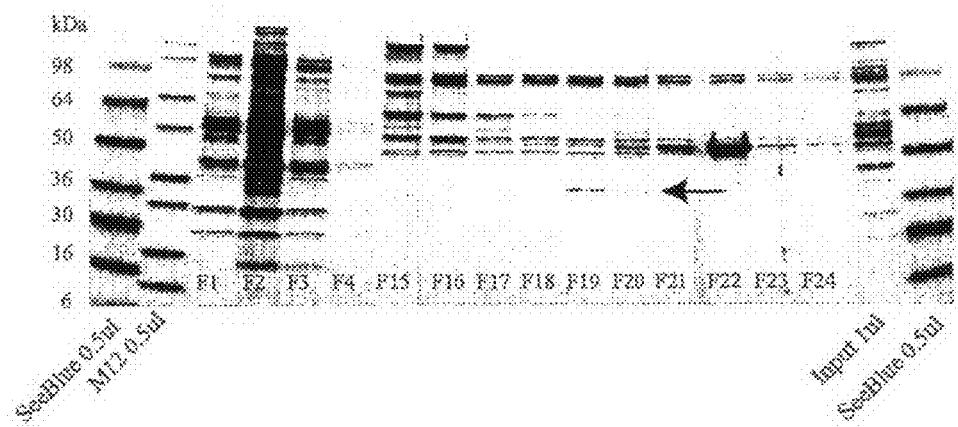
B.
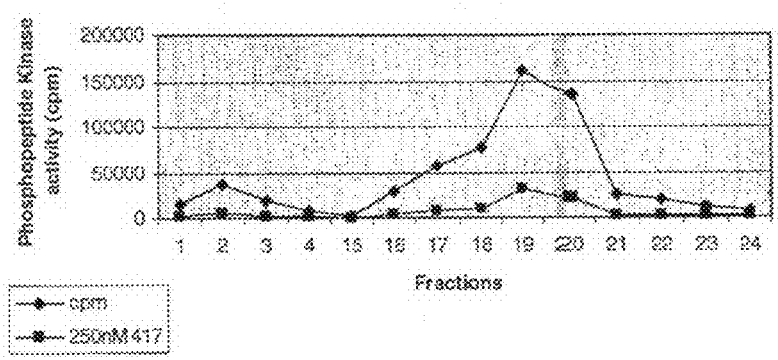
FIG. 11A-B

MDVRVGGKYR LGRKIGSGSF GDIYLGTNIS TGDEVAIKLE
SVRSRHPQLI YESKLYKILT GGIGIPTLYW YGIEGDYNVM
IIELLGPSLE DLFSICNRKL SLKTVLMLAD QMLNRIEFVH
SRHFIHRDIK PDNFLIGRGK KMSIVFAIDF GLAKKYRDPR
TQSHIPYREG KNLTGTARYA SVNTHLGIEQ SRRDDLEALG
YVLMYFNRGS LPWQGLKATT KKDKYDKIME KKMSTPIEVL
CKQFPFEFIT YLNYCRSLRF EDRPDYSYLR RLFKDLFFRE
GYQYDFIFDW TFLHAERERE RQRRSMVNQG AESGNQWRRD
ASGRDPLGRL PQLEP (SEQ ID NO:2)

FIG. 13

POLYNUCLEOTIDES ENCODING COCCIDIAN PARASITE CASEIN KINASE I, A CHEMOTHERAPEUTIC TARGET FOR ANTIPROTOZOAL AGENTS

CROSS-REFERENCE TO RELATED APPLICATIONS

The present application claims the benefit of U.S. Provisional Application No. 60/537,094, filed Jan. 16, 2004, hereby incorporated by reference herein.

FIELD OF THE INVENTION

The present invention relates in part to isolated nucleic acid molecules (polynucleotides) which encode coccidian casein kinase I ("CKI") enzymes, members of the family of serine/threonine CKI proteins. Specifically, the present invention relates to three disclosed CKI proteins isolated from the protozoan species *Eimeria tenella* (EtCKIα) and *Toxoplasma gondii* (TgCKIα and TgCKIβ). The present invention further relates to recombinant vectors and recombinant hosts which contain a DNA fragment encoding a coccidian CKI protein, substantially purified forms of coccidian CKI proteins, and recombinant membrane fractions and/or cell lysates comprising said proteins. Characterization of the coccidian CKI proteins of the present invention allows for screening methods to identify novel coccidiostat compounds that may have therapeutic activity for veterinary and human diseases, including coccidiosis and Toxoplasmosis. Thus, the present invention also relates to methods associated with identifying compounds which specifically modulate coccidian CKI activity.

BACKGROUND OF THE INVENTION

Protein kinases constitute the largest family of human enzymes. As principal regulators of signal transduction pathways, protein kinases play a critical role in a wide range of cellular processes such as proliferation, differentiation and apoptosis. Protein kinases are currently considered to be the largest class of proteins amenable to therapeutic intervention by small molecule drugs (Cohen, P., 2002, *Nat. Rev. Drug Discov.* 1:309-315; Hopkins, A. L. and Groom, C. R., 2002, *Nat. Rev. Drug Discov.* 1:727-730). With the advent of genome databases of clinically important protozoan parasites, it is clear that the evolutionary distance between essential, protozoan protein kinases and the host organisms' corresponding kinase orthologues presents many opportunities for chemotherapeutic intervention of protozoan parasitic proliferation (Doerig, C. et al., 2002, *Trends Parasitol.* 18:366-371). Such differences have been successfully exploited in the case of the coccidian parasite cGMP-dependent protein kinase ("PKG") for which a selective, small molecule inhibitor has been identified that effectively controls parasite proliferation, preventing coccidiosis caused by *Eimeria* species in poultry and Toxoplasmosis caused by *Toxoplasma gondii* in a mouse model (Gurnett, A. M. et al., 2002, *J. Biol. Chem.* 277:15913-15922; Nare, B. et al., 2002, *Antimicrob. Agents Chemother.* 46:300-307; Donald, R. G. K. et al., 2002, *Eukaryot. Cell.* 1:317-328). Knockaert et al. (2000, *Chem. Biol.* 7:411-422) also demonstrated the exploitable differences between parasite kinases and their host cell counterparts using affinity chromatography with an immobilized inhibitor of cyclin-dependent protein kinase ("CDK"), purvalanol B. While the ligand used in these studies is an exceptionally potent and selective inhibitor of mammalian CDKs, affinity chromatography of parasite lysates, including *Plasmodium falciparum*, *Leishmania mexicana*, *Toxoplasma gondii* and *Trypanosoma cruzi*, with this inhibitor showed protozoan casein kinase I ("CKI") proteins, rather than CDK enzymes, tightly bound to the column. In contrast, parallel affinity chromatography of extracts of marine invertebrates and some vertebrate tissues positively identified associated CDKs without selection of CKI enzymes.

Casein kinase I enzymes represent a family of multipotential serine/threonine proteins kinases common to all eukaryotic cells. These enzymes are known to play important and diverse roles in vesicular trafficking, DNA repair, cell cycle progression and cytokinesis in organisms from yeast to humans. In multicellular organisms they also regulate developmental pathways, control circadian rhythms, and have been implicated in Alzheimer's disease progression. Seven members of the CKI family have been identified (α, β, γ1, γ2, γ3, δ, and ε isoforms). It is likely that CKI isoforms also play an essential role in protozoan parasites since these enzymes have been described for *Plasmodium*, *Leishmania* and *Trypanosoma* parasites (Barik, S. et al., 1997, *J. Biol. Chem.* 272: 26132-26138; Vieira, L. L. et al., 2002, *Int. J. Parasitol.* 32:1085-1093; Sacerdoti-Sierra, N. and Jaffe, C. L., 1997, *J. Biol. Chem.* 272:30760-30765; Spadafora, C. et al., 2002, *Mol. Biochem. Parasitol.* 124:23-36; Calabokis, M. et al., 2002, *Parasitol. Int.* 51:25-39). The present invention relates to the cloning, expression and characterization of three novel CKI enzymes, two isoforms from the species *Toxoplasma gondii* (TgCKIα and TgCKIβ) and one from the species *Eimeria tenella* (EtCKIα).

Affinity-ligand purification studies from Knockaert et al., 2000, supra, using an immobilized purvalanol column identified a single binding protein from *T. gondii* lysates. Microsequencing of an eleven amino acid peptide demonstrated that the *Toxoplasma* protein displayed sequence similarity to *Arabidopsis thaliana* CKI, and thus the protein was labeled *Toxoplasma* CKI.

*Eimeria* and *Toxoplasma* are related coccidian protozoa, a subgroup of the phylum *Apicomplexa* that includes intestinal parasites of veterinary and clinical significance. The poultry industry is most severely affected by *Eimeria* spp. infections resulting in coccidiosis. Worldwide costs of $800 million have been reported by the industry, encompassing the cost of prophylactic in-feed medications, alternative treatments if those medications fail, and losses due to mortality and poor feed conversions of infected birds (Allen, P. C. and Fetterer, R. H., 2002, *Clin. Microbiol. Rev.* 15:58-65). Anticoccidial compounds introduced nearly 30 years ago continue to be used prophylactically in poultry operations, the most successful being the polyether ionophores. However, reports of resistance to the current compounds are common due to the constant chemotherapeutic pressure exerted by this class of compounds. *Toxoplasma gondii* infects a broad range of warm-blooded animals. Although it is usually benign in humans, Toxoplasmosis can result in significant mortality and/or morbidity in congenital infections and immunocompromised patients. Current treatment for Toxoplasmosis is a combination therapy using pyrimethamine and sulfonamide; however, significant toxicity often accompanies this treatment regime. There is a current need for identification and development of new compounds for treatment of Toxoplasmosis and coccidiosis. To meet this end, the coccidian casein Kinase I enzymes disclosed herein represent novel targets for the development of broad-spectrum coccidiostat compounds effective against coccidiosis and Toxoplasmosis.

SUMMARY OF THE INVENTION

The present invention relates to an isolated or purified nucleic acid molecule (polynucleotide) which encodes a coccidian casein kinase I ("CKI") protein, a member of the family of multipotential serine/threonine protein kinases common to all eukaryotic cells and known to play important and diverse cellular roles.

The present invention also relates to an isolated or purified nucleic acid molecule (polynucleotide) which encodes a coccidian CKI protein of the *Eimeria* genus, including but not limited to an *Eimeria* CKI protein from the species *Eimeria tenella*.

The present invention further relates to an isolated or purified nucleic acid molecule (polynucleotide) which encodes a coccidian CKI protein of the *Toxoplasma* genus, including but not limited to a *Toxoplasma* CKI protein from the species *Toxoplasma gondii*.

The present invention relates to an isolated or purified nucleic acid molecule (polynucleotide) encoding a coccidian CKI protein, this nucleic acid molecule comprising a nucleotide sequence encoding an amino acid sequence selected from the group consisting of SEQ ID NO:2, SEQ ID NO:4 and SEQ ID NO:6.

The present invention also relates to an isolated or purified nucleic acid molecule (polynucleotide) comprising a DNA molecule selected from the group consisting of SEQ ID NO:1, SEQ ID NO:3 and SEQ ID NO:5, which encode novel coccidian CKI proteins as set forth in SEQ ID NO:2, SEQ ID NO:4 and SEQ ID NO:6, respectively.

The present invention relates to an isolated or purified nucleic acid molecule (polynucleotide) which encodes a coccidian CKI protein, this nucleic acid molecule consisting of a nucleotide sequence encoding an amino acid sequence selected from the group consisting of SEQ ID NO:2, SEQ ID NO:4 and SEQ ID NO:6.

The present invention also relates to an isolated or purified nucleic acid molecule (polynucleotide) consisting of a DNA molecule selected from the group consisting of SEQ ID NO:1, SEQ ID NO:3 and SEQ ID NO:5, which encode novel coccidian CKI proteins as set forth in SEQ ID NO:2, SEQ ID NO:4 and SEQ ID NO:6, respectively.

A preferred aspect of this portion of the present invention is disclosed in FIG. 1, designated as EtCKIα (SEQ ID NO:1), which encodes a novel coccidian CKI protein from the species *Eimeria tenella*.

Another preferred aspect of this portion of the present invention is disclosed in FIG. 2, designated as TgCKIα (SEQ ID NO:3), which encodes a novel coccidian CKI protein from the species *Toxoplasma gondii*.

Another preferred aspect of this portion of the present invention is disclosed in FIG. 3, designated as TgCKIβ (SEQ ID NO:5), which encodes a novel coccidian CKI protein from the species *Toxoplasma gondii*.

The isolated nucleic acid molecules of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The present invention also relates to biologically active fragments or mutants of SEQ ID NO:1 which encode mRNA expressing a novel *Eimeria tenella* CKI protein. Any such biologically active fragment and/or mutant will encode either a protein or protein fragment which at least substantially mimics the enzymatic properties of the *E. tenella* CKI protein as set forth in SEQ ID NO:2. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and would be useful for screening for agonists and/or antagonists of CKI activity.

The present invention also relates to biologically active fragments or mutants of SEQ ID NOs:3 and 5 which encode mRNA expressing novel *Toxoplasma gondii* CKI proteins. Any such biologically active fragment and/or mutant will encode either a protein or protein fragment which at least substantially mimics the enzymatic properties of the *T. gondii* CKI protein as set forth in SEQ ID NO:4 and SEQ ID NO:6, respectively. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and would be useful for screening for agonists and/or antagonists of CKI activity.

The present invention further relates to a purified nucleic acid molecule (polynucleotide) encoding a coccidian CKI protein, wherein said nucleic acid molecule comprises a nucleotide sequence selected from the group consisting of: (a) a nucleotide sequence which encodes an amino acid sequence as set forth in SEQ ID NO:2, SEQ ID NO:4 or SEQ ID NO:6; (b) a nucleotide sequence which hybridizes under conditions of moderate to high stringency to the complement of a second nucleic acid molecule which encodes an amino acid sequence as set forth in SEQ ID NO:2, SEQ ID NO:4 or SEQ ID NO:6; and, (c) a nucleotide sequence which hybridizes under conditions of moderate stringency to the complement of a second nucleic acid molecule as set forth in SEQ ID NO:1, SEQ ID NO:3 or SEQ ID NO:5; and, wherein said nucleic acid molecule encodes an amino acid sequence that has at least about 80% identity to at least one of the amino acid sequences as set forth in SEQ ID NO:2, SEQ ID NO:4 or SEQ ID NO:6.

The present invention also relates to recombinant vectors and recombinant host cells, both prokaryotic and eukaryotic, as well as both stably and transiently transformed/transfected cells, which contain the substantially purified nucleic acid molecules disclosed throughout this specification.

The present invention further relates in part to a substantially purified form of a coccidian CKI protein, as exemplified herein with the identification and disclosure of novel CKI proteins of the *Eimeria* and *Toxoplasma* genera.

The present invention also relates to a substantially purified form of a coccidian CKI protein of the *Eimeria* genus, including but not limited to an *Eimeria* CKI protein from the species *Eimeria tenella*.

The present invention further relates to a substantially purified form of a coccidian CKI protein of the *Toxoplasma* genus, including but not limited to a *Toxoplasma* CKI protein from the species *Toxoplasma gondii*.

The present invention relates to a substantially purified form of a coccidian CKI protein comprising an amino acid sequence selected from group consisting of SEQ ID NO:2, SEQ ID NO:4 and SEQ ID NO:6. Characterization of one or more of these proteins allows for screening methods to identify novel casein kinase I modulators that may have therapeutic activity for animal and/or human health. Thus, the coccidian proteins described herein represent potential antiparasitic chemotherapeutic targets for the identification and development of anti-parasitic compounds for the treatment of Toxoplasmosis and coccidiosis.

The present invention further relates to a substantially purified form of a coccidian CKI protein consisting of an amino acid sequence selected from the group consisting of SEQ ID NO:2, SEQ ID NO:4 and SEQ ID NO:6.

A preferred aspect of this portion of the present invention is disclosed in FIG. 4 as SEQ ID NO:2, designated EtCKIα, and fully processed forms thereof, which represents a novel coccidian CKI protein from the species *Eimeria tenella*.

Another preferred aspect of this portion of the present invention is disclosed in FIG. 4 as SEQ ID NO:4, designated TgCKIα, and fully processed forms thereof, which represents a novel coccidian CKI protein from the species *Toxoplasma gondii*.

Another preferred aspect of this portion of the present invention is disclosed in FIG. 4 as SEQ ID NO:6, designated TgCKIβ, and fully processed forms thereof, which represents a novel coccidian CKI protein from the species *Toxoplasma gondii*.

The present invention further relates to a substantially purified coccidian CKI protein, said protein comprising at least about 80% amino acid sequence identity with an amino acid sequence selected from the group consisting of SEQ ID NO:2, SEQ ID NO:4 and SEQ ID NO:6.

A preferred aspect of the present invention relates to a substantially purified, fully processed (including any proteolytic processing, glycosylation and/or phosphorylation) and mature coccidian CKI protein obtained from a recombinant host cell (both prokaryotic and eukaryotic, as well as both stably and transiently transformed or transfected) containing a DNA expression vector comprising a nucleotide sequence as set forth in SEQ ID NOs:1, 3 and/or 5, and expresses the *Eimeria* or *Toxoplasma* CKI precursor or mature form of the respective protein. It is especially preferred that the recombinant host cells be a eukaryotic host cell, including but not limited to a mammalian or insect cell line. It is additionally preferable that said coccidian CKI proteins of the present invention be expressed in an inducible eukaryotic expression system.

The present invention also relates to biologically active fragments and/or mutants of the coccidian CKI proteins as initially set forth as SEQ ID NO:2, SEQ ID NO:4 or SEQ ID NO:6, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for agonists and/or antagonists for CKI function.

The present invention further relates to a substantially purified membrane preparation, a partially purified membrane preparations or a cell lysate which has been obtained from a recombinant host cell (both prokaryotic and eukaryotic) transformed or transfected (both stably and transiently) with a DNA expression vector which comprises the nucleic acid molecules of the present invention. These membrane fractions and/or cell lysates will comprise either wild-type or mutant forms of the coccidian CKI proteins of the present invention.

A preferred aspect of the present invention relates to a substantially purified membrane preparation, a partially purified membrane preparations or a cell lysate which has been obtained from a recombinant host cell transformed or transfected with a DNA expression vector which comprises a complete open reading frame as set forth in SEQ ID NOs: 1, 3 and/or 5, expressing a functional form of the respective coccidian CKI protein, either of the *Eimeria* or *Toxoplasma* genera. The subcellular membrane fractions and/or cell lysates from the recombinant host cells (both prokaryotic and eukaryotic, as well as both stably and transiently transformed/transfected cells) contain the functional and processed proteins encoded by the nucleic acids of the present invention. The recombinant-based membrane preparation may comprise a coccidian CKI protein that is essentially free from contaminating proteins, including but not limited to other coccidian source proteins. A preferred aspect of the invention is a membrane preparation or cell lysate which contains one or more coccidian casein kinase I protein(s) comprising the functional form of the CKI proteins as disclosed in FIG. 4 (SEQ ID NO:2, designated EtCKIα; SEQ ID NO:4, designated TgCKIα; and/or SEQ ID NO:6, designated TgCKIβ). These subcellular membrane fractions and/or cell lysates will comprise either wild-type or mutant variations which are biologically functional forms of the *Eimeria* or *Toxoplasma* CKI proteins disclosed herein. It is contemplated that any functional single, homomultimer or heteromultimer combination of the coccidian CKI proteins disclosed herein may be expressed at levels substantially above endogenous levels and hence will be useful in various assays described throughout this specification. A preferred eukaryotic host cell of choice to express the CKI proteins of the present invention is a mammalian or insect based cell line.

The present invention also relates to polyclonal and monoclonal antibodies raised in response to a coccidian CKI protein, including but not limited to CKI proteins of the *Eimeria* and *Toxoplasma* genera disclosed herein, or a biologically active fragment thereof.

The present invention also relates to coccidian CKI fusion constructs, including but not limited to fusion constructs which express at least a portion of the CKI protein linked to various markers, including but in no way limited to the FLAG epitope, GFP (Green fluorescent protein), the MYC epitope, GST, and Fc. Any such fusion constructs may be expressed in the cell line of interest and used to screen for modulators of one or more coccidian CKI proteins.

The present invention relates to methods of expressing coccidian CKI proteins and biological equivalents, including but not limited to CKI proteins of the *Eimeria* and *Toxoplasma* genera, as exemplified by the CKI proteins disclosed herein. The present invention further relates to assays employing coccidian CKI these gene products, as well as recombinant host cells which comprise DNA constructs which express the corresponding proteins. The present invention also relates to compounds identified through the use of coccidian casein kinase I genes and expressed CKI proteins, including agonists or antagonists of coccidian CKI proteins, including but not limited to CKI proteins of the *Eimeria* and *Toxoplasma* genera (e.g., *E. tenella* and *T. gondii*), which act to modulate casein kinase I activity.

As used herein, "substantially free from other nucleic acids" means at least 90%, preferably 95%, more preferably 99%, and even more preferably 99.9%, free of other nucleic acids. As used interchangeably with the terms "substantially free from other nucleic acids" or "substantially purified" or "isolated nucleic acid" or "purified nucleic acid," this term also refer to a DNA molecule which comprises a coding region for a coccidian CKI protein, including but not limited CKI proteins of the *Eimeria* or *Toxoplasma* genera, that has been purified away from other cellular components. Thus, a coccidian CKI DNA preparation that is substantially free from other nucleic acids will contain, as a percent of its total nucleic acid, no more than 10%, preferably no more than 5%, more preferably no more than 1%, and even more preferably no more than 0.1%, of non-coccidian CKI nucleic acids. Whether a given coccidian CKI DNA preparation is substantially free from other nucleic acids can be determined by such conventional techniques of assessing nucleic acid purity as, e.g., agarose gel electrophoresis combined with appropriate staining methods, e.g., ethidium bromide staining, or by sequencing.

As used herein, "substantially free from other proteins" or "substantially purified" means at least 90%, preferably 95%, more preferably 99%, and even more preferably 99.9%, free of other proteins. Thus, a coccidian CKI protein preparation, including but not limited to protein preparations of *Eimeria* or *Toxoplasma* CKI proteins, that is substantially free from other proteins will contain, as a percent of its total protein, no more than 10%, preferably no more than 5%, more preferably no more than 1%, and even more preferably no more than 0.1%, of non-coccidian CKI proteins. Whether a given coccidian CKI protein preparation is substantially free from other proteins can be determined by such conventional techniques of assessing protein purity as, e.g., sodium dodecyl sulfate polyacrylamide gel electrophoresis ("SDS-PAGE") combined with appropriate detection methods, e.g., silver staining or immunoblotting. As used interchangeably with the terms "substantially free from other proteins" or "substantially purified," the terms "isolated coccidian CKI protein" or "purified coccidian CKI protein" or "isolated *Eimeria* CKI protein" or "purified *Eimeria* CKI proteins" or "isolated *Toxoplasma* CKI protein" or "purified *Toxoplasma* CKI protein" also refer to coccidian CKI proteins, including but not limited to CKI proteins from the *Eimeria* or *Toxoplasma* genera, that have been isolated from a natural source. Use of the term "isolated" or "purified" indicates that the CKI proteins of the present invention have been removed from their normal cellular environment. Thus, an isolated coccidian CKI protein may be in a cell-free solution or placed in a different cellular environment from that in which it occurs naturally. The term "isolated" does not imply that an isolated coccidian CKI protein is the only protein present, but instead means that a coccidian CKI protein is substantially free of other proteins and non-amino acid material (e.g., nucleic acids, lipids, carbohydrates) naturally associated with the coccidian CKI protein in vivo. Thus, for example, a coccidian CKI protein that is recombinantly expressed in a prokaryotic or eukaryotic cell and substantially purified from this host cell which does not naturally (i.e., without intervention) express this CKI protein is, of course, an "isolated coccidian CKI protein" under any circumstances referred to herein. As noted above, a coccidian CKI protein preparation, including but not limited to a protein preparation of *Eimeria* or *Toxoplasma* CKI proteins, that is an isolated or purified coccidian CKI protein will be substantially free from other proteins and will contain, as a percent of its total protein, no more than 10%, preferably no more than 5%, more preferably no more than 1%, and even more preferably no more than 0.1%, of non-coccidian CKI proteins.

As used interchangeably herein, "functional equivalent" or "biologically active equivalent" means a protein which does not have exactly the same amino acid sequence as the corresponding, naturally occurring, coccidian CKI due to alternative splicing, deletions, mutations, substitutions, or additions, but retains substantially the same biological activity as the corresponding, naturally occurring, coccidian CKI. Such functional equivalents will have significant amino acid sequence identity with the naturally occurring coccidian CKI proteins, genes and cDNAs encoding such functional equivalents and can be detected by reduced stringency hybridization with DNA sequences encoding naturally occurring coccidian CKI proteins. For example, a naturally occurring coccidian CKI protein from the *E. tenella* species disclosed herein comprises the amino acid sequence shown as SEQ ID NO:2 and is encoded by SEQ ID NO:1.

As used herein, "a conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

As used herein, the term "coccidian" refers to a subgroup of the *Apicomplexa* in which the sexual stage occurs in the gut of the definitive host animal. Infectious diploid oocycts are generated in the gut epithelium and are subsequently released into the environment in the feces. Thus all of the coccidia hare an enteric lifecycle stage. *Toxoplasma* is unusual in that the haploid (tachyzoite) stage is not limited to the gut, but can invade and proliferate in any vertebrate cell. As with other coccidia, the sexual stage of *Toxoplasma* occurs in the gut, in this case that of the cat. Examples of other coccidia of clinical or veterinary importance include *Cryptosporidium parvum* (diarrhea in livestock and humans), *Sarcocystis neurona* (neurological symptoms in horses) and *Neospora caninum* (abortions in cattle and neurological symptoms in dogs).

BRIEF DESCRIPTION OF THE DRAWINGS

FIG. 1 shows the nucleotide sequence which encodes a coccidian CKI protein from the species *Eimeria tenella*, as set forth in SEQ ID NO:1, and designated EtCKIα.

FIG. 2 shows the nucleotide sequence which encodes a coccidian CKI protein from the species *Toxoplasma gondii*, as set forth in SEQ ID NO:3, and designated TgCKIα.

FIG. 3 shows the nucleotide sequence which encodes a coccidian CKI protein from the species *Toxoplasma gondii*, as set forth in SEQ ID NO:5, and designated TgCKIβ.

FIG. 4 shows a ClustalW alignment of amino acid sequences of parasite CKI proteins, comparing the predicted protein sequences of EtCKIα (SEQ ID NO:2), TgCKIα (SEQ ID NO:4) and TgCKIβ (SEQ ID NO:6) with sequences of *Plasmodium falciparum* (PfCKIα; GenBank Accession No. AF017139; SEQ ID NO:21), *Leishmania major* (LmCKI-2; GenBank Accession No. AAF35365; SEQ ID NO:22) and *Trypanosoma cruzi* (TcCKI-2; GenBank Accession No. AAF00025; SEQ ID NO:23). Peptide fragments identified by microsequencing of affinity purified proteins (Knockaert et al., 2000, supra) are highlighted in shaded boxes. TgCKI peptide epitopes, against which antisera were raised, are shown in labeled boxes. N- and C-terminal epitopes are isoform specific (CKIβ-Nt, CKIα-Ct, CKIβ-Ct). An internal epitope (CKIα-It) was chosen to raise antisera that should recognize all of the aligned CKI isoforms. Conserved amino acids are indicated with a small asterisk below the individual amino acid letter. Brackets are included to delineate the boundaries of the catalytic core region of the enzymes.

FIG. 5 shows percentage amino acid identities amongst the sequences shown in FIG. 4.

FIG. 8 shows the SDS-PAGE analysis of recombinant TgCKIα and TgCKIβ. Enzymes were purified from $E.\ coli$ lysates by FLAG-agarose- and MonoQ ion-exchange chromatography. (A) Lanes 1 and 2 correspond to fractions of peak CK activity from a NaCl gradient and are stained with silver. Bands corresponding to TgCKIα (lane 1, 'α') and TgCKIβ (lane 2, 'β') are indicated with arrows. Other bands in lane 1 are contaminating $E.\ coli$ proteins. Minor bands in lane 2 are $_{FLAG}$TgCKIβ degradation products. (B) Western blotting of affinity purified TgCKIα (lane 1) and TgCKIβ (lane 2) with antisera to peptide epitopes shown in FIG. 4.

FIG. 9 shows the partial purification of native TgCKIα from $T.\ gondii$ tachyzoites. Soluble protein was prepared from $2\times10^{10}$ parasites and fractionated by chromatography-on a 5 mL HiTrapQ column. CKI phosphopeptide kinase activity was determined in the presence of 1 µM purvalanol B (triangles) and 200 mM hymenialdisine (open diamonds) or without (closed diamonds) (A). (B) A peak of compound-sensitive CK activity (fraction 7, asterisk) is associated with a 38 kDa band detected with isoform non-selective CK antisera ('CKIα-It'). A second ~60 kDa band is visible in lanes 10-18 that does not correlate with CK activity or cross-react with antisera selective for TgCKIβ in duplicate blots (not shown). Kinase activities in fractions 14 and 15 correlate with the presence of CDPK1, which is partially sensitive to purvalanol B and hymenialdisine (see also Table 2). The CKI phosphopeptide is not an optimal substrate for TgCDPK1, so the activity represented underestimates its presence. Fraction 7 was applied to a 0.1 mL HIC column (C) and 0.1 mL fractions with kinase activity probed with TgCKIα-specific antisera ('CKIα-Ct') (D). Control lanes include column input (MonoQ fraction 7, 'input') and affinity purified recombinant TgCKIα ('$_{FLAG}$TgCKIα'). Properties of CKI activity in pooled peak fractions (14 and 15) are shown in Tables 1 and 2 ('native CKIα').

FIG. 10 shows the substrate selectivity of recombinant and native TgCKIα. Substrate titrations were performed and $K_{m(app)}$ and $V_{max(app)}$ values determined (see Table 1). For native (B) and recombinant TgCKIα (A), significant levels of concentration-dependent kinase activity were detected only with the synthetic CKI phosphopeptide and bovine casein substrates. The phosphopeptide, KRRRALS(p)VASLPGL (SEQ ID NO:19), yielded two to three fold higher levels of activity than α- or β-casein. Recombinant TgCKIβ showed similar properties (Table 1); however, an unphosphorylated CKI peptide, RRKDLHDDEEDEAMSITA (SEQ ID NO:13), also showed some low level activity (C).

FIG. 11 shows the partial purification of native EtCKIα from $E.\ tenella$ tachyzoites. FIG. 11A shows a silver stained SDS-PAGE gel of fractions (F1-F24) eluted from a MonoS chromatography column, the third of three steps used in the partial purification of the native EtCKIα enzyme. A single ~40 kDa band correlates with peak phosphopeptide kinase activity (B). This kinase activity is sensitive to Compound 20, a (pyrimidyl)(phenyl)substituted fused heteroaryl PKG kinase inhibitor disclosed in PCT International Application PCT/US02/19507 (International publication number WO 03/000682).

FIG. 13 shows results of the tandem LC-MS/MS analysis of the ~40 kDa protein isolated from SDS-PAGE gels (see FIG. 12). The sequence represents the predicted 39 kDa open reading frame of EtCKIα (SEQ ID NO:2). Seven peptide fragments were identified that matched the amino acid sequence of the cloned EtCKIα gene (see shaded boxes). The identity of five of these peptides was confirmed in subsequent methyl ester derivitization experiments.

DETAILED DESCRIPTION OF THE INVENTION

Figure 6:
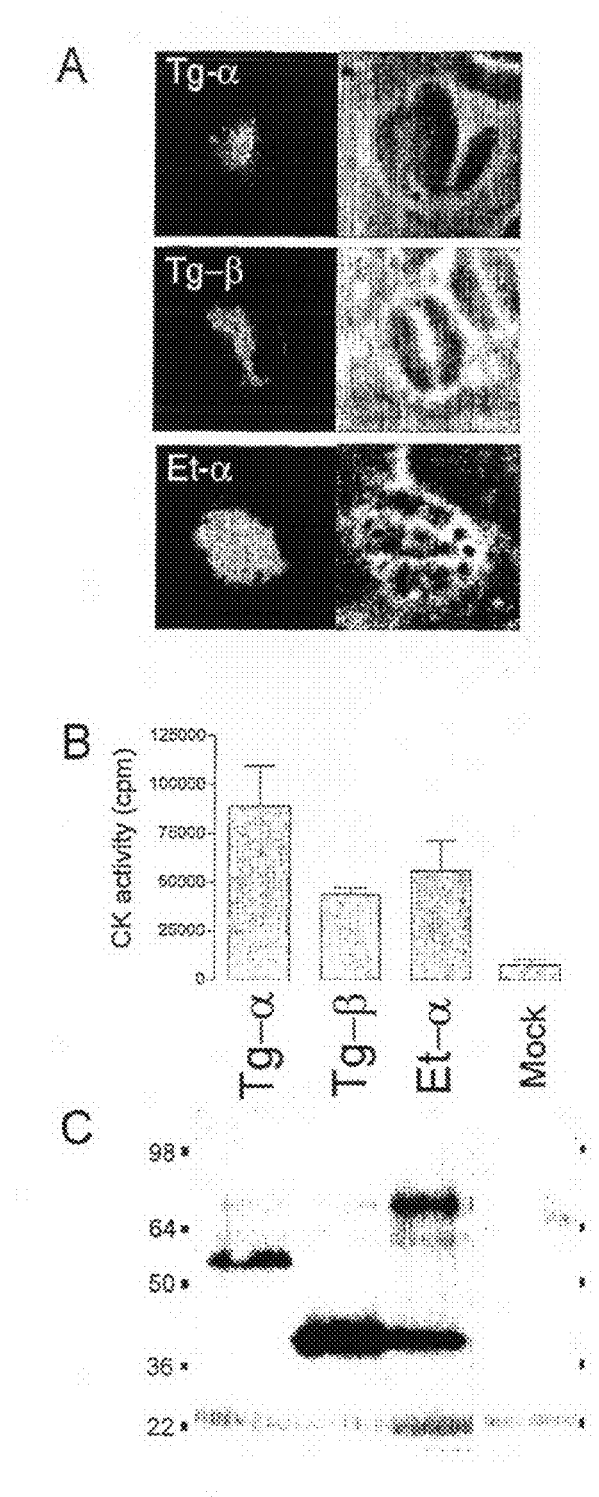
FIG. 6 show the transient expression of recombinant coccidian CKI proteins in tachyzoites. Tachyzoites were transfected with 100 μg of expression plasmid $_{FLAG}$TgCKIα ('Tg-α'), $_{FLAG}$TgCKIβ ('Tg-β'), $_{FLAG}$EtCKIα ('Et-α') or vector alone ('Mock') in triplicate, and inoculated into cultures of HFF cell monolayers (slides or T-25 flasks). At 24 hours post-infection, anti-FLAG immunofluorescence analyses ("IFA") shows that TgCKIα and EtCKIα are expressed in the cytosol, while TgCKIβ exhibits membrane-associated staining (A). At 48 hours post-infection, recombinant enzyme was immunoprecipitated with FLAG agarose from lysates prepared from infected monolayers. Immunoprecipitated enzyme was assayed for kinase activity with casein (B), and detected by Western blot (C) using antisera to internal epitope shared by the different isoforms ('CKIα-It', FIG. 4).

The present invention relates to isolated or purified nucleic acids (polynucleotides) and protein forms which represent coccidian casein kinase I proteins, members of the family of multipotential serine/threonine protein kinases common to all eukaryotic cells and generally referred to herein as the CKI family. This specification discloses three DNA molecules encoding coccidian CKI proteins of the $Eimeria$ or $Toxoplasma$ genera, specifically CKI proteins from the species $Eimeria\ tenella$ and $Toxoplasma\ gondii$. The isolated or purified nucleic acid molecules of the present invention, and the proteins they encode, are substantially free from other nucleic acids or proteins, respectively. For most cloning purposes, DNA is a preferred nucleic acid.

The present invention further relates to an isolated or purified nucleic acid molecule (polynucleotide) sequence which encodes a coccidian CKI protein of the $Eimeria$ or $Toxoplasma$ genera, including but not limited to CKI proteins isolated from the species $Eimeria\ tenella$ and $Toxoplasma\ gondii$. The $Eimeria$ and $Toxoplasma$ genera are contained within the phylum $Apicomplexa$ which comprises many protozoa of medical and/or veterinary importance. Protozoan species contained within the $Eimeria$ and $Toxoplasma$ genera generate coccidial infections, labeled coccidiosis in the case of $Eimeria$ infections and Toxoplasmosis in the case of $Toxoplasma$ infections. Coccidiosis is induced by the intake of a large number of sporulated oocysts by susceptible birds, causing relatively sudden loss of body weight and the onset of clinical signs. While different host organisms are infected by different species of *Eimeria*, poultry are the major hosts for *Eimeria* spp. The United States Department of Agriculture currently recognizes six (6) categories of poultry: chicken, duck, goose, guinea, pigeon and turkey. These different poultry hosts are infected by different species of *Eimeria*, domestic chicken being infected by the following seven species: *E. acervulina, E. brunette, E. maxima, E. mitis, E. necatrix, E. praecox* and *E. tenella*. Pathogenicities of *Eimeria* infection in chickens range from moderate to severe, *E. tenella* and *E. necatrix* being the most pathogenic. Therefore, one aspect of the present invention relates to purified nucleic acids which encode *Eimeria* CKI proteins isolated from species of *Eimeria* that infect poultry, including but not limited to *E. tenella* and *E. necatrix*. In contrast, the *Toxoplasma* genus is a currently considered a monospecific genus, comprised solely of the species *Toxoplasma gondii*. *T. gondii* is an obligate intracellular protozoan parasite that infects a broad range of warm-blood animals. In humans, Toxoplasmosis is usually benign; however, in immunocompromised individuals, including cancer and transplant patients and individuals infected with HIV, *T. gondii* infection can result in life-threatening encephalitis, culminating in focal brain disease. Therefore, another aspect of the present invention relates to purified nucleic acids with encode *Toxoplasma* CKI proteins isolated from the species *Toxoplasma gondii*.

The present invention further relates to an isolated or purified nucleic acid molecule (polynucleotide) which encodes a coccidian CKI protein, said nucleic acid molecule comprising or consisting of a nucleotide sequence encoding an amino acid sequence selected from the group consisting of SEQ ID NO:2, SEQ ID NO:4 and SEQ ID NO:6.

One embodiment of the present invention relates to an isolated nucleic acid molecule (polynucleotide) comprising or consisting of a nucleotide sequence encoding the amino acid sequence as disclosed in FIG. 4 as SEQ ID NO:2. The amino acid sequence set forth in SEQ ID NO:2 represents the alpha ('α') isoform of a novel coccidian CKI identified from *Eimeria tenella*, designated EtCKIα. Another embodiment of the present invention relates to an isolated nucleic acid molecule (polynucleotide) comprising or consisting of a nucleotide sequence encoding the amino acid sequences set forth in SEQ ID NO:4 or SEQ ID NO:6. The amino acid sequences set forth in SEQ ID NO:4 and SEQ ID NO:6 represent the alpha ('α') and beta ('β') isoforms of novel coccidian CKI identified from *Toxoplasma gondii*, designated TgCKIα and TgCKIβ, respectively. The present invention includes codon redundancy which may result in different DNA molecules expressing identical proteins to those disclosed in the present invention.

The present invention also relates to an isolated nucleic acid molecule (polynucleotide) comprising or consisting of a DNA molecule selected from the group consisting of SEQ ID NO:1, SEQ ID NO:3 and SEQ ID NO:5, which encode novel coccidian CKI proteins as set forth in SEQ ID NO:2, SEQ ID NO:4 and SEQ ID NO:6, respectively.

One embodiment of the present invention relates to an isolated or purified nucleic acid molecule (polynucleotide) which encodes mRNA which expresses a novel *Eimeria* CKI protein, this DNA molecule comprising or consisting of the nucleotide sequence disclosed herein as FIG. 1 and as set forth in SEQ ID NO:1. The nucleotide sequence set forth in SEQ ID NO:1 encodes the alpha ('α') isoform of a novel coccidian CKI identified from *Eimeria tenella*, designated EtCKIα, as set forth in SEQ ID NO:2. Another embodiment of the present invention relates to an isolated or purified nucleic acid molecule (polynucleotide) which encodes mRNA which expresses a novel *Toxoplasma* CKI protein, this DNA molecule comprising or consisting of the nucleotide sequence disclosed herein as FIG. 2 and as set forth in SEQ ID NO:3. The nucleotide sequence set forth in SEQ ID NO:3 encodes the alpha ('α') isoform of a novel coccidian CKI identified from *Toxoplasma gondii*, designated TgCKIα, as set forth in SEQ ID NO:4. A still further embodiment of the present invention relates to an isolated or purified nucleic acid molecule (polynucleotide) which encodes mRNA which expresses a novel *Toxoplasma* CKI protein, this DNA molecule comprising or consisting of the nucleotide sequence disclosed herein as FIG. 3 and as set forth in SEQ ID NO:5. The nucleotide sequence set forth in SEQ ID NO:5 encodes the beta ('β') isoform of a novel coccidian CKI identified from *Toxoplasma gondii*, designated TgCKIβ, as set forth in SEQ ID NO:6.

The identification of three novel CKI proteins from *Eimeria tenella* and *Toxoplasma gondii*, coccidian parasites of the *Apicomplexa*, is described in detail in Example 1, said proteins designated as EtCKIα, TgCKIα and TgCKIβ. These enzymes have been further characterized as outlined in the Examples Section. These cDNA molecules, as discussed herein, are especially useful as therapeutic targets for the identification and development of anti-parasitic compounds, including but not limited to small molecule agonists and antagonists, for the treatment of Toxoplasmosis and coccidiosis. The cDNAs of the present invention, or portions thereof, are also useful for diagnostic purposes, including but not limited to protein antibody based assays and sequence based assays. In diagnostic assays, the cDNAs would be used to detect infection with said corresponding parasites and the disease states they induce.

The CKI proteins of the present invention are members of the casein kinase I family of serine/threonine protein kinases, a group of highly related, ubiquitously expressed monomeric kinases found in all eukaryotic organisms from protozoa to man. CKI was originally identified for its ability to phosphorylate the milk protein casein; however, this historical name is considered somewhat of a misnomer since milk casein is neither a natural substrate for this family of enzymes nor a particularly optimal one. Seven isoforms have been characterized in mammals, with additional specific homologues identified in lower organisms such as *Saccharomyces cerevisiae, Schizosaccharomyces pombe, Caenorhabditis elegans, Xenopus laevis* and *Drosophila melanogaster*. Among other protein kinases, casein kinase I appears to be unique, having no closely related kinases with similar sequences; however, members of the CKI family are highly related. CKI protein kinases have similar sequence domains consisting of a central kinase domain that is flanked by divergent amino- and carboxyl-terminal regions of variable lengths. CKI proteins preferably phosphorylate substrates having a negatively charged region located upstream of the phosphorylation site, particularly substrates with the recognition motifs S/T(P)-X-X-S/T or $D_n$-X-X-S/T, wherein S/T(P) represents (phospho)serine or threonine, X is any amino acid, and D is aspartic acid. Importantly, since this recognition motif is relatively ambiguous, many potential substrates for CKI proteins have been identified. Thus, CKI enzymes have been found to play important and diverse roles within the cell, including contributing to vesicular trafficking, DNA repair, cell cycle progression and cytokinesis in organisms from yeast to humans (Gross, S. D. et al., 1998, *Cell Signal.* 10:699-711; Yu, S. et al., 2002, *Mol. Biol. Cell* 13:2559-2570; Robinson, L. C. et al., 1999, *Mol. Biol. Cell* 10:1077-1092; Behrend, L. et al., 2000, *Eur. J. Cell Biol.* 79:240-251; Vielhaber, E. and Virshup, D. M., 2001, *IUBMB Life.* 51:73-78). CKI enzymes have recently been described for a number of eukaryotic protozoan parasites, including *Plasmodium, Leishmania* and *Trypanosoma*. Using affinity chromatography with an immobilized CDK inhibitor (purvalanol B) column, Knockaert et al., 2000, supra, identified a 38 kDa protein from *Toxoplasma*

*gondii* extracts with a strong affinity for the purvalanol B matrix. Microsequencing identified the protein as a CKI isoform. The present invention relates in part to novel coccidian CKI proteins from both *T. gondii* (TgCKIα and TgCKIβ) and *E. tenella* (EtCKIα).

The present invention also relates to either biologically active fragments or mutants of SEQ ID NO:1 which encode mRNA expressing a novel *Eimeria tenella* CKI protein, designated EtCKIα. Any such biologically active fragment and/or mutant will encode a protein or protein fragment which at least substantially mimics the enzymatic properties of the *E. tenella* CKI protein as set forth in SEQ ID NO:2. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and is useful for the identification of modulators of CKI activity.

The present invention further relates to either biologically active fragments or mutants of SEQ ID NO:3 which encode mRNA expressing a novel *Toxoplasma gondii* CKI protein, designated TgCKIα. Any such biologically active fragment and/or mutant will encode a protein or protein fragment which at least substantially mimics the enzymatic properties of the *T. gondii* CKI protein as set forth in SEQ ID NO:4. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and is useful for the identification of modulators of CKI activity.

The present invention still further relates to either biologically active fragments or mutants of SEQ ID NO:5 which encode mRNA expressing a novel *Toxoplasma gondii* CKI protein, designated TgCKIβ. Any such biologically active fragment and/or mutant will encode a protein or protein fragment which at least substantially mimics the enzymatic properties of the *T. gondii* CKI protein as set forth in SEQ ID NO:6. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and is useful for the identification of modulators of CKI activity.

The present invention also relates to isolated or purified nucleic acid molecules which are fusion constructions useful in assays to identify compounds which modulate wild-type coccidian CKI activity, including but not limited to the activity of casein kinase I proteins isolated from the *Eimeria* or *Toxoplasma* genera. Such assays can be used to evaluate the safety and efficacy of specific inhibitors of CKI in host organisms susceptible to coccidial infections. These inhibitors will be useful to treat diseases including coccidiosis and *Toxoplasma* in a range of host organisms, including but not limited to poultry (e.g., domestic chickens) and humans. A preferred aspect of this portion of the invention includes but is not limited to FLAG epitope-tagged CKI fusion constructs. These fusion constructs comprise the open reading frame of the coccidian CKI protein as an in-frame fusion at the $NH_2$— terminus of the nucleotide sequence encoding the FLAG peptide. Exemplified FLAG epitope-tagged *E. tenella* and *T. gondii* CKI fusion proteins, designated as $_{FLAG}$EtCKIα, $_{FLAG}$TgCKIα, $_{FLAG}$TgCKIβ, are described in Example 2 herein. Soluble recombinant FLAG-CKI fusion proteins may be expressed in various expression systems, including *Spodoptera frugiperda* (Sf21) insect cells (Invitrogen) using a baculovirus expression vector (pAcG2T, Pharmingen).

The isolated nucleic acid molecule of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The degeneracy of the genetic code is such that, for all but two amino acids, more than a single codon encodes a particular amino acid. This allows for the construction of synthetic DNA that encodes any of the coccidian CKI proteins disclosed herein where the nucleotide sequence of the synthetic DNA differs significantly from the nucleotide sequence of SEQ ID NO:1, SEQ ID NO:3 or SEQ ID NO:5, but still encodes the same coccidian CKI proteins as set forth in SEQ ID NO:2, SEQ ID NO:4 and SEQ ID NO:6, respectively. Such synthetic DNAs are intended to be within the scope of the present invention. If it is desired to express such synthetic DNAs in a particular host cell or organism, the codon usage of such synthetic DNAs can be adjusted to reflect the codon usage of that particular host, thus leading to higher levels of expression of the coccidian CKI protein in the host. In other words, this redundancy in the various codons which code for specific amino acids is within the scope of the present invention. Therefore, the present invention discloses codon redundancy which may result in differing DNA molecules expressing an identical protein.

It is known that DNA sequences coding for a peptide may be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate or a receptor for a ligand.

As used herein, "purified" and "isolated" are utilized interchangeably to stand for the proposition that the nucleic acid, protein, or respective fragment thereof in question has been substantially removed from its in vivo environment so that it may be manipulated by the skilled artisan, such as but not limited to nucleotide sequencing, restriction digestion, site-directed mutagenesis, and subcloning into expression vectors for a nucleic acid fragment, as well as obtaining the protein or protein fragment in pure quantities so as to afford the opportunity to generate polyclonal antibodies, monoclonal antibodies, amino acid sequencing, and peptide digestion. Therefore, the nucleic acids claimed herein may be present in whole cells or in cell lysates or in a partially purified or substantially purified form. A nucleic acid is considered substantially purified when it is purified away from environmental contaminants. Thus, a nucleic acid sequence isolated from cells is considered to be substantially purified when purified from cellular components by standard methods, while a chemically synthesized nucleic acid sequence is considered to be substantially purified when purified from its chemical precursors.

A preferred aspect of the present invention is disclosed in FIG. 1 and SEQ ID NO:1, a coccidian cDNA encoding an *Eimeria tenella* casein kinase I alpha gene, EtCKIα, disclosed as follows:

```
                                                                    (SEQ ID NO:1)
   1 GCGGCCGCGT CGACGTCTTT GCTGCCGCAC AGGGAGCAGC AGCAGCCGCC GACCCGATCC
  61 CTTGGGAGCC CACCAAGTGC TGCGCTTGCT TAGCAGCTAC AGGAGCTGCC GCGGGGTTGC
 121 TCCCTGAGGC AGCGTGCATG TATGGTCCGG CAGCCAGCTT GGTGTCGCAG CCGTACTTCT
 181 TGGAAGCGAG AGAGACTGTG GGAGAGCGCA ATCACTCCA GCCGCTTCCA GGGGAGTCTG
 241 GGGACCGCAG GAGCGTTGGA GGCTGCCTGC CGGCATAAAC AGGAACAAGC GCATTCTTAT
 301 TCTTCTGTGG TTGCTGAGTT CTGGCTGCGT TCAAGGGGGT TCACCTCTTC CCCTTCTGGC
 361 GAGTTTTTGC TGCGTCTTTC CCTAAGAAGC AGCGCCACGT GCGTGGCGTG CCTCAGCCTG
 421 ACGCGGTGCA CCTTTTACGT AAGAGCGTCG ATAGCATCGG TCATCTACAG CAGCGTGCTG
 481 CTGCTTCCGT GACCTTTACA CTGCTTGTGG CGGGCCGTCT TGTAGAGGGG CCATCTGCTT
 541 GTTCGCTGCT GGACGCAGAC CCGGCGCCCG ACATTTCCGG CAGCCGGGCA GTTGAGATAA
 601 ACCGGCTGCC CGGTGGCCGT CGAAATTGAA GCAGGATCTC TACAGTAAGG AACAAATCGC
 661 GCTATTTTTA AGGAGTGTGT ATACTTGGGG CGTTACTCGT GAGTATTGCT GATGATGGAC
 721 GTCCGTGTGG GGGGTAAGTA TCGTTTGGGG AGGAAGATTG GGAGCGGATC CTTCGGCGAC
 781 ATCTACCTTG GTACGAACAT CTCAACAGGA GATGAAGTCG CTATCAAATT GGAAAGCGTG
 841 CGGTCTAGGC ATCCACAACT AATCTATGAA AGCAAGCTGT ACAAAATCCT AACGGGTGGA
 901 ATCGGAATCC CGACTCTTTA CTGGTATGGG ATCGAGGGGG ATTACAACGT TATGATTATT
 961 GAGCTTTTGG GCCCGTCTCT TGAGGACCTC TTCAGCATTT GCAACAGAAA GCTTTCTTTG
1021 AAGACTGTTC TGATGCTCGC CGACCAAATG CTAAATCGTA TTGAGTTCGT CCACAGCAGA
1081 CATTTCATCC ATCGAGACAT CAAGCCTGAC AATTTTTTGA TCGGTAGGGG CAAAAAGATG
1141 TCCATTGTTT TTGCTATCGA CTTTGGCCTC GCAAAGAAGT ACAGAGATCC CAGAACACAG
1201 TCCCATATTC CTTATCGAGA AGGGAAGAAC CTGACAGGTA CCGCGAGGTA CGCCTCTGTG
1261 AACACCCACT TGGGAATAGA ACAGAGCAGG CGCGATGATC TGGAAGCGCT CGGCTACGTC
1321 TTAATGTACT TCAACAGAGG TTCCTTACCC TGGCAAGGAT TAAAGGCCAC TACGAAGAAA
1381 GATAAATATG ACAAGATTAT GGAGAAGAAG ATGTCCACCC CTATTGAAGT CCTTTGCAAA
1441 CAATTTCCAT TGAGTTTAT CACATATCTG AACTATTGCC GGTCTCTGCG ATTCGAAGAT
1501 CGCCCGGACT ATTCCTATTT GAGACGGTTG TTCAAGGATC TTTTCTTCCG TGAGGGATAC
1561 CAGTATGACT TTATATTCGA TTGGACATTT CTGCATGCTG AGAGAGAGCG CGAGCGTCAA
1621 AGACGATCGA TGGTCAACCA AGGCGCAGAA TCAGGGAACC AGTGGAGACG AGACGCGTCG
1681 GGCAGAGATC CACTTGGACG GTTGCCTCAG TTAGAACCGT AATCTCTTTA CGGGCAGATT
1741 GCCGTACGGG TCTTCTGCTC ATTCAGTGGC AGTGCCACCG CAGTGCTATC TGAGGCTGTG
1801 GCTTCAGGAT GTGGTAGCCA GTTACCATGG TCACTTGCCC TCGCTAGGAC AGCCTTCGCA
1861 GGGAAATGTC ACAGTAGCCT GCATTATGTG GTGTGAGAAC TGCTAGCGCA TTCCTGTAGT
1921 TGCTTTTACG AAGCAGGATA CGCAGCGTGC ATCACGCGGT GGTTCGAGCG CTCGCTACGC
1981 ATCACAGGGC TGTGAGGCAA GTTAGTATCT TTGGGGGACG AGTTGAGAGT GTCAGAATCG
2041 ATAGTCTCAG GGCATGCAGG CGAAATGGAG GCTGCGCCAG TAGTGCCAGC CGGTGGCGAA
2101 GGCGTCAAAT TTACTTTTTT TGTTGCTGGG GATATTGTTA GAGCAACAAC TTGGGTCTAG
2161 ATGCTACTGA TAAAAAAAA AA.
```

Another preferred aspect of the present invention is disclosed in FIG. 2 and SEQ ID NO:3, a coccidian cDNA encoding a *Toxoplasma gondii* casein kinase I alpha gene, TgCKIα, disclosed as follows:

(SEQ ID NO:3)
```
   1 CCTCGTTTTG CTTCATTCCC CGCCTTTTCT CTGTAGCTAA CCAAAGGAAC AAAGTCAGCG
  61 GTAGAAGCCG TTTCTTCTGT CCGCTTCCCA CTCTTCCCGT TCGGCTGCCC CTGCAGAGCG
 121 CCCTTTCTAT GCGTTGCCAC CCGTCTGCAA GTATCGCGTC TTTCGTCTCA TCAGTGATTT
 181 TCTTTGCGTG TCGCGTTCGG GACGCCCTTT TCTCTCCTCA ACTAACTAGC AGACGTTTCT
 241 TCCGTCCCGC ATGCGACAGC GAAGGGCACG TCCCCCCAGT TCTTCATCGC CCACCTGTTG
 301 TGCAACTTGT CGCCCGTCGT TCTTCACTTC TTCTCTCCCA TCCTCTCGTG ACTCTTCCTC
 361 TCGAGAACTC TTTCTGTCGA ACTCTCAACC CCCACGACTG CTGGTTTCGT GGCCGTCCCG
 421 CATGCACCTT GTGTCCCGCC GCCTTGGCGC AAACACCCGC TTTCTCTGCT GTCCGCCTCC
 481 CGGTGGACTT CTCTCCGTGT TTTTTCGTGT TGCCAAAAGT TTGTCTGCTT TGACGTTTCT
 541 CTGCTCACCC ATTGCCCGCT CTTGATGAGG AACGCTCCAC ATTGACAGCG AACTCACAGC
 601 ACGCACCCTC CGCGAGCGGA CTTTCACGAG CGAGGCAAGA ATCCATCGTC ACCCCGCCTA
 661 CACGTACACT ACTCCACTTG GGTGCCCACG CGCGGCTTCT GGGAGACAGA GACGGTCCTC
 721 GTTTTCCGTG TCAGAACTTT GTCGAGGAAA CGCTGCTGCT GGCAGCGGGG ATTGTGACCC
 781 CCCTCGGCGA ACGGGCGAAG CCGCCCTGTC GCGCGTCGCG ACTCAGCTGA GGCGACAGGC
 841 GGTCGGCGGC GTGACCTCTC TTTCTTTTTG CATTCGGCCC TGATTGCAGC ACGAAGGATG
 901 GAGGTCAGGG TCGGAGGCAA GTACCGACTT GGTCGGAAGA TCGGCAGCGG GTCATTCGGT
 961 GATATTTATA TCGGTGCAAA CATTTTGACG GGGGATGAGG TGGCGATCAA GTTGGAGTCT
1021 ATCAAGTCGA AGCACCCGCA GCTGCTCTAT GAGTCGAAGC TGTACAAACT GCTGGCTGGC
1081 GGCATTGGGA TTCCCATGGT CCACTGGTAC GGCATCGAAG GAGACTACAA TGTTATGGTT
1141 ATCGACCTTC TCGGCCCTTC TCTGGAGGAC CTTTTCAGTA TCTGCAATCG CAAACTCTCT
1201 CTCAAGACGG TGTTGATGCT CGCAGACCAG ATGCTCAACC GCATCGAGTT TGTCCATAGC
1261 AAGAACTTCA TCCATCGCGA TATCAAACCC GACAACTTCC TCATTGGCCG TGGAAAGAAG
1321 ATGTCCGTCG TCTACATCAT CGATTTCGGT TTGGCAAAGA AATATCGAGA CCCAAAGACT
1381 CAGCAACATA TCCCATACAG GGAAGGCAAG AACCTAACAG GCACAGCGCG TTACGCTTCC
1441 ATCAACACCC ACCTGGGGAT CGAGCAGAGT CGGCGAGACG ACCTAGAGGC GCTCGGTTAC
1501 GTTCTCATGT ACTTCAATAG AGGTTCTCTT CCGTKGCAGG GTCTGAAGGC GACGACGAAG
1561 AAGGACAAAT ACGACAAGAT TATGGAGAAG AAAATGTCTA CTCCCATCGA AATTTTGTGC
1621 AAGCATTTCC CATTCGAGTT CATCACCTAC TTGAATTACT GCCGGTCCCT GCGCTTCGAG
1681 GATCGTCCTG ACTACGCATA CTTGCGACGC CTGTTCAAAG ACTTGTTTTT TAGAGAGGGA
1741 TATCAGTACG ACTTCATCTT CGACTGGACT TTCATCAACA CGGAGAAGGA TCGCGCGAGT
1801 CGAAGAAGCC AGCAAGTTTA TGTGGAAGAC AACCGGCAAG TTGAGGAGAA TCAGAACGAG
1861 TTGCCGATGT AGGGTGGTCG GTGTGCGGAG GGCGGCGGGG AGCGTGGAGT CCGCTGAGTC
1921 TGGAAGTCTG CAGACTGTGC TCTGGCACTC GACCCACTTG TTTGTGTTTC CCTCGACTCG
1981 CGCAGGTCGA GGAAAACAGA GACGAACAGG TTACCCAGGA GTGTTTTGG TCAGGACGCG
2041 CGTCTCCCTC TGAGTTTCGC AAAGTTGCCC CTGGAA.
```

Another preferred aspect of the present invention is disclosed in FIG. 3 and SEQ ID NO:5, a coccidian cDNA encoding a *Toxoplasma gondii* casein kinase I beta gene, TgCKIβ, disclosed as follows:

(SEQ ID NO:5)

```
   1 TTAACCCTCA CTAAAGGGAA CAAAAGCTGG AGCTCCACCG CGGTGGCGGC GCACCGAGGA
  61 AAACGCAGCT CGTAAGAGAC AGTTCTCTCG GTGAGAAGAG CTATCCGAGA AGGACACCAT
 121 GGCGCACCAT CAAGACACCC GCAACCACAC GGGGGTCGGA CCCTCTTCGT CTATCCCTCT
 181 GAAAGATTTG AAGATCGCCG GCGTCTGGAA ATCGGCAGA AAAATCGGAT CCGGTTCCTT
 241 CGGCGACATA TACAAAGGCC TGAATTCTCA GACCGGTCAG GAGGTGGCGC TGAAGGTCGA
 301 AAGCACCAAG GCGAAGCATC CGCAGTTGCT GTACGAATAC AAACTTTTGA AGCATTTGCA
 361 GGGAGGAACG GGCATTGCTC AAGTGTTCTG TTGCAGAGACT GCGGGCGACC ATAACATCAT
 421 GGCCATGGAG TTGCTCGGAC CTTCTTTAGA GGACGTCTTC AACTTGTGCA ATCGCACCTT
 481 CTCTCTCAAA ACCATTCTTC TTCTCGCCGA CCAGTTTCTG CAACGCGTCG AGTACATCCA
 541 CTCCAAGAAT TTCATTCACA GAGATATCAA ACCAGATAAC TTTCTTCTCG GCGGTGCCGG
 601 CAATCAAAAC ACGATCTACG TGATCGACTT CGGCCTGGCG AAGAAGTTTC GCGATCCGAA
 661 AACGCACCAA CATATTCCGT ACAGAGAAAA CAAGAATCTC ACGGGAACGG CGCGCTACGC
 721 GTCCATCAGT GCGCATCTGG GTTCCGAGCA GAGTCGCCGA GATGACCTCG AAGCAGTCGG
 781 CTACGTTCTC ATGTACTTCT GTCGAGGAGG CACGCTGCCT TGGCAGGGCA TCAAAGCGAA
 841 TACCAAACAG GAGAAGTACC ACAAGATCAT GGAGAAGAAG ATGTCGACGC CGTCGAGGT
 901 GCTATGCAAG GGATATCCAA GCGAATTTGC CACATACTTG CACTACTGCC GCTCCTTGCG
 961 ATTCGAGGAC CGACCGGACT ACGCCTACCT CAAGCGACTC TTTCGAGATC TCTACATCAA
1021 AGAGGGCTAC GATGACAGTG ACCGCGAATT CGACTGGACA GTGAAACTTT CGTCGCGCAG
1081 TCTCGGACCG CCAAGCAGTC GAGCGCAACA TGTTTTACTG AGTCAAGACA CCCGAACGCG
1141 AGGGAAGCGG GAGACAGATC GACCTGTCGC TGCGCGGAGT GGCGACCGCG AACGAGGAAT
1201 CCATTTCAGC AACGGGAACG TGGGCAATCC TTCGATGGCA ACGAACCCCG GCGGCCTGTC
1261 AGTCATGGTG CATGAACGCA CGAGTCTGGT GGATCAGGGA GACCGTGGGT CGCGCGAAAC
1321 TTCTACGCGG AAAGAAGACG CGAAGGACGG CAGATGGCCA GGAGGCAGAT TTTCTTGTCT
1381 TCCACTGTTA TGTCGGCGCT CTCCGACGAA GGCCTAGATG AACTGCGGAG GCGCTCCTGT
1441 CCCCGCAGTT GGCATCTCTC TCCTTCATTG TCGTTGTTCC CCTGCAACTC GAGTCCACCC
1501 TTGACATCCT CGTCTCTCTC TTCCTGTCGG TTTCCTCTTT CTCGTCCTCT CCCCCCTAGC
1561 TTCGTTCTCT CCTTTCTATC CTGCTTCGGC GTCGCCTCAC TTCTCTCCTC ACTTCTCTCC
1621 CTTTTGTTTT TCTTCGCGGC GTCTCTCCTT CACTCTGTCT CCGCCTCTGA CGCCGCGCGG
1681 GAGCCGTTTC CTGCAGGCAG CTCAGGCAAT ACCTGCCTGC AGGTGCCTCT CCTTTTTGAG
1741 CGTCTCTCTT TCCTCGTCGA AACGGTCCTC ACAGCTTCCT CTCCCTGGGG ACGCCGTGGG
1801 CGTAAGTTCT TTTTTTGACG GTCCCGGTGG GCTGGCGTTG TTCGCCTGCC TTCCGCGCAT
1861 GCACTCCGAG CATTTTTGCC TGGCCTGGAC TTCTCCGAGC GAGAGTTGCG GTTTGGCTTC
1921 TGCATCGTCT CCTGCGCTGC TTTCATTTCT CTAGGTTTCT GCTTGCGGCC TCCGTGTACA
1981 GAAATCGGAA GGTGAAGGCG TAGTGGCCAG AGAACGAAGC AAACGAGAGA ACCACGTTCC
2041 ACCTTGTGCG CACGCATGCA TCTACGCATG CACGGTATTT AAGCCGATTT TTTGTGTATG
2101 TATATAGATG TATATATATA TGTATCTACA TGTATCTACC TATATATATG TGTGTGTGTA
2161 AGTGGAAGTG TATTTTTGCA TGTGCAGAAA GCTTTCTTTT CCGCTGGCAT GCTGGAAGAA
2221 GGGCAGGAGG CGACGATCCT GCGAGTCAGG GCGTTCCCTT GTTTCCAGTG AGTTAACCGA
2281 ATTGTTTATT GATATGCGTT TGCATGCATC GACAATGGAT CCTAGACACG CCCGTTTAAA
2341 ATCGAGGGTA TTCCTAAAAA AAAAAAAAAA AAA.
```

The above-exemplified isolated DNA molecules, shown in FIGS. 1-3, comprise the following characteristics:

EtCKIα (SEQ ID NO:1): 2182 nucleotides; initiating Met at nuc. 715-717 and "TAA" termination codon at nuc.1720-1722; open reading frame results in an expressed protein of 335 amino acids, as set forth in SEQ ID NO:2.

TgCKIα (SEQ ID NO:3): 2076 nucleotides; initiating Met at nuc. 898-900 and "TAG" termination codon at nuc. 1870-1872; open reading frame results in an expressed protein of 324 amino acids, as set forth in SEQ ID NO:4.

TgCKIβ (SEQ ID NO:5): 2373 nucleotides; initiating Met at nuc. 119-121 and "TAG" termination codon at nuc. 1415-1417; open reading frame results in an expressed protein of 432 amino acids, as set forth in SEQ ID NO:6).

The percent identity of the amino acid sequences encoded by the exemplified cDNA molecules of the present invention to both each other as well as other eukaryotic protozoan parasite CKI isoforms are as follows:

TgCKIα and TgCKIβ—48%;
TgCKIα and PfCKIα—68%;
TgCKIα and LmCKI-2—58%;
TgCKIα and TcCKI-2—62%;
TgCKIβ and PfCKIα—45%;
TgCKIβ and LmCKI-2—44%;
TgCKIβ and TcCKI-2—42%;
EtCKIα and TgCKIα—81%;
EtCKIα and TgCKIβ—48%;
EtCKIα and PfCKIα—67%;
EtCKIα and LmCKI-2—59%; and,
EtCKIα and TcCKI-2—60%.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment, and non-homologous sequences can be disregarded for comparison purposes). In one embodiment of the invention, the length of a reference sequence aligned for comparison purposes is at least 30%, 40%, 50%, 60% or 70% of the length of the reference sequence, more preferably at least 80%, and most preferably at least 90% or more of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm (see e.g., *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, and as exemplified in calculating the percent identities between the coccidian amino acid sequences disclosed herein, the percent identity between two amino acid sequences is determined based on alignments generated with the Clustal W algorithm (Thompson, J. D. et al., 1994, *Nucleic acids Res.* 22:4673-4680). This algorithm is incorporated into many commercial software packages, in this case the alignX software program in the Vector NTI suite (version 8.0). Default Clustal W parameters were used to generate pairwise alignments from which percent identity values were calculated (gap opening penalty of 10; gap extension penalty of 0.1). The percent identity is defined as the number of identical residues divided by the total number of residues and multiplied by 100. If sequences in the alignment are of different lengths (due to gaps or extensions), the length of the longest sequence will be used in the calculation, representing the value for total length.

To this end, the present invention further relates to an isolated or purified nucleic acid molecule encoding a coccidian CKI protein, including but not limited to a CKI protein of the *Eimeria* or *Toxoplasma* genera, wherein the nucleic acid molecule comprises a nucleotide sequence selected from the group consisting of: (a) a nucleotide sequence which encodes an amino acid sequence as set forth in SEQ ID NO:2, SEQ ID NO:4 and/or SEQ ID NO:6; (b) a nucleotide sequence which hybridizes under conditions of moderate to high stringency to the complement of a second nucleic acid molecule which encodes an amino acid sequence as set forth in SEQ ID NO:2, SEQ ID NO:4 and/or SEQ ID NO:6; and, (c) a nucleotide sequence which hybridizes under conditions of moderate stringency to the complement of a second nucleic acid molecule as set forth in SEQ ID NO:1, SEQ ID NO:3 and/or SEQ ID NO:5; and, wherein said nucleic acid molecule encodes an amino acid sequence that has at least about 80% identity to at least one of the amino acid sequences as set forth in SEQ ID NO:2, SEQ ID NO:4 and/or SEQ ID NO:6.

One embodiment of the present invention relates to an isolated or purified nucleic acid molecule encoding a coccidian CKI protein, including but not limited to a CKI protein of the *Eimeria* or *Toxoplasma* genera, wherein the nucleic acid molecule comprises a nucleotide sequence selected from the group consisting of: (a) a nucleotide sequence which encodes an amino acid sequence as set forth in SEQ ID NO:2 and/or SEQ ID NO:4; (b) a nucleotide sequence which hybridizes under conditions of moderate to high stringency to the complement of a second nucleic acid molecule which encodes an amino acid sequence as set forth in SEQ ID NO:2 and/or SEQ ID NO:4; and, (c) a nucleotide sequence which hybridizes under conditions of moderate stringency to the complement of a second nucleic acid molecule as set forth in SEQ ID NO:1 and/or SEQ ID NO:3; and, wherein said nucleic acid molecule encodes an amino acid sequence that has at least about an 80% identity to at least one of the amino acid sequences as set forth in SEQ ID NO:2 and/or SEQ ID NO:4.

Another embodiment of the present invention relates to an isolated or purified nucleic acid molecule encoding a coccidian CKI protein, including but not limited to a CKI protein of the *Eimeria* or *Toxoplasma* genera, wherein the nucleic acid molecule comprises a nucleotide sequence selected from the group consisting of: (a) a nucleotide sequence which encodes an amino acid sequence as set forth in SEQ ID NO:4 and/or SEQ ID NO:6; (b) a nucleotide sequence which hybridizes under conditions of moderate to high stringency to the complement of a second nucleic acid molecule which encodes an amino acid sequence as set forth in SEQ ID NO:4 and/or SEQ ID NO:6; and, (c) a nucleotide sequence which hybridizes under conditions of moderate stringency to the complement of a second nucleic acid molecule as set forth in SEQ ID NO:3 and/or SEQ ID NO:5; and, wherein said nucleic acid molecule encodes an amino acid sequence that has at least about an 80% identity to at least one of the amino acid sequences as set forth in SEQ ID NO:4 and/or SEQ ID NO:6.

A further embodiment of the present invention relates to an isolated or purified nucleic acid molecule encoding a coccidian CKI protein, including but not limited to a CKI protein of the *Eimeria* or *Toxoplasma* genera, wherein the nucleic acid molecule comprises a nucleotide sequence selected from the group consisting of: (a) a nucleotide sequence which encodes an amino acid sequence as set forth in SEQ ID NO:2 and/or SEQ ID NO:6; (b) a nucleotide sequence which hybridizes under conditions of moderate to high stringency to the complement of a second nucleic acid molecule which encodes an amino acid sequence as set forth in SEQ ID NO:2 and/or SEQ ID NO6; and, (c) a nucleotide sequence which hybridizes under conditions of moderate stringency to the complement of a second nucleic acid molecule as set forth in SEQ ED NO: 1 and/or SEQ ID NO:5; and, wherein said nucleic acid molecule encodes an amino acid sequence that has at least about an 80% identity to at least one of the amino acid sequences as set forth in SEQ ID NO:2 and/or SEQ ID NO:6.

One embodiment of the present invention relates to an isolated or purified nucleic acid molecule encoding a coccidian CKI protein, including but not limited to a CKI protein of the *Eimeria* or *Toxoplasma* genera, wherein the nucleic acid molecule comprises a nucleotide sequence selected from the group consisting of: (a) a nucleotide sequence which encodes an amino acid sequence as set forth in SEQ ID NO:2; (b) a nucleotide sequence which hybridizes under conditions of moderate to high stringency to the complement of a second nucleic acid molecule which encodes an amino acid sequence as set forth in SEQ ID NO:2; and, (c) a nucleotide sequence which hybridizes under conditions of moderate stringency to the complement of a second nucleic acid molecule as set forth in SEQ ID NO:1; and, wherein said nucleic acid molecule encodes an amino acid sequence that has at least about an 80% identity to at least one of the amino acid sequences as set forth in SEQ ID NO:2.

Another embodiment of the present invention relates to an isolated or purified nucleic acid molecule encoding a coccidian CKI protein, including but not limited to a CKI protein of the *Eimeria* or *Toxoplasma* genera, wherein the nucleic acid molecule comprises a nucleotide sequence selected from the group consisting of: (a) a nucleotide sequence which encodes an amino acid sequence as set forth in SEQ ID NO:4; (b) a nucleotide sequence which hybridizes under conditions of moderate to high stringency to the complement of a second nucleic acid molecule which encodes an amino acid sequence as set forth in SEQ ID NO:4; and, (c) a nucleotide sequence which hybridizes under conditions of moderate stringency to the complement of a second nucleic acid molecule as set forth in SEQ ID NO:3; and, wherein said nucleic acid molecule encodes an amino acid sequence that has at least about an 80% identity to at least one of the amino acid sequences as set forth in SEQ ID NO:4.

A further embodiment of the present invention relates to an isolated or purified nucleic acid molecule encoding a coccidian CKI protein, including but not limited to a CKI protein of the *Eimeria* or *Toxoplasma* genera, wherein the nucleic acid molecule comprises a nucleotide sequence selected from the group consisting of: (a) a nucleotide sequence which encodes an amino acid sequence as set forth in SEQ ID NO:6; (b) a nucleotide sequence which hybridizes under conditions of moderate to high stringency to the complement of a second nucleic acid molecule which encodes an amino acid sequence as set forth in SEQ ID NO:6; and, (c) a nucleotide sequence which hybridizes under conditions of moderate stringency to the complement of a second nucleic acid molecule as set forth in SEQ ID NO:5; and, wherein said nucleic acid molecule encodes an amino acid sequence that has at least about an 80% identity to at least one of the amino acid sequences as set forth in SEQ ID NO:6.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3; and the temperature is at least about 30° C. for short probes, primers or oligonucleotides (e.g., 10 to 50 nucleotides) and at least about 60° C. for longer probes, primers and oligonucleotides. Stringent conditions may also be achieved with the addition of destabilizing agents, such as formamide. For additional details and explanation of stringency of hybridization reactions, see Ausubel et al., *Current Protocols in Molecular Biology*, Wiley Interscience Publishers, (1995).

Conditions of "high stringency," as defined herein, may be identified by those that: (1) employ low ionic strength and high temperature for washing, for example 0.015 M sodium chloride/0.0015 M sodium citrate, 0.1% sodium dodecyl sulfate (SDS) at 50° C.; (2) employ during hybridization a denaturing agent, such as formamide, for example, 50% (v/v) formamide with 0.1% bovine serum albumin (BSA), 0.1% Ficoll, 0.1% polyvinylpyrrolidone, 50 mM sodium phosphate buffer at pH 6.5 with 750 mM sodium chloride/750 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. "Moderate stringency" conditions may be identified as described by Sambrook et al., *Molecular Cloning: A Laboratory Manual*, New York: Cold Spring Harbor Press, 1989, and include the use of washing solution and hybridization conditions (e.g., temperature, ionic strength and percent SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like. An example of progressively higher stringency conditions is as follows: 2×SSC/ 0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically The present invention also relates to recombinant vectors and recombinant host, both prokaryotic and eukaryotic, which contain the substantially purified nucleic acid molecules disclosed throughout this specification.

The present invention relates to purified forms of coccidian casein kinase I proteins substantially free from other proteins, including but not limited to coccidian CKI proteins of the *Eimeria* or *Toxoplasma* genera. One aspect of the present invention relates to substantially purified *Eimeria* CKI proteins isolated from species of *Eimeria* that infect poultry, including but not limited to *E. tenella* and *E. necatrix* which are highly pathogenic in domestic chickens. Another aspect of the present invention relates to substantially purified *Toxoplasma* CKI proteins isolated from the species *Toxoplasma gondii*.

The present invention further relates to substantially purified coccidian CKI proteins which comprise or consist of an amino acid sequence selected from the group consisting of SEQ ID NO:2, SEQ ID NO:4 and SEQ ID NO:6.

One embodiment of the present invention relates to a substantially purified coccidian CKI protein comprising or consisting of the amino acid sequence disclosed in FIG. 4 as SEQ ID NO:2. The amino acid sequence set forth in SEQ ID NO:2 represents the alpha ('α') isoform of a novel coccidian CKI identified from *Eimeria tenella*, designated EtCKIα. Another embodiment of the present invention relates to a substantially purified coccidian CKI protein comprising or consisting of the amino acid sequence disclosed in FIG. 4 as SEQ ID NO:4 or SEQ ID NO:6. The amino acid sequences set forth in SEQ ID NO:4 and SEQ ID NO:6 represent the alpha ('α') and beta ('β') isoforms of novel coccidian CKI identified from *Toxoplasma gondii*, designated TgCKIα and TgCKIβ, respectively.

A preferred aspect of the present invention is disclosed in FIG. 4 as SEQ ID NO:2, a coccidian amino acid sequence representing the *Eimeria tenella* casein kinase I alpha isoform, EtCKIα, and disclosed as follows:

```
                                                                 (SEQ ID NO:2)
  1 MDVRVGGKYR LGRKIGSGSF GDIYLGTNIS TGDEVAIKLE SVRSRHPQLI YESKLYKILT

61 GGIGIPTLYW YGIEGDYNVM IIELLGPSLE DLFSICNRKL SLKTVLMLAD QMLNRIEFVH

121 SRHFIHRDIK PDNFLIGRGK KMSIVFAIDF GLAKKYRDPR TQSHIPYREG KNLTGTARYA

181 SVNTHLGIEQ SRRDDLEALG YVLMYFNRGS LPWQGLKATT KKDKYDKIME KKMSTPIEVL

241 CKQFPFEFIT YLNYCRSLRF EDRPDYSYLR RLFKDLFFRE GYQYDFIFDW TFLHAERERE

301 RQRRSMVNQG AESGNQWRRD ASGRDPLGRL PQLEP.
```

Another preferred aspect of the present invention is disclosed in FIG. 4 as SEQ ID NO:4, a coccidian amino acid sequence representing the *Toxoplasma gondii* casein kinase I alpha isoform, TgCKIα, and disclosed as follows:

```
                                                                 (SEQ ID NO:4)
  1 MEVRVGGKYR LGRKIGSGSF GDIYIGANIL TGDEVAIKLE SIKSKHPQLL YESKLYKLLA

61 GGIGIPMVHW YGIEGDYNVM VIDLLGPSLE DLFSICNRKL SLKTVLMLAD QMLNRIEFVH

121 SKNFIHRDIK PDNFLIGRGK KMSVVYIIDF GLAKKYRDPK TQQHIPYREG KNLTGTARYA

181 SINTHLGIEQ SRRDDLEALG YVLMYFNRGS LPWQGLKATT KKDKYDKIME KKMSTPIEIL

241 CKHFPFEFIT YLNYCRSLRF EDRPDYAYLR RLFKDLFFRE GYQYDFIFDW TFINTEKDRA

301 SRRSQQVYVE DNRQVEENQN ELPM.
```

Another preferred aspect of the present invention is disclosed in FIG. 4 as SEQ ID NO:6, a coccidian amino acid sequence representing the *Toxoplasma gondii* casein kinase I beta isoform, TgCKIβ, and disclosed as follows:

```
                                                                 (SEQ ID NO:6)
  1 MAHHQDTRNH TGVGPSSSIP LKDLKIAGVW KIGRKIGSGS FGDIYKGLNS QTGQEVALKV

61 ESTKAKHPQL LYEYKLLKHL QGGTGIAQVF CCETAGDHNI MAMELLGPSL EDVFNLCNRT
```

-continued

```
121 FSLKTILLLA DQFLQRVEYI HSKNFIHRDI KPDNFLLGGA GNQNTIYVID FGLAKKFRDP

181 KTHQHIPYRE NKNLTGTARY ASISAHLGSE QSRRDDLEAV GYVLMYFCRG GTLPWQGIKA

241 NTKQEKYHKI MEKKMSTPVE VLCKGYPSEF ATYLHYCRSL RFEDRPDYAY LKRLFRDLYI

301 KEGYDDSDRE FDWTVKLSSR SLGPPSSRAQ HVLLSQDTRT RGKRETDRPV AARSGDRERG

361 IHFSNGNVGN PSMATNPGGL SVMVHERTSL VDQGDRGSRE TSTRKEDAKD GRWPGGRFSC

421 LPLLCRRSPT KA.
```

The present invention further relates to a substantially purified coccidian CKI protein, including but not limited to a CKI protein of the *Eimeria* or *Toxoplasma* genera, said protein comprising at least about 80% amino acid sequence identity with an amino acid sequence selected from the group consisting of SEQ ID NO:2, SEQ ID NO:4 and SEQ ID NO:6.

Another embodiment of the present invention relates to a substantially purified coccidian CKI protein, including but not limited to a CKI protein of the *Eimeria* or *Toxoplasma* genera, said protein comprising at least about 80% amino acid sequence identity with an amino acid sequence selected from the group consisting of SEQ WD NO:2 and SEQ ID NO:4.

The present invention also relates to a substantially purified coccidian CKI protein, including but not limited to a CKI protein of the *Eimeria* or *Toxoplasma* genera, said protein comprising at least about 80% amino acid sequence identity with an amino acid sequence selected from the group consisting of SEQ ID NO:4 and SEQ ID NO:6.

The present invention further relates to a substantially purified coccidian CKI protein, including but not limited to a CKI protein of the *Eimeria* or *Toxoplasma* genera, said protein comprising at least about 80% amino acid sequence identity with an amino acid sequence as set forth in SEQ ID NO:2.

The present invention still further relates to a substantially purified coccidian CKI protein, including but not limited to a CKI protein of the *Eimeria* or *Toxoplasma* genera, said protein comprising at least about 80% amino acid sequence identity with an amino acid sequence as set forth in SEQ ID NO:4.

The present invention also relates to a substantially purified coccidian CKI protein, including but not limited to a CKI protein of the *Eimeria* or *Toxoplasma* genera, said protein comprising at least about 80% amino acid sequence identity with an amino acid sequence as set forth in SEQ ID NO:6.

The present invention also relates to biologically active fragments and/or mutants of the coccidian CKI proteins as initially set forth as SEQ ID NO:2, SEQ ID NO:4 and SEQ ID NO:6, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for agonists and/or antagonists for CKI function.

A preferred aspect of the present invention relates to a substantially purified, fully processed (including any proteolytic processing, glycosylation and/or phosphorylation) and mature coccidian CKI protein obtained from a recombinant host cell (both prokaryotic and eukaryotic, as well as both stably and transiently transformed/transfected cells) containing a DNA expression vector comprising a nucleotide sequence as set forth in SEQ ID NOs:1, 3 and/or 5, and expresses the *Eimeria* or *Toxoplasma* CKI precursor or mature form of the respective protein. It is especially preferred that the recombinant host cells be a eukaryotic host cell, including but not limited to a mammalian or insect cell line.

The present invention also relates to subcellular membrane fractions and cell lysates of the recombinant host cells (both prokaryotic and eukaryotic, as well as both stably and transiently transformed/transfected cells) comprising the nucleic acid molecules of the present invention, including but not limited to the *Eimeria* and *Toxoplasma* CKI cDNA molecules disclosed herein. For a coccidian CKI protein that localizes to a membranous region of the recombinant cells in which it is expressed, the subcellular membrane fractions can comprise wild-type or mutant forms of said coccidian CKI protein, often at levels substantially above wild-type levels and hence will be useful in various assays described throughout this specification. For a coccidian CKI protein that localizes to the cytosol of the recombinant cells in which is it expressed, a cell lysate fraction of said cells can comprise wild-type or mutant forms of said coccidian CKI protein. Again, the expression levels of said CKI protein can be substantially above wild-type levels and thus can be useful in various assays described herein.

Therefore, the present invention relates to methods of expressing the coccidian CKI genes and biological equivalents disclosed herein, assays employing these gene products, cells expressing these gene products, and agonistic and/or antagonistic compounds identified through the use of these coccidian CKI genes and expressed coccidian CKI protein, including, but not limited to one or more modulators of *Eimeria tenella* CKIα, *Toxoplasma gondii* CKIα and *Toxoplasma gondii* CKIβ. These modulators may act through many different mechanisms, including but not limited to direct contact with the kinase domain of the coccidian CKI proteins or by preventing the binding of the target protein substrate to the coccidian CKI. Said modulators may either prevent or promote receptor activity.

As used herein, a "biologically active equivalent" or "functional derivative" of a wild-type coccidian CKI, including but not limited to a CKI protein of the *Eimeria* or *Toxoplasma* genera, possesses a biological activity that is substantially similar to the biological activity of the wild-type coccidian CKI. The term "functional derivative" is intended to include the "fragments," "mutants," "variants," "degenerate variants," "analogs," "homologues" or "chemical derivatives" of the wild-type coccidian CKI protein. The term "fragment" is meant to refer to any polypeptide subset of wild-type coccidian CKI. The term "mutant" is meant to refer to a molecule that may be substantially similar to the wild-type form but possesses distinguishing biological characteristics. Such altered characteristics include but are in no way limited to altered substrate binding, altered substrate affinity and altered sensitivity to chemical compounds affecting biological activity of the coccidian CKI or coccidian CKI functional derivative. The term "variant" is meant to refer to a molecule substantially similar in structure and function to either the entire wild-type protein or to a fragment thereof. A molecule is "substantially similar" to a wild-type coccidian CKI-like protein if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the full-length coccidian CKI protein or to a biologically active fragment thereof.

Any of a variety of procedures may be used to clone a coccidian CKI of the present invention. These methods include, but are not limited to, (1) a RACE PCR cloning technique (Frohman, et al., 1988, *Proc. Natl. Acad. Sci. USA* 85: 8998-9002). 5' and/or 3' RACE may be performed to generate a full-length cDNA sequence. This strategy involves using gene-specific oligonucleotide primers for PCR amplification of coccidian CKI cDNA. These gene-specific primers are designed through identification of an expressed sequence tag ("EST") nucleotide sequence which has been identified by searching any number of publicly available nucleic acid and protein databases; (2) direct functional expression of the coccidian CKI cDNA following the construction of a coccidian CKI-containing cDNA library in an appropriate expression vector system; (3) screening a coccidian CKI-containing cDNA library constructed in a bacteriophage or plasmid shuttle vector with a labeled degenerate oligonucleotide probe designed from the amino acid sequence of the coccidian CKI protein; (4) screening a coccidian CKI-containing cDNA library constructed in a bacteriophage or plasmid shuttle vector with a partial cDNA encoding the coccidian CKI protein. This partial cDNA is obtained by the specific PCR amplification of coccidian CKI DNA fragments through the design of degenerate oligonucleotide primers from the amino acid sequence known for other kinases which are related to the coccidian CKI protein; (5) screening a coccidian CKI-containing cDNA library constructed in a bacteriophage or plasmid shuttle vector with a partial cDNA encoding, for example, an *Eimeria* or *Toxoplasma* CKI protein. This strategy may also involve using gene-specific oligonucleotide primers for PCR amplification of coccidian CKI cDNA identified as an EST as described above; or (6) designing 5' and 3' gene specific oligonucleotides using SEQ ID NOs:1, 3 or 5 as a template so that either the full-length cDNAs may be generated by known RACE techniques, or a portion of the coding regions may be generated by these same known RACE techniques to generate and isolate a portion of the coding regions to use as probes to screen one of numerous types of cDNA and/or genomic libraries in order to isolate a full-length version of the nucleotide sequence encoding coccidian CKI.

It is readily apparent to those skilled in the art that other types of libraries, as well as libraries constructed from other cell types-or species types, may be useful for isolating a coccidian CKI-encoding DNA, including but not limited to a CKI-encoding DNA from the *Eimeria* or *Toxoplasma* genus, or a coccidian CKI homologue. Other types of libraries include, but are not limited to, cDNA libraries derived from cells or cell lines other than coccidian cells or tissue such as a vertebrate host which may contain coccidian CKI-encoding DNA. Additionally, a coccidian CKI genes and homologues may be isolated by oligonucleotide- or polynucleotide-based hybridization screening of a coccidian genomic library. It is readily apparent to those skilled in the art that suitable cDNA libraries may be prepared from cells or cell lines which have CKI activity. Additionally, since the coccidian protozoa have multiple infectious stages (e.g., sporozoites, merozoites, schizonts, oocysts for *Eimeria* sp.; sporozoites, tachyzoites, bradyzoites and oocysts for *Toxoplasma*), a cDNA library from which to clone the coccidian CKI genes of the present invention can be generated from any of these stages of the protozoan life-cycle. The selection of cells or cell lines for use in preparing a cDNA library to isolate a cDNA encoding a coccidian CKI may be done by first measuring cell-associated CKI activity using any known assay available for such a purpose.

Preparation of cDNA libraries can be performed by standard techniques well known in the art. Well known cDNA library construction techniques can be found for example, in Sambrook et al., 1989, supra. Complementary DNA libraries may also be obtained from numerous commercial sources, including but not limited to Clontech Laboratories, Inc. and Stratagene.

It is also readily apparent to those skilled in the art that DNA encoding coccidian CKI may also be isolated from a suitable genomic DNA library. Construction of genomic DNA libraries can be performed by standard techniques well known in the art. Well known genomic DNA library construction techniques can be found in Sambrook, et al., supra.

In order to clone a coccidian CKI genes of the present invention by one of the preferred methods, the amino acid or DNA sequences of a coccidian CKI, including but not limited to an *Eimeria* or *Toxoplasma* CKI protein, or a homologous protein, may be necessary. To accomplish this, the CKI protein or a protein homologue may be purified and partial amino acid sequence determined by automated sequenators. It is not necessary to determine the entire amino acid sequence, but the linear sequence of two regions of six (6) to eight (8) amino acids can be determined for PCR amplification of a partial coccidian CKI DNA fragment. Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the *T. gondii* and *E. tenella* CKI sequences disclosed herein, but others in the set will be capable of hybridizing to these coccidian CKI DNAs even in the presence of DNA oligonucleotides with mismatches. The mismatched DNA oligonucleotides may still sufficiently hybridize to the specific coccidian CKI DNA to permit identification and isolation of coccidian CKI encoding DNA. Alternatively, the nucleotide sequence of a region of an expressed sequence may be identified by searching one or more available genomic databases. Gene-specific primers may be used to perform PCR amplification of a cDNA of interest from either a cDNA library or a population of cDNAs. As noted above, the appropriate nucleotide sequence for use in a PCR-based method may be obtained from SEQ ID NOs:1, 3 or 5, either for the purpose of isolating overlapping 5' and 3' RACE products for generation of a full-length sequence coding for coccidian CKI, or to isolate a portion of the nucleotide sequence coding for coccidian CKI for use as a probe to screen one or more cDNA- or genomic-based libraries to isolate a full-length sequence encoding coccidian CKI or coccidian CKI-like proteins.

It is also readily apparent to those skilled in the art that DNA encoding coccidian CKI, including but not limited to CKI from the *Eimeria* or *Toxoplasma* genera, may be synthetically generated. Many different methods are used for assembling and generating synthetic genes are known in the art. For example in one such method, a series of sequentially overlapping oligonucleotides are synthesized. The oligonucleotides anneal to form a double stranded DNA fragment containing nicks on both strands. DNA-ligase, an enzyme that catalyses the formation of phosphodiester bonds between the 5'-phosphate of one double-strand oligonucleotide fragment and the 3'-hydroxyl terminus on another adjacent double-strand oligonucleotide, is used to seal the nicks. Synthetic genes can also be made using the template-directed and primer-dependent 5'- to 3'-synthesis capabilities of the large subunit of the enzyme DNA-Polymerase I (Klenow fragment). The polymerase uses deoxynucleoside-triphosphates to fill in gaps once end annealing of the long oligonucleotides occurs. Any nick in the resulting double-stranded DNA is sealed by DNA ligase. Finally, very long oligonucleotide chains can be synthesized so that their 3'-ends overlap upon annealing. A subsequent filling-in reaction using DNA polymerase completes the full-length, double-stranded DNA. A number of companies specialize in generating synthetic genes with a high degree of sequence accuracy including Entelechon GmbH (Regensburg, Germany) and MCLAB (South San Francisco, Calif.).

In an exemplified method, the *Toxoplasma* CKI enzymes of the present invention were identified based on EST sequence information mined from the *Toxoplasma* EST database (http://www.toxodb.org/ToxoDB.shtml; Li, A. L. et al., 2003, *Genome Res.* 13:443-454). Two distinct classes of RT-PCR product were amplified from tachyzoite RNA using PCR primers designed from a segment of overlapping EST clones that showed homology to CKI enzymes of other organisms (GenBank Accession Nos. BM175598 and T62400). The cloned RT-PCR products were used to screen a tachyzoite cDNA library, and cDNAs corresponding to two different CKI genes were identified. Putative open reading frames were assigned based on sequence alignments of previously characterized CKI enzymes (Klimczak, L. J. et al., 1995, *Plant Physiol.* 109:687-696; Barik, S. et al., 1997, supra; Gross, S. D. and Anderson, R. A., 1998, supra; Moreno-Bueno, G. et al., 2000, *Biochem. J.* 349:527-537) and optimal translational start sites were identified. The two cDNAs identified from *T. gondii* have predicted amino acid products of 38 kDa and 49 kDa. Due to its higher degree of homology with *Plasmodium falciparum* CKIα (PfCKIα), the 38 kDa product was designated isoform "α" (TgCKIα), and the larger form isoform "β" (TgCKIβ). TgCKIα shares 68% identity with PfCKIα at the amino acid level; while TgCKIβ shares a 45% identity with the *Plasmodium* protein. The two CKI isoforms from *T. gondii* share 48% identity. An internal amino acid sequence of TgCKIα matches the TgCKI peptide identified in Knockaert et al., 2000, supra. The *Eimeria tenella* homologue of the *T. gondii* CKIα enzyme was cloned by screening a sporozoite cDNA library with a TgCKIα probe under low stringency conditions. Full-length clones encoding a predicted open-reading frame of 39 kDa were identified. Since the CKI isoform identified from *E. tenella* shares 81% identity at the amino acid level with TgCKIα, it was designated isoform "α" (EtCKIα).

Coccidian CKI cDNA, including but not limited to the *E. tenella* and *T. gondii* CKI genes disclosed herein, that are obtained through the methods described above may be recombinantly expressed by molecular cloning into an expression vector (such as pcDNA3.neo, pcDNA3.1, pCR2.1, pBlueBacHis2, pLITMUS28 or pETblue1 vector) containing a suitable promoter and other appropriate transcription regulatory elements, and transferred into prokaryotic or eukaryotic host cells to produce recombinant coccidian CKI. Expression vectors are defined herein as DNA sequences that are required for the transcription of cloned DNA and the translation of their mRNAs in an appropriate host. Such vectors can be used to express eukaryotic DNA in a variety of recombinant host cells such as bacteria, blue green algae, plant cells, protozoan cells, insect cells and mammalian cells. An appropriately constructed expression vector should contain the following: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Methods to determine the coccidian CKI cDNA sequence(s) that yields optimal levels of expressed coccidian CKI protein are well known in the art. Following determination of the coccidian CKI cDNA cassette yielding optimal expression, this coccidian CKI cDNA construct is transferred to a variety of expression vectors (including recombinant viruses), including but not limited to those for mammalian cells, plant cells, insect cells, protozoan cells, oocytes, bacteria and yeast cells. Techniques for such manipulations can be found in Sambrook, et al., supra, and are well known and available to artisans of ordinary skill in the art. Therefore, another aspect of the present invention includes host cells that have been engineered to contain and/or express DNA sequences encoding coccidian CKI. An expression vector containing DNA encoding coccidian CKI protein may be used for expression of coccidian CKI in a recombinant host cell. Such recombinant host cells can be cultured under suitable conditions to produce coccidian CKI or a biologically equivalent form. Expression vectors may include, but are not limited to, cloning vectors, modified cloning vectors, specifically designed plasmids or viruses. Also, a variety of commercially available mammalian, bacterial, fungal cell, and insect cell expression vectors may be used to express recombinant coccidian CKI in the respective cell types, in addition to those expression vectors described in Donald, R. G. K. and Liberator, P. A., 2002 (*Mol. Biochem. Parasitol.* 120:165-175) and Donald, R. G. K. et al., 2002 (*Eukaryotic Cell.* 1:317-328).

Recombinant host cells may be prokaryotic or eukaryotic, including but not limited to, bacteria such as *E. coli*, fungal cells such as yeast, mammalian cells including, but not limited to, cell lines of bovine, porcine, monkey, and rodent origin; and insect cells. Protozoan host cells may also be used for transgenic expression of the CKI proteins disclosed herein, including but not limited to *Toxoplasma* and *Leishmanial* expression systems. Additionally, it may be beneficial that an inducible expression system (e.g., tetracycline on/off system) be implemented for expression of said proteins.

The expression vector may be introduced into host cells via any one of a number of techniques including but not limited to transformation, transfection, protoplast fusion, and electroporation. The expression vector-containing cells are individually analyzed to determine whether they produce coccidian CKI protein. Identification of coccidian CKI expressing cells may be done by several means, including but not limited to immunological reactivity with anti-coccidian CKI antibodies, labeled ligand binding and the presence of host cell-associated coccidian CKI activity.

Expression of coccidian CKI DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

Levels of coccidian CKI in host cells is quantified by a variety of techniques, including but not limited to immunoaffinity and/or ligand affinity techniques. CKI-specific affinity beads or CKI-specific antibodies are used to isolate $^{35}$S-methionine labeled or unlabelled CKI. Labeled CKI protein is analyzed by SDS-PAGE. Unlabelled CKI protein is detected by Western blotting, ELISA or RIA assays employing either CKI protein specific antibodies and/or antiphosphothreonine/antiphosphoserine antibodies.

Following expression of CKI in a host cell, CKI protein may be recovered to provide CKI protein in active form. Several CKI protein purification procedures are available and suitable for use. Recombinant CKI protein may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography.

In addition, recombinant CKI protein can be separated from other cellular proteins by use of an immunoaffinity column made with monoclonal or polyclonal antibodies specific for full-length CKI protein or polypeptide fragments of CKI protein. Additionally, polyclonal or monoclonal antibodies may be raised against a synthetic peptide (usually from about 9 to about 25 amino acids in length) from a portion of the proteins as disclosed in SEQ ID NOs:2, 4 or 6. Monospecific antibodies to coccidian CKI are purified from mammalian antisera containing antibodies reactive against coccidian CKI or are prepared as monoclonal antibodies reactive with coccidian CKI using the technique of Kohler and Milstein (1975, *Nature* 256: 495-497).

Monospecific antibody as used herein is defined as a single antibody species or multiple antibody species with homogenous binding characteristics for coccidian CKI. Homogenous binding, as used herein, refers to the ability of the antibody species to bind to a specific antigen or epitope, such as those associated with coccidian CKI, as described above. Coccidian CKI-specific antibodies are raised by immunizing animals such as mice, guinea pigs, rabbits, goats, horses and the like, with an appropriate concentration of coccidian CKI protein or a synthetic peptide generated from a portion of a coccidian CKI with or without an immune adjuvant. Preimmune serum is collected prior to the first immunization. Each animal receives between about 0.1 mg and about 1000 mg of coccidian CKI protein associated with an acceptable immune adjuvant, including but not limited to Freund's complete, Freund's incomplete, alum-precipitate, water in oil emulsion containing *Corynebacterium parvum* and tRNA. The initial immunization consists of coccidian CKI protein or a peptide fragment thereof in, preferably, Freund's complete adjuvant at multiple sites either subcutaneously (SC), intraperitoneally (IP) or both. The animals may or may not receive booster injections following the initial immunization depending on determination of antibody titer. At about 7 days after each booster immunization, or about weekly after a single immunization, the animals are bled, serum collected, and aliquots stored at about −20° C.

Monoclonal antibodies (mAb) reactive with coccidian CKI protein are prepared by immunizing inbred mice, preferably Balb/c, with coccidian CKI protein. The mice are immunized by the IP or SC route with about 1 mg to about 100 mg, preferably about 10 mg, of coccidian CKI protein in about 0.5 ml buffer or saline incorporated in an equal volume of an acceptable adjuvant, as discussed above. Immunized mice are given one or more booster immunizations by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. The antibody producing cells and myeloma cells are fused in polyethylene glycol. Fused hybridoma cells are selected by growth in hypoxanthine, thymidine and aminopterin supplemented Dulbecco's Modified Eagles Medium (DMEM) by procedures known in the art. Supernatant fluids are collected form growth positive wells and are screened for antibody production by an immunoassay such as solid phase immunoradioassay (SPIRA) using coccidian CKI as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in *Tissue Culture Methods and Applications*, Kruse and Paterson, Eds., Academic Press.

Monoclonal antibodies are produced in vivo by injection of pristine primed Balb/c mice, approximately 0.5 ml per mouse, with about $2\times10^6$ to about $6\times10^6$ hybridoma cells about 4 days after priming. Ascites fluid is collected at approximately 8-12 days after cell transfer and the monoclonal antibodies are purified by techniques known in the art.

In vitro production of anti-coccidian CKI mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays known in the art. Similar assays are used to detect the presence of coccidian CKI in fluids or tissue and cell extracts.

It is readily apparent to those skilled in the art that the above described methods for producing monospecific antibodies may be utilized to produce antibodies specific for a coccidian CKI peptide fragments, or a respective a full-length coccidian CKI.

The coccidian CKI proteins of the present invention are suitable for use in an assay procedure for the identification of compounds which modulate CKI activity. A CKI-containing fusion construct, such as a FLAG-epitope tagged CKI fusion protein as discussed within this specification, is useful to measure CKI activity. Kinase activity can be measured, for example, using a modified version of the casein kinase I assay described by Donald et al., R. G. K. et al., 2002, supra, and as outlined in Example 2. Casein kinase activity can be assayed using 96-well phosphocellulose plates to capture $^{33}$P-phosphorylated peptide or casein substrates. Kinase reactions can be carried out in 40 µl volumes containing 25 mM Hepes pH 7.4, 10 mM MgCl$_2$, 20 mM β-glycerophosphate, 1 mM DTT, 250 µM substrate, 1 mg/ml BSA, 2 µM ATP and 0.01 µM[γ-$^{33}$P]ATP. The reaction is initiated by addition of enzyme and then incubated at room temperature for 60 minutes. A variety of commercially available peptides substrates can be use, as described in Example 2.

The coccidian CKI proteins of the present invention, including but not limited to CKI proteins of the *Eimeria* and *Toxoplasma* genera, may be obtained from both native and recombinant sources (as a full-length protein, biologically active protein fragment, or fusion construction) for use in assay procedures to identify coccidian CKI modulators. Modulating CKI includes the inhibition or activation of the kinase, representing antagonists or agonists, respectively. In general, an assay procedure to identify coccidian CKI modulators will contain at least a functional domain of a coccidian CKI and a test compound or sample which contains a putative CKI kinase agonist or antagonist. The test compound or sample may be tested directly on, for example, purified CKI or an epitope tagged-CKI fusion, subcellular fractions of CKI-producing cells containing CKI (native or recombinant), whole cells expressing coccidian CKI (native or recombinant), and/or CKI protein fragments and respective deletion fragments. The test compound or sample may be added to CKI in the presence or absence of a known CKI substrate, including but not limited to casein. The modulating activity of the test compound or sample may be determined by, for example, analyzing the ability of the test compound or sample to bind to CKI, activate the protein, inhibit the protein, inhibit or enhance the binding of other compounds to coccidian CKI, or modifying kinase activity.

The present invention is also directed to methods for screening for compounds which modulate the expression of DNA or RNA encoding a coccidian CKI protein, including but not limited to a CKI protein of the *Eimeria* or *Toxoplasma* genera. Compounds which modulate these activities may be DNA, RNA, peptides, proteins, or non-proteinaceous organic molecules. Compounds may modulate CKI protein by increasing or attenuating the expression of DNA or RNA encoding the protein or the function of coccidian CKI. Compounds that modulate the expression of DNA or RNA encoding coccidian CKI or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample. Kits containing at CKI, antibodies to coccidian CKI, or modified coccidian CKI may be prepared by known methods for such uses.

The DNA molecules, RNA molecules, recombinant proteins and antibodies of the present invention may be used to screen and measure levels of coccidian CKI. The recombinant proteins, DNA molecules, RNA molecules and antibodies lend themselves to the formulation of kits suitable for the detection and typing of coccidian CKI. Such a kit would comprise a compartmentalized carrier suitable to hold in close confinement at least one container. The carrier would further comprise reagents such as recombinant CKI or anti-CKI antibodies suitable for detecting coccidian CKI. The carrier may also contain a means for detection such as labeled antigen or enzyme substrates or the like.

Pharmaceutically useful compositions comprising modulators of coccidian CKI may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, modified coccidian CKI, or either CKI agonists or antagonists including serine of threonine kinase activators or inhibitors.

Therapeutic or diagnostic compositions of the invention are administered to an animal, including but not limited to humans and poultry, in amounts sufficient to treat or diagnose disorders. The effective amount may vary according to a variety of factors such as the animal's condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

All publications mentioned herein are incorporated by reference for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying figures, it is to be understood that the invention is not limited to those precise embodiments, and that various changes and modifications may be effected therein by one skilled in the art without departing from the scope or spirit of the invention as defined in the appended claims.

The following examples are provided to illustrate the present invention without, however, limiting the same hereto.

EXAMPLE 1

Identification of cDNAs Encoding Coccidian Parasite Casein Kinase I

Cloning of *Toxoplasma gondii* CKIα and CKIβ-BLAST searching of the *Toxoplasma* EST database (http://www.toxodb.org/ToxoDB.shtml) identified a pair of overlapping ESTs (GenBank BM175598 and T62400) with homology to a CKI consensus sequence derived from a ClustalW alignment of CKI enzymes characterized from a variety of organisms (AlignX, Vector NTI suite). The *Toxoplasma* EST sequences identified are listed below:

BM175598

(SEQ ID NO:7)
AGAATTTCATTCACAGAGATATCAAACCAGATAACTTTCTTCTCGGCGGT

GCCGGCAATCAAAACACGATCTACGTGATCGACTTCGGCCTGGCGAAGAA

GTTTCGCGATCCGAAAACGCACCAACATATTCCGTACAGAGAAAACAAGA

ATCTCACGGGAACGGCGCGCTACGCGTCCATCAGTGCGCATCTGTGTTCC

GAGCAGAGTCGCCGAGATGACCTCGAAGCAGTCGGCTACGTTCTCATGTA

CTTCTGTCGAGGAGGCACGCTGCCTTGGCAGGGCATCAAAGCGAATACCA

AACAGGAGAAGTACCACAAGATCATGGAGAAGAAGATGTCGACGCCCGTC

GAGGTGCTATGCAAGGGATATCCAAGCGAATTTGCCACATACTTGCACTA

CTGCCGCTCCTTGCGATTCGAGGACCGACCGGACTACGCCTACCTCAAGC

GACTCTTTCGAGATCTCTACATCAAAGAGGGCTACGATGACAGTGACCGC

GAATTCGACTGGACAGTGAAACTTTCGTCGCGCAGTCTCGGAC.

T62400

-continued (SEQ ID NO:8)
GATATCCAAGCGAATTTGCCACATACTTGCACTACTGCCGCTCCTTGCA

TTCGAGGACCGACCGGACTACGCCTACCTCAAGCGACTCTTTCGAGATCT

CTACATCAAAGAGGGCTACGATGACAGTGACCGCGAATTCGACTGGACAG

TGAAACTTTCGTCGCGCAGTCTCGGACCGCCAAGCAGTCGAGCGCAACAT

GTTTTACTGAGTCAAGACACCCGAACGCGAGGGAAGCGGGAGACAGATCG

ACCTGTCGCTGTGCGGAGTGGCGACCGCGAACGAGGAATCCATTTCAGCA

ACGGGAACGTGGGCAATCCCTCCGATGGCAACGAACCCCCG.

A series of nested PCR primers was designed and used to amplify cDNA fragments from tachyzoite RNA by RT-PCR. RNA was prepared with an Oligo (dT)$_{25}$ Dynabeads® kit (Dynal; Lake Success, N.Y.) and a first-strand cDNA pool synthesized with superscript II (Invitrogen; Carlsbad, Calif.). PCR products were cloned with a TA cloning kit (Promega; Madison, Wis.) and sequenced. Most of the PCR products obtained corresponded to the original EST sequence. However, one of the three sets of PCR primer pairs used, GATAT-CAAACCAGATAACTTTCTTCTCGGC (SEQ ID NO:9) and CAAGGAGCGGCAGTAGTGCAAGT (SEQ ID NO:10), also amplified a second class of cDNA product which showed greater homology to the CKI-α isoform of *Plasmodium falciparum* (Barik, S. et al., 1997, supra). The two distinct cDNA fragments were used separately to probe a tachyzoite cDNA library (#1896, NIH AIDS Research and Reference Reagent Program). Putative open reading frames were assigned based on sequence alignments of previously characterized CKI enzymes (Klimczak, L. J. et al., 1995, supra; Barik et al, 1997, supra; Gross and Anderson, 1998, supra; Moreno-Bueno, G. et al., 2000, supra), and the presence of an optimal nucleotide context surrounding potential translational start sites was identified (Seeber, F., 1997, *Parasitol. Res.* 83:309-311). Corresponding full-length clones were obtained and designated "α" or "β" based on their relative homology to malaria isoform PfCKIα. At least four different full-length clones with 5' untranslated nucleotide sequences extending beyond the predicted start site were obtained for each isoform. No cDNAs corresponding to potentially functional splice variants were detected. Since corresponding TgCKI "α" or "β" genomic contigs identified in the *Toxoplasma* genome database do not overlap, the genes appear to map to separate loci.

Cloning of *Eimeria tenella* CKIα—The *E. tenella* homologue of the *T. gondii* CKI alpha enzyme was cloned by screening a sporozoite cDNA library with a TgCKIα probe under low stringency conditions (plaque lifts hybridized in 30% formamide and washed with 5×SSPE, 0.1% SDS at 42° C.). The cDNA library was generated from polyA+RNA purified from *Eimeria* sporozoites using a standard lambda ZAP cloning kit and packaging reagents (Stratagene; La Jolla, Calif.). The TgCKIα probe, corresponding to the TgCKIα open reading frame, was generated by PCR using the following primer set:

(SEQ ID NO:24)
ATGGACTACAAAGACGATGACGACAAGGAGGTCAGGGTCGGAGGCAAGTA
CCGAC
and (SEQ ID NO:25)
CGGTCTAGATCAGAGGGAGACGCGCGTCCTGACC.

Results—Two *T. gondii* cDNAs encoding CKI isoforms have been identified, TgCKIα (FIG. 2; SEQ ID NO:3) and TgCKIβ (FIG. 3; SEQ ID NO:5). These cDNAs encode protein products with predicted molecular weights of 38 kDa (FIG. 4; SEQ ID NO:4) and 49 kDa (FIG. 4, SEQ ID NO:6), respectively. Due to its higher degree of homology with the *Plasmodium falciparum* CKIα isoform (68% identify, FIG. 5), the smaller protein was designated isoform "α" (TgCKIα). An internal amino acid sequence of this isoform (shown in FIG. 4) matches a TgCKI peptide that was identified by microsequencing of a 38 kDa protein with strong affinity for an immobilized CDK inhibitor (purvalanol B) matrix (Knockaert, M. et al., 2000, *Chem. Biol.* 7:411-422). CKI isoforms from *Plasmodium falciparum* (PfCKIα), *Leishmania mexicana* (LmCKI-2) and *Trypanosoma cruzi* (TcCKI-1) were also found tightly associated with this matrix (identified peptides also highlighted), and their sequences are included for comparison in FIG. 4. Examination of the percentage identity matrix derived from pairwise sequence alignments (FIG. 5) reveals that TgCKIα shares a greater degree of identity with these parasite CKI orthologues than does the larger *T. gondii* isoform. A cDNA encoding the homologue of TgCKIα has been identified from the coccidia *Eimeria tenella*, EtCKIα (FIG. 1; SEQ ID NO:1), generating a protein product with a predicted molecular weight of 39 kDa (FIG. 4; SEQ ID NO:2). The EtCKIα enzyme shares 81% identity with the TgCKIα homologue but only 48% identity with the TgCKIβ isoform (FIG. 5).

EXAMPLE 2

Transient Expression of Coccidian Casein Kinase I Isoforms in *T. gondii*

Epitope tagged constructs—N-terminal FLAG epitope tags were appended to TgCKIα and TgCKIβ open reading frames by PCR amplification (KOD polymerase, Novagen; Madison, Wis.). The sense and antisense PCR primers used to amplify the open frames are as follows:

ATGGACTACAAAGACGATGACGACAAGGAGGTCAGGGTCGGAGGCAAGTA

CCGAC (SEQ ID NO: 24) and CGGTCTAGATCAGAGGGAGACGCG

CGTCCTGACC (SEQ ID NO: 25) for TgCKIα; and ATGGACTA

CAAAGACGATGACGACAAGGCGGACCATCAAGACACCCGCAAC (SEQ

ID NO: 26) and CGGTCTAGATCAAAAAAAGAACTTACGCCCACGGC

GT (SEQ ID NO: 27) for TgCKIβ.

The resulting DNA fragments were subcloned into *E. coli* pETblue1 (Novagen). For subcloning into *T. gondii* tubulin-promoter expression vectors (Donald, R. G. K. and Liberator, P. A., 2002, *Mol. Biochem. Parasitol.* 120:165-175), sense primers bearing additional 5' compatible restriction enzyme recognition sites (BamHI and BclI) were used:

GGCGGATCCGAAAATGGACTACAAAGACGATGACGACAAGGAGGTCAGGGT

CGGAGGCAAGTACCGAC (SEQ ID NO: 28) for TgGKIα; and

GGCGTGATCAAAAATGGACTACAAAGACGATGACGACAAGGCGCACCATC

AAGACACCCGCAAC (SEQ ID NO: 29) for TgCKIβ.

Chimeric TgCKIβ-CAT constructs used for the deletion mapping of the TgCKIβ C-terminal domain were made by inserting PCR-amplified TgCKIβ fragments into CAT fusion vector ptubXhoICAT (Donald and Liberator, 2002, supra). PCR fragments bearing successive 3' end truncations were amplified from TgCKIβ cDNA with KOD polymerase and featured flanking BclI and SalI/XhoI sites (5' and 3' ends, respectively) to facilitate directional sub-cloning. The 5' sense primer used to amplify said fragments is as follows: GGCGTGAT-CAAAAATGGACTACAAAGACATGACGA-CAAGGCGCACCATCAAGAC ACCCGCAAC (SEQ ID NO:29). The antisense 3' primers used to amplify said fragments are as follows: GGCCTCGAGGGCCTFCGTCG-GAGAACGCCGACATAACAGTG (SEQ ID NO:30) for the full-length; GGCGTCGACGATGITATGGTCGCCCG-CAGTCTCGCAACA (SEQ ID NO:31) for 3' Δ332; GGCGTCGACGATCTTGTGGTACTTCTC-CTGTCTGGTATTCGCTTTGATGC (SEQ ID NO:32) for 3'Δ182; and GGCCTCGAGCACGTTCCCGTTGCT-GAAATGGATTCCTCGTTC (SEQ ID NO:33) for 3' Δ64 (see also FIG. 7).

The FLAG-epitope tagged EtCKIα open-reading frame was cloned into *E. coli* and *T. gondii* expression vectors using the same strategy as that outlined above for TgCKI enzymes. The following sense and antisense primers were used for PCR amplification and subsequent *E. coli* expression vector cloning: ATGGACTACAAAGACGATGACGACAAG-GACGTCCGTGTGGGGGGTAAGTATCGT G (SEQ ID NO:34) and CGGTCTAGATCACGGATCTAACTGAG-GCAACCGTCCAAGT (SEQ ID NO:35). To facilitate restriction enzyme mediated cloning into the *Toxoplasma* expression vector, the sense primer was modified to contain a 5' flanking BglII site:

(SEQ ID NO:36)
GGCAGATCTGAAAATGGACTACAAAGACGATGACGACAAGGACGTCCGTG

TGGGGGGTAAGTATCGTTTG.

Host cells and parasite cultures—RH strain or RH ΔHXG-PRT strain tachyzoites of *T. gondii* were maintained by serial passage in confluent monolayers of human foreskin fibroblasts ("HFF") as described (Roos, D. S. et al., 1994, *Methods Cell Biol.* 45:27-63). A modified [³H]-uracil uptake assay (Pfefferkorn, E. R. and Pfefferkorn, L. C., 1977, *J. Protozool.* 24:449-453) adapted for use in 96-well scintillation plates (Cytostar-T, Amersham; Piscataway, N.J.) was used to measure parasite growth inhibition. Each well, previously seeded with HFF cells, was inoculated with *T. gondii* tachyzoites ($2\times10^4$) in 200 μl of growth media containing 2 μCi [5,6]-³H-uracil (Perkin-Elmer NEN; Boston, Mass.) and serially diluted compound. Following incubation at 37° C. for 36-48 hours, tritium-incorporation into host cell monolayers was directly counted in a microplate scintillation counter (Micro-Beta, PerkinElmer-Wallac).

Transfection protocol—Tachyzoites were transfected with 100 μg of expression plasmid $_{FLAG}$TgCKIα, $_{FLAG}$TgC KIβ, $_{FLAG}$EtCKIα or vector alone, in triplicate, and inoculated into cultures of HFF cell monolayers (slides or T-25 flasks).

Immunological reagents and techniques—*T. gondii* CKI epitopes used to raise antisera are shown in FIG. 4. A C-terminal cysteine residue was added to each peptide (synthesized by SynPep; Dublin, Calif.) to facilitate coupling to keyhole-limpet-hemocyanin carrier protein (KLH) by maleimide chemistry (immunogen conjugation kit, Pierce; Rockford, Ill.). Antisera was generated against the coupled peptide-KLH immunogen (Covance; Denver, Pa.) and subsequently affinity-purified by peptide affinity chromatography (SulfoLink kit, Pierce). Antisera was similarly prepared against coccidian parasite calmodulin domain like protein kinase (CDPK1) (Kieschnick, H. et al., 2001, *J. Biol. Chem.* 276:12369-12377; Dunn, P. P. et al., 1996, *Parasitology* 113:439-448). Epitopes corresponding to the CDPK1 enzyme orthologue from *Eimeria tenella* were chosen for antisera production: AKDLIRKMLAYVPSMISARD (SEQ ID NO:11) and AVKVISKRQVKQKTDKELLL (SEQ ID NO:12). The resulting affinity purified antisera recognize both the *Toxoplasma* CDPK1 and the *Eimeria* CDPK homologue (not shown).

At 24 hours post-infection, anti-FLAG indirect immunofluorescence analysis ("IPA") was performed. For IFA staining, HFF host cell cultures were grown on Falcon culture slides, infected with parasites and examined 24-36 h later. Infected monolayers were fixed in 3% paraformaldehyde in PBS, permeabilized with 0.25% Triton-X100 (in PBS) and pre-treated with blocking buffer (1% BSA, 5% serum in PBS) before staining. Treated coverslips were examined with a Zeiss Axiovert 35 inverted microscope equipped with a 100 W Hg-vapor lamp and FITC filter. Polyclonal antisera to the bacterial chloramphenicol acetyltransferase (CAT) reporter and FLAG epitope monoclonal antisera were obtained from Sigma (St. Louis, Mo.).

Kinases transiently expressed in *T. gondii* were immunoprecipitated with agarose beads conjugated with monoclonal FLAG antisera ("FLAG-beads") (TgCKI and EtCKI) or protein A-beads (TgCKI-CAT chimeras) and assayed as previously described (Donald and Liberator, 2002, supra).

Western blots were performed as per standard SDS-PAGE techniques, followed by electrophoretic transfer to nitrocellulose. The antiserum used to probe the nitrocellulose blot was the polyclonal antiserum specific for the CKIα-IT epitope which is well conserved among CKI enzymes (see FIG. 4).

Protein kinase assays—Casein kinase activity was assayed essentially as described (Donald, R. G. K. et al., 2002, supra) using 96-well phosphocellulose plates (MAPH-NOB, Millipore; Billerica, Mass.) to capture $^{33}$P-phosphorylated peptide or casein substrates. Kinase reactions were carried out in 40 μl volumes containing 25 mM Hepes, pH 7.4, 10 mM MgCl$_2$, 20 mM β-glycerophosphate, 1 mM DTT, 250 μM substrate, 1 mg/mL BSA, 2 μM ATP, and 0.01 μM [γ-$^{33}$P]ATP (Perkin-Elmer, 3000 Ci/mmol). The reactions were initiated by the addition of enzyme and incubated at room temperature for 60 min. Casein (5% solution), partially dephosphorylated α-casein and β-casein were obtained from Sigma.

A variety of commercially available peptide substrates were evaluated. From Calbiochem (San Diego, Calif.): CKI substrate (RRKDLHDDEEDEAMSITA; SEQ ID NO:13); CKII substrate (RRADDSDDDDD; SEQ ID NO:14); Syntide-2 substrate (PLARTLSVAGLPGKK; SEQ ID NO:15); CaM kinase II substrate (281-291) (MHKNETVECLK; SEQ ID NO:16). From Promega: CKI substrate (DDDEESITRR; SEQ ID NO:17) and kemptide (LRRASLG; SEQ ID NO:18). From New England Biolabs (Beverly, Mass.): CKI phosphopeptide substrate (KRRRALS(p)VASLPGL; SEQ ID NO:19), and CKII substrate (RRREEETEEE; SEQ ID NO:20). PKG assays were performed with kemptide as substrate and 10 μM cGMP. CDPK was assayed with Syntide-2 substrate and in the presence of 100 μM CaCl$_2$.

Results—Plasmid constructs encoding N-terminal FLAG epitope tagged TgCKIα and TgCKIβ open reading frames were transfected into tachyzoites and expression was monitored by indirect immunofluorescence analysis (IFA) following inoculation of parasites onto HFF cell monolayers (FIG. 6A). Uniform staining consistent with cytosolic expression was found in intracellular tachyzoites transfected with the $_{FLAG}$TgCKIα construct. In contrast, the $_{FLAG}$TgCKIβ plasmid yielded a surface membrane-associated staining pattern similar to that observed with plasmids expressing dually acylated forms of PKG (Donald and Liberator, 2002, supra). Flag epitope-tagged EtCKIα constructs were also transiently expressed in *T. gondii* tachyzoites (FIG. 6A). Recombinant $_{FLAG}$EtCKIα displayed a cytosolic expression pattern, similar to recombinant $_{FLAG}$TgCKIα. As expected, Western blotting of immunoprecipitated material with antisera to a conserved internal CKI epitope detected the presence of a 38 kDa protein in transfections with the TgCKIα or the EtCKIα plasmids (FIG. 6C). In the case of the TgCKIβ construct, a 55 kDa band was observed, a mobility somewhat slower than predicted from its 49 kDa mass.

Significant levels of immunoprecipitated CKI activity were detected in transfections with TgCKIα and TgCKIβ plasmids using milk casein as substrate (FIG. 6B). Approximately two-fold higher levels of CKI activity were detected with the TgCKIα plasmid than with the TgCKIβ construct, which in turn was eight-fold above background levels observed in mock transfections (FIG. 6B). Immunoprecipitated casein kinase I activity was also detected in lysates of parasites transfected with the EtCKIα plasmid (FIG. 6B), while no kinase activity was detected in mock-transfected parasites. As observed with TgCKI expression constructs, ectopic expression of EtCKIα was toxic to *T. gondii* tachyzoites. Parasites expressing high levels of recombinant *T. gondii* or *E. tenella* CKI enzyme appeared sick (FIG. 6A).

Figure 7:
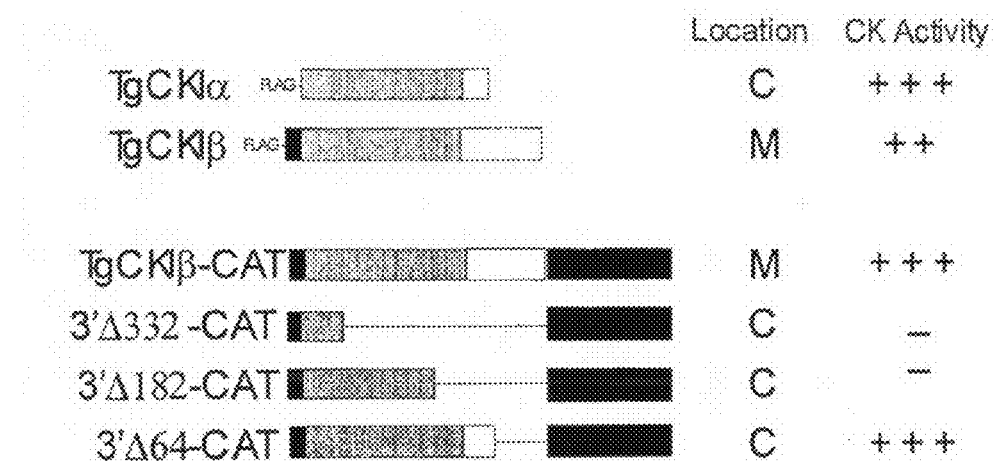
FIG. 7 shows the mapping of the determinant conferring the membrane association of TgCKIβ. TgCKIα, TgCKIβ and TgCKIβ-CAT fusion constructs are shown schematically with a qualitative assessment of subcellular location ('C' for cytosolic; 'M' for membrane) and casein kinase ('CK') activity indicated. Parasites were transiently transfected with plasmids and the IFA and CK activity determined as described in FIG. 6. TgCKIβ-CAT fusion proteins were immunoprecipitated with antisera to the CAT marker (shown in black). Blocks of localized sequence similarity between the α and β isoforms of TgCKI (shaded rectangles) were defined using program AlignX Blocks, a component of Vector-NTI suite (Informax). Deleted portions of the C-terminal domain of TgCKIβ are shown as a thin line.

Due to the lack of obvious N-terminally located acylation signals in TgCKIβ, the location of the determinant responsible for its membrane association was mapped. A TgCKIβ-chloramphenicol acetyl transferase (TgCKIβ-CAT) chimera was constructed that yielded qualitatively similar levels of membrane-associated CKI activity in transiently transfected parasites as the parental $_{FLAG}$TgCKIβ construct (FIG. 7). In this case, kinase activity was immunoprecipitated, and subcellular location determined by IFA with antisera to the CAT reporter. Successive 3' TgCKIβ deletions were made in the chimeric protein and the constructs similarly assessed in transient assays. Deletion of the C-terminal 64 amino acids of TgCKIβ had no effect on CKI activity but abolished its ability to associate with the plasma membrane. This deletion (3'Δ64-CAT) generated the same cytosolic staining observed with the $_{FLAG}$TgCKIα plasmid. Tachyzoites transfected with the chimeric constructs were also subjected to selection in serial passages of 20 μM chloramphenicol. Stable transgenic lines expressing protein chimeras that lack CKI activity were readily obtained, such as those missing the C-terminal 182 or 332 amino acids (3'Δ32-CAT and 3'Δ182-CAT, FIG. 7). In contrast, no stable lines were obtained from transfections with chimeras exhibiting CKI-activity (TgCKIβ-CAT and 3'Δ64-CAT, FIG. 7).

EXAMPLE 3

Purification and Characterization of the Coccidian CKI Isoforms

Purification of recombinant CKI enzymes—*E. coli* strain BL21 Origami™ (Novagen) was transformed with $_{FLAG}$TgCKIα and $_{FLAG}$TgCKIβ expression vectors, and colonies were expanded into 250 mL LB cultures grown at 37° C. Expression was induced with 1 mM IPTG once cultures had reached an OD$_{600nm}$ of 0.3-0.5, and the transformed bacteria were harvested 4-6 hours later. Cell pellets were resuspended in 15 mL of lysis buffer containing protease inhibitors and lysates prepared as described by the supplier (Bugbuster™ reagents, Novagen). The concentration of NaCl in the lysate was adjusted to 0.5 M, and 0.5 mL of FLAG-agarose beads were added (Sigma). The mixture was allowed to rock in a Nutator mixer (Becton-Dickinson; San Jose, Calif.) for 2 hours at 4° C. The slurry was then poured into an empty column and the matrix washed with 50 mL of wash buffer (50 mM Tris-HCl, pH 7.4, 0.5M NaCl, 10% glycerol, 1 mM DTT, 1 mM EDTA). Enzyme was eluted with 5 mL of 0.4 mg/mL FLAG peptide (Sigma) in NaCl-free wash buffer and concentrated with a centrifuge filtration unit (Amicon Ultra®, 10 kDa cut-off, Millipore). Protein was measured with a micro-BCA reagent (Pierce) following a TCA-sodium deoxycholate step to remove residual FLAG peptide (Brown et al., 1989, *Anal. Biochem.* 180:136-139). Using this procedure, and SDS-PAGE analysis, the yield of $_{FLAG}$TgCKIβ was estimated as ~200 μg of enzyme with >90% purity. Purification of $_{FLAG}$TgCKIα was much less efficient with only about 1 μg of ~10% pure enzyme obtained per 250 mL bacterial culture.

Preparations of $_{FLAG}$TgCKIα and $_{FLAG}$TgCKIβ were purified further on a SMART system FPLC 0.1 mL MonoQ anion exchange column (Pharmacia; New York, N.Y.) equilibrated in buffer A (50 mM Hepes, pH 7.4, 10% glycerol, 1 mM DTT) at room temperature. Samples of FLAG-affinity purified enzyme (10-100 μg) were syringe-passed through a 0.22 μm (pore-size) filter before loading on the column. A linear salt gradient was applied (0-500 mM in 3 mL at 100 μl/min) and 100 μl fractions were collected and analyzed by SDS-PAGE and for CKI activity. Fractions with peak activity were retained for further analysis. The degree of purity of the partially purified $_{FLAG}$TgCKIα was estimated by densitometry of silver stained SDS-PAGE gels. A recombinant rat CKIδ enzyme used for control purposes was obtained from New England Biolabs.

Partial purification of native TgCKIα—Parasites from a total of 75× T175 flasks were filtered through 3 μm (pore-size) polycarbonate membranes (Millipore) to remove host cell debris. Following centrifugation in 1 L bottles at 3,000×g for 15 minutes, cell pellets were washed in PBS, the volumes combined and re-centrifuged. The final cell pellet was gently resuspended in 10 mL of lysis buffer which consisted of buffer A supplemented with 1% NP40 and a protease inhibitor cocktail (Complete™; Boehringer, Ingelheim, Germany). The suspension was sonicated with a Branson Sonifier microtip, centrifuged at 100,000×g (30 min at 4° C.), and the supernatant passed through a 0.22 μm filter (Millipore). Approximately 9 mL was loaded onto a LKB FPLC System 5-mL HiTrapQ anion-exchange column (Pharmacia) and run at 4° C. A segmented NaCl gradient was applied (0-0.2 M in 60 mL, 0.2-0.5 M in 45 mL and 0.5-1.0 M in 0.1 mL at 5 mL/min flow rate). Fractions of 5 mL were collected and assayed for CKI activity.

Fraction 7 from the HiTrapQ run, which contained peak TgCKIα activity, was concentrated (Amicon Ultra® unit), filtered (0.22 μm pore size), and approximately 0.5 mL was loaded onto a SMART system FPLC System 0.1-mL phenyl superose PC 1.6/5 hydrophobic interaction chromatography column (Pharmacia). A linear (NH$_4$)$_2$SO$_4$ gradient was applied (1.0 M-0 in 1.5 mL at 0.05 mL/min flow rate). Fractions of 0.1 mL were collected and assayed for CKI activity, and the active fractions corresponding to the single peak were pooled for serological and enzymatic analysis.

Partial purification of native EtCKIα—The inability to stably express recombinant EtCKIα in *T. gondii* provided impetus to purify native enzyme from *E. tenella* parasites (slide 5). A lysate was prepared from 2×10$^{10}$ unsporulated oocysts using previously published procedures (Gurnett, A.

M. et al., 2002, supra). The first two steps of the purification scheme used were essentially scaled-up from the method described for the purification of native TgCKIα. The lysate was subjected to preparative HiLoad Q anion-exchange chromatography and fractions eluted with a NaCl gradient (0-1 M NaCl). Fractions with peak kinase activity were pooled and subjected to hydrophobic interaction chromatography and fractions were eluted with a linear $(NH_4)_2SO_4$ gradient (1 M to 0). A third and final cation exchange chromatography purification step resulted in active fractions of sufficient purity.

Compounds—A collection of ATP-site competitive inhibitors of CDKs were used (Knockaert, M. et al., 2002, *Trends Pharmacol. Sci.* 23:417-425). All but aminopurvalanol are currently available commercially (e.g., Alexis Corporation, Tocris, Calbiochem, and A. G. Scientific). They were stored as 10 mM stock solutions in DMSO.

Results—In order to obtain sufficient quantity and purity of TgCKI enzyme for biochemical characterization, recombinant $_{FLAG}$TgCKIα and $_{FLAG}$TgCKIβ proteins were expressed in *E. coli* and purified in a two step procedure. After an initial FLAG-affinity purification step, partially purified $_{FLAG}$TgCKIα and $_{FLAG}$TgCKIβ enzymes were subjected to anion exchange FPLC chromatography using a linear salt gradient to elute CKI activity. Fractions with peak CKI activity were analyzed by SDS-PAC-E and stained with silver (FIG. 8A). The purity of recombinant TgCKIα and TgCKIβ enzymes was estimated by densitometry as 30%, and greater than 95%, respectively. The lower purity of the $_{FLAG}$TgCKIα enzyme is a reflection of the relatively poor yield of soluble enzyme recoverable from *E. coli* lysates compared with the TgCKIβ isoform. The identity and integrity of the recombinant enzymes was confirmed in Western blots (FIG. 8B) with antisera raised against conserved and isoform selective epitopes (see FIG. 4). As with recombinant enzymes expressed transiently in *T. gondii*, TgCKIα was observed as a 38 kDa polypeptide, while TgCKIβ exhibited the mobility of a 55 kDa protein rather than the 49 kDa predicted from conceptual translation.

To investigate the activity of the corresponding native TgCKI enzymes in tachyzoites, a detergent extract derived from $2 \times 10^{10}$ parasites was fractionated by HiTrapQ anion exchange chromatography (FIGS. 9A&B). Fractions eluted with a salt gradient were assayed for casein kinase activity using a phosphorylated peptide (KRRRALpSVASLPGL; SEQ ID NO:19) in the presence or absence of 0.2 μM hymenialdisine or 1 μM purvalanol B, compounds that are known or suspected inhibitors of CKI (Meijer, L. et al., 2000, *Chem. Biol.* 7:51-63; Knockaert et al., 2000, supra). This synthetic peptide substrate was chosen rather than casein because it is a highly selective substrate for mammalian CKI as a result of the preference this enzyme displays for phosphorylating serine residues immediately distal to serines that have previously been modified by cAMP-dependent protein kinase ("PKA") (Flotow, H. et al., 1990, *J. Biol. Chem.* 265: 14264-14269). Samples of fractions were also blotted and probed with antisera against a conserved internal epitope of TgCKIα which recognized both α and β forms of $_{FLAG}$TgCKI (FIG. 9B). A prominent peak of hymenisaldisine and purvalanol B sensitive phosphopeptide kinase activity was identified in fractions 5-9 that correlated with the presence of a CKI-specific 38 kDa protein in the Western blot. A second less active peak was detected in fractions 14 and 15, which exhibited partial sensitivity to hymnenialdisine and purvalanol B. Although a 60 kDa Western blot positive band detected with CKI antisera (FIG. 9B) was found in these fractions, its presence did not correlate with phosphopeptide kinase activity. Furthermore, since replica blots probed with antisera selective for TgCKIβ failed to detect the presence of cross-reacting protein in any of these fractions, it was concluded that this 60 kDa band is not TgCKIβ. However, the phosphopeptide kinase activity of fractions 14 and 15 did correlate with the presence of *T. gondii* calmodulin domain-like protein kinase 1 (TgCDPK1), an enzyme that can also use casein as a substrate in vitro (not shown). Kinase assays with synthetic peptides that are preferred by TgCDPK1 (Syntide-2 and CaM kinase II substrate (281-291); Kieschnick et al., 2001, supra) confirmed a prominent peak of activity spanning these two fractions (not shown).

HiTrapQ fraction 7, which contained the peak activities for phosphopeptide kinase- and 38 kDa CKI protein, was subjected to hydrophobic interaction chromatography to further purify and concentrate the native CKI activity (FIG. 9C). A peak of phosphopeptide kinase activity was eluted with a descending ammonium sulfate gradient which matched the presence of a 38 kDa band that was recognized by antisera specific for the TgCKIα isoform. (FIG. 9D, 'CKIα-Ct'). The co-purification of phosphopeptide kinase activity with a 38 kDa TgCKIα protein through two column chromatography procedures suggested that the activity represents that of the native TgCKIα isoform. Fractions 14 and 15, containing the highest levels of this activity, were combined for further analysis.

A characterization of the enzymatic activities of preparations of recombinant TgCKIα or β and partially purified native TgCKIα isoforms is shown in Table I and FIG. 10. A determination of the selectivities of the CKI enzyme preparations for casein and synthetic peptide substrates revealed qualitatively similar apparent $K_m$ and $V_{max}$ values. All of the CKI enzyme preparations yielded maximal activity with the phosphopeptide substrate. In the case of the recombinant TgCKI enzymes, where the greater degree of purity achieved permitted the determination of apparent $V_{max}$ values, 2-3 fold higher levels of activity were obtained with this peptide than with either α- or β-casein. This similar increase was also seen in a comparison of maximal activity levels observed for the native TgCKIα preparation with these substrates (not normalized for protein, FIG. 10B). Most non-phosphorylated synthetic peptides tested, including those recognized by TgCDPK1 (Syntide-2 or CaM kinase II substrate), PKA (kemptide), some CKI enzymes [DDDEESITRR-OH (SEQ ID NO:17) or RRKDLHDDEEDEAMSITA-OH (SEQ ID NO:13)], and CKII [RRADDSDDDDD-OH (SEQ ID NO:14) or RRREEETEEE-OH (SEQ ID NO:20)] failed to show concentration dependent kinase activity. The single exception, a CKI peptide substrate (RRKDLHDDEEDEAM-SITA-OH (SEQ ID NO:13)) yielded low levels of activity with $_{FLAG}$TgCKIβ, but the activity was closer to background levels with native TgCKIα or $_{FLAG}$TgCKIβ enzymes (Table I, FIG. 10C). Substrate selectivity and biochemical properties of the native EtCKIα enzyme were found to be very similar to the native TgCKIα. For example, in comparing the α-casein protein substrate with the preferred CKI phosphopeptide substrate, the phosphopeptide yielded a much higher $V_{max}$ (2.5× greater activity) than the α-casein substrate, similar to that seen with the recombinant TgCKIα and -β and native TgCKIα enzymes, While purifying native *E. tenella* CKIα from unsporulated oocysts, a third and final cation exchange chromatography purification step resulted in active fractions of sufficient purity to identify a discrete ~40 kDa band on a silver stained SDS-PAGE gel (FIG. 11A), which cross-reacted with CKI antisera and which correlated with CKI activity (FIG. 11B). The activity was sensitive to a PKG inhibitor, Compound 20 (structure disclosed in PCT International Application PCT/

US02/19507; International publication number WO 03/000682), with 100% inhibition at 250 nM.

Figure 12:
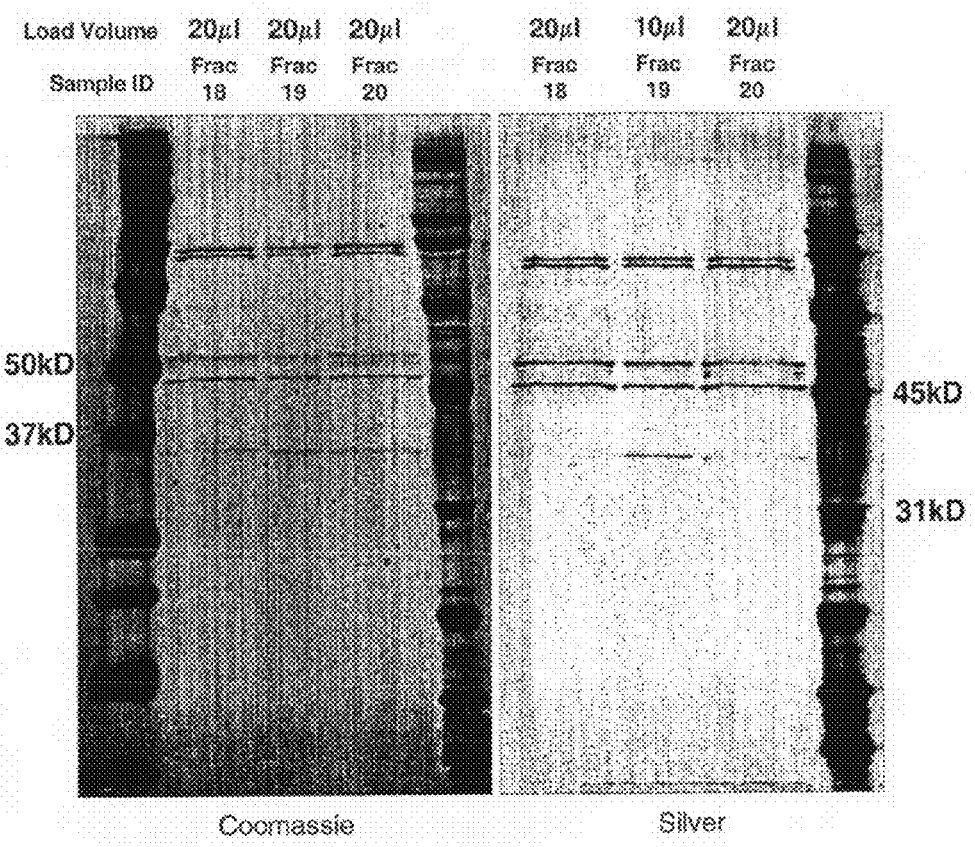
FIG. 12 shows preparative 10-20% SDS-PAGE gels stained with Coomassie and Silver for purification of EtCKIα. Bands from fractions 18-20 corresponding to the ~40 kDa protein were excised and subjected to tandem LC-MS/MS analysis following digestion with trypsin.

To confirm the identity of native E. tenella CKIα, fractions 18, 19, and 20 from a EtCKIα purification were separated with SDS-PAGE. The gel was stained with Colloidal Coomassie, as well as silver stain (FIG. 12). The ~40 kDa band was excised and digested with trypsin, and the resulting peptides were analyzed by nanoflow HPLC-micro-electrospray ionization tandem mass spectrometry. All the collected tandem mass spectra were processed using TurboSEQUEST to search against the E. tenella CKIα open reading frame. To confirm the identity of the tryptic peptides, an aliquot of the peptides was dried down and esterified in 2N methanolic HCl, which results in methyl groups (or 14 Da) being added to the acidic groups of every peptide. The resulting methyl esters were analyzed and processed in the same manner as described above. Molecular profiling showed conclusively that the LC-MS/MS profile of the ~40 kDa native protein matches the sequence of the cloned EtCKIα enzyme. Seven tryptic peptides were positively identified: SRHPQLIYESK (SEQ ID NO:37); TVLMLADQMLNR (SEQ ID NO:38); DIKPDNFLIGR (SEQ ID NO:39); TQSHIPYR (SEQ ID NO:40); YASVNTHLGIEQSR (SEQ ID NO:41); FEDRPDYSYLR (SEQ ID NO:42); and, DLFFR (SEQ ID NO:43) (represented by the shaded boxes in FIG. 13). Five of these peptides were confirmed following methyl ester derivitization: SRHPQLIYESK (SEQ ID NO:37); DIKPDNFLIGR (SEQ ID NO:39); YASVNTHLGIEQSR (SEQ ID NO:41); FEDRPDYSYLR (SEQ ID NO:42); and, DLFFR (SEQ ID NO:43).

TABLE 1

Kinetic parameters of TgCKα and TgCKIβ isoforms.

| Substrate | $_{FLAG}$TgCKIβ | | $_{FLAG}$TgCKIα | | native TgCKIα |
|---|---|---|---|---|---|
| | $V_{max(app)}$ | $K_{m(app)}$ | $V_{max(app)}$ | $K_{m(app)}$ | $K_{m(app)}$ |
| α-casein | 12 | 5 | 8 | 4 | 3 |
| β-casein | 16 | 12 | 8 | 30 | 13 |
| CKI peptide | 8 | 15 | NA | NA | NA |
| CKI phosphopeptide | 37 | 79 | 26 | 80 | 20 |

Values for $V_{max(app)}$(nmole min$^{-1}$ mg$^{-1}$) and $K_{m(app)}$(μM) were determined from titrations performed in a representative experiment (n = 2 to 3). Catalytic parameters were measured in the presence of 2 μM ATP and 200 μM peptide or casein substrate. Parameters were calculated using curve-fitting software (Graphpad Prism) with "goodness of fit" values of $R^2 > 0.990 \pm 0.002$ for all values presented. Examples of plots from which these values were calculated are shown in FIG. 10. 'NA' is not active.

EXAMPLE 4

Inhibitor Studies

Compounds—A collection of ATP-site competitive inhibitors of CDKs were used (Knockaert et al., 2002, Trends Pharmacol. Sci.). All but aminopurvalanol are currently available commercially (e.g., Alexis Corporation, Tocris, Calbiochem, and A. G. Scientific). They were stored as 10 mM stock solutions in DMSO.

Purification of recombinant TgCDPK1 and TgPKG—The TgCDPK1 open reading frame was amplified by PCR from a Toxoplasma cDNA library, using primers based on the published sequence (Kieschnick et al., 2001, supra): sense primer, AAAATGGGGCAGCAGGAAAGCACTCTTGGG (SEQ ID NO:44); and, antisense primer, GTTTCCGCAGAGCTTCAAGAGCATCTGTT (SEQ ID NO:45). A C-terminal FLAG epitope tag was appended to the TgCDPK1 open reading frame by an additional round of PCR amplification (KOD polymerase) and the resulting DNA fragment was sub-cloned into a tubulin promoter expression vector (Donald and Liberator, 2002, supra). To facilitate the selection of stable transgenic lines, an HXGPRT minigene fragment was sliced into a unique expression-vector BamHI site, permitting mycophenolic acid selection in the parasite HXGPRT knockout strain (Donald, R. G. K. et al., 1996, J. Biol. Chem. 271:14010-14019). Recombinant $_{FLAG}$TgCDPK1 and $_{FLAG}$PKG enzymes were recovered from transgenic parasites by single step FLAG-affinity purification as described previously (Donald and Liberator, 2002, supra). The activity of the $_{FLAG}$TgCDPK1 enzyme closely resembled properties of the native TgCDPK1 enzyme with respect to sensitivity to calcium and apparent $K_m$ and $V_{max}$ values (Kieschnick et al, 2001, supra).

Figure 14:
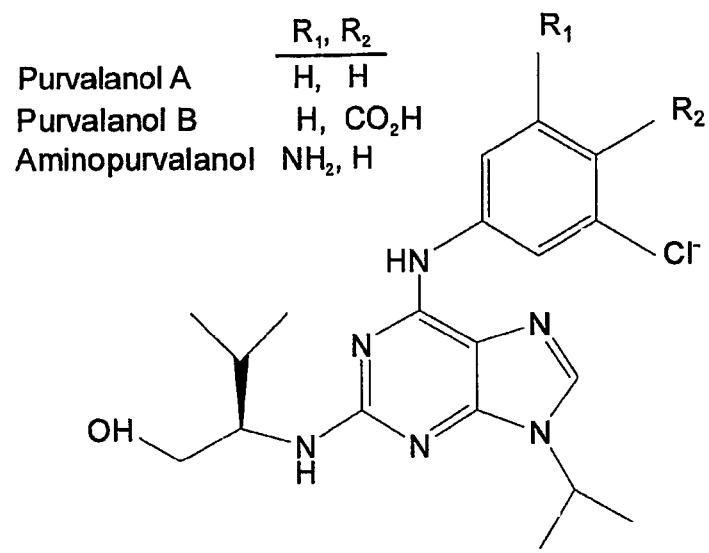
FIG. 14 shows the structure of active purvalanol compounds. Purvalanol B and amino purvalanol share polar phenyl ring substitutents ($R_1$ and $R_2$) and show good activity against TgCKIα and $T.\ gondii$ grown in vitro, as well as EtCKIα (Table 2). Purvalanol A and structurally related compounds such as Roscovitine and Olomoucine lack these moieties.

Results—The sensitivity of CKI enzymes and T. gondii parasites to a variety of antimitotic CDK inhibitors was evaluated, and the results are shown in Table 2. Compound 1, a selective inhibitor of coccidian parasite PKG with well-characterized anti-parasitic properties (Nare, B. et al., 2002, supra; Gurnett, et al., 2002, supra; Donald et al., 2002, supra; U.S. Pat. No. 6,291,480), was included as an additional reference compound. The first five CDK compounds listed (Compounds 2-6) belong to the 2,6,9-trisubstituted purine structural class of which the purvalanols are members (Meijer and Raymond, 2003, Accounts Chem. Res. 36:417-425). Aminopurvalanol, purvalanol A and purvalanol B are highly potent and selective CDK inhibitors with relatively low activity against other kinases in mammalian cells (Chang, Y. T. et al., 1999, Chem. Biol. 6:361-375; Gray, N. S. et al., 1998, Science 281:533-538; Knockaert et al., 2000, supra). The structures of these compounds are shown in FIG. 14. Indirubin-3'-monoxime, an active ingredient of a Chinese anti-leukemic herbal remedy, is a less selective compound with activity against a number of other mammalian kinases including glycogen synthase kinase (GSK-3), AMP-activated protein kinase (AMPK), a tyrosine kinase (LCK), and serum activated protein kinase (SGK) (Leclerc, S. et al., 2001, J. Biol. Chem. 276:251-260; Damiens, E. et al., 2001, Oncogene 20:3786-3797; Marko, D. et al., 2001, Br. J. Cancer 84:283-289; Bain, J. et al., 2003, Biochem. J. 371:199-204). Hymenialdisine, a marine sponge constituent, is a potent inhibitor of human CDKs, but also of GSK-3 and CKI (Meijer, L. et al., 2000, Chem. Biol. 7:51-63). Kenpaullone and alsterpaullonie, representatives of the paullone family of compounds, display good selectivity toward CDKs, although they are also potent inhibitors of GSK-3 (Zaharevitz, D. W. et al., 1999, Cancer Res. 59:2566-2569; Knockaert, M. et al., 2002, J. Biol. Chem. 277:25493-25501; Bain et al., 2003, supra). To broaden the scope of this enzyme-target selectivity study, the activity of these compounds against T. gondii PKG and CDPK1 was also assessed.

Two of the purvalanols, purvalanol B and aminopurvalano, showed excellent activity against T. gondii in the uracil uptake assay, a parasite-specific metabolic assay performed with infected HFF cell monolayers (Pfefferkorn and Pfefferkorn, 1977, supra). Other members of this structural class showed only mediocre activity (purvalanol A, roscovitine) or no activity (olomroucine) against cultured parasites. The 260 nM and 375 nM $IC_{50}$ values obtained respectively for purvalanol B and aminopurvalanol are similar to those observed with Compound 1 ($IC_{50}$ 200 nM). These same compounds, but not purvalanol A, roscovitine or olomoucine, also showed good activity against recombinant or native forms of TgCKIα ($IC_{50}$ 40-60 nM). The only other CDK inhibitor with sub-µM activity against *T. gondii* was indirubin-3'-monoxime, which gave an $IC_{50}$ value of 500 nM. This compound showed modest activity against TgCKIα ($IC_{50}$ 172 nM), but also against the CDPK1 enzyme ($IC_{50}$ 175 nM). Hymenialdisine showed no antiparasitic activity, but was a potent inhibitor of both α and β isoforms of TgCKI ($IC_{50}$ 7-10 nM) as well as rodent CKIδ ($IC_{50}$ 60 nM). Neither kenpaullone nor alsterpaullone showed any activity against the parasite kinases tested. Compared with kenpaullone, which was inactive in the whole cell assay, alsterpaullone showed some antiparasitic activity at low micromolar levels ($IC_{50}$ 1.2 µM). Alsterpaullone is at least 10-fold more potent against mammalian CDK1 or CDK5 than kenpaullone (Knockaert, M. et al, 2002, *J. Biol. Chem.*). Native EtCKIα shows similar sensitivities as compared to TgCKI enzymes to these references compounds (Table 2).

Figure 15:
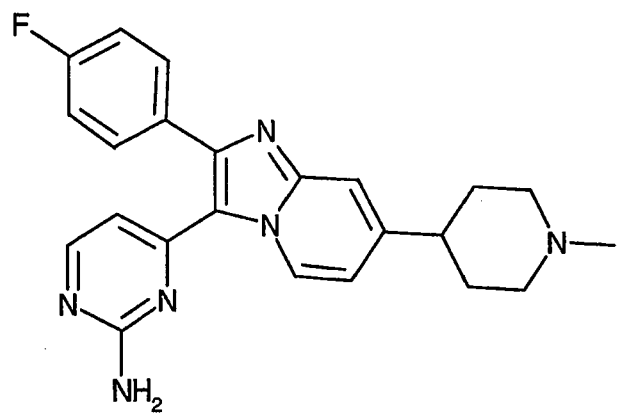
FIG. 15 shows the structure of the imidazopyridine compound labeled Compound 39 (see Table 3), 4[2-(4-Fluorophenyl)1-7-(1-methylpiperidin-4-yl)imidazo[1,2-a]pyridin-3-yl]pyrimidin-2-amine.

Biochemical characterization of the partially purified native EtCKIα isoform (e.g., fraction 19, FIG. 13) shows that it resembles its *T. gondii* counterpart with respect to substrate selectivity and sensitivity to reference compounds (CDK inhibitors) and imidazopyridines (PKG inhibitor leads). Table 3 summarizes the sensitivity of various coccidian protein kinases to two imidazopyridine compounds, Compound 20 (PCT International Application PCT/US02/19507; International publication no. WO 03/000682) and Compound 39 (see FIG. 15). *T. gondii* and *E. tenella* CKI enzymes show modest levels of sensitivity to these compounds.

TABLE 2

Sensitivity of *T. gondii* PKG, CKIα and -β (expressed and native), and CDPK1; and native *E. tenella* CKIα, and rat CKIδ to inhibitors of mammalian CDK.

| Inhibitor | $^3$[H]Uracil Uptake | TgPKG | TgCDPK1 | TgCKIβ | TgCKIα | native TgCKIα | native EtCKIα | Rat CKIδ |
|---|---|---|---|---|---|---|---|---|
| 1. Compound 1 | 200 ± 100 | 0.7 ± 0.3 | 63 ± 2 | 4,200 | 107 ± 19 | 95 ± 28 | 350 | 2,230 |
| 2. Purvalanol A | 1,230 | 3,500 | 4140 | >5,000 | >5,000 | >5,000 | 4,900 | >5,000 |
| 3. Purvalanol B | 260 ± 84 | 1,900 | 770 ± 200 | 606 | 38 ± 12 | 63 | 94 | 3,600 |
| 4. Aminopurvalanol | 375 ± 21 | 2,200 | 730 ± 200 | 3760 | 42 ± 7 | 61 | 98 | 3,500 |
| 5. Roscovitine | >5,000 | 10,000 | >5,000 | >5,000 | 1,200 | 1,200 | 1,700 | >5,000 |
| 6. Olomoucine | >5,000 | 10,000 | 4200 | >5,000 | >5,000 | >5,000 | NT | >5,000 |
| 7. Indirubin-3'-monoxime | 500 ± 100 | 1865 | 172 ± 4 | 1340 | 124 ± 21 | 550 | NT | >5,000 |
| 8. Hymenialdisine | >10,000 | 2136 | 175 ± 33 | 11 ± 6 | 7 ± 3 | 10 | NT | 60 |
| 9. Alsterpaullone | 1,220 | >5,000 | >5,000 | >5,000 | >5,000 | NT | NT | 2,300 |
| 10. Kenpaullone | >5,000 | >5,000 | >5,000 | >5,000 | >5,000 | NT | NT | >5,000 |

PKG inhibitor Compound 1 was included as a control. Enzyme- and whole cell- metabolic activities were assayed as described above in the presence of increasing concentrations of compound. $IC_{50}$ values (nM) were calculated from dose response curves. Submicromolar values are highlighted in grey. 'NT' is not tested. Structures of purvalanols A, B and aminopurvalanol are shown in FIG. 14. The errors shown for some values represent standard deviations resulting from additional titration experiments (n = 2-3).

TABLE 3

Coccidian CKIα and CDPK1 enzymes are secondary targets of lead PKG inhibitors. Sensitivity of recombinant- or partially purified native enzymes to PKG inhibitors was determined from dose response titrations (nM $IC_{50}$ values). Recombinant enzymes were purified from *E. coli* and native enzymes from extracts of *Toxoplasma* tachyzoites (TgCKIα) or *Eimeria* oocysts (EtCKIα and EtPKG).

| Enzyme | Compound 20 | Compound 39 |
|---|---|---|
| $_{FLAG}$TgCDPK1 | 1.1 | 0.5 |
| $_{FLAG}$TgCDPK3 | >10,000 | >10,000 |
| $_{FLAG}$EtCDPK1 | 413 | 126 |
| $_{FLAG}$EtCDPK2 | >10,000 | >10,000 |
| $_{native}$TgCKIα | 18 | 15 |
| $_{native}$EtCKIα | 84 | 69 |
| $_{native}$EtPKG | 0.7 | 0.5 |

What is claimed is:

1. A purified nucleic acid molecule comprising a nucleotide sequence selected from the group consisting of:
   (a) a nucleotide sequence which encodes the amino acid sequence of SEQ ID NO:2; and
   (b) a nucleotide sequence which hybridizes under conditions of high stringency to the complement of a second nucleic acid molecule which encodes the amino acid sequence of SEQ ID NO:2, wherein high stringency conditions are 0.1×SSC at about 68° C.,
   wherein the nucleotide sequence is a coccidian sequence and encodes an amino acid sequence that has at least 90% identity to the amino acid sequence of SEQ ID NO:2 and has casein kinase I (CKI) activity.

2. An expression vector for expressing a coccidian CKI protein in a recombinant host cell wherein said expression vector comprises the nucleic acid molecule of claim 1.

3. An isolated recombinant host cell which expresses a coccidian CKI protein wherein said host cell contains the expression vector of claim 2.

4. A process of expressing a coccidian CKI protein in a recombinant host cell, comprising:
   (a) transfecting the expression vector of claim 2 in a suitable host cell; and,
   (b) culturing the isolated host cell of step (a) under conditions which allow expression of said coccidian CKI protein from said expression vector.

5. An isolated nucleic acid molecule encoding a coccidian CKI protein, wherein said nucleic acid molecule comprises the nucleotide sequence of SEQ ID NO:1.

6. An expression vector for expressing a coccidian protein in a recombinant cell wherein said expression vector comprises the nucleic acid molecule of claim 5.

7. An isolated recombinant host cell which expresses a coccidian CKI protein wherein said host cell contains the expression vector of claim 6.

8. A process of expressing a coccidian CKI protein in an isolated recombinant host cell, comprising:
   (a) transfecting the expression vector of claim 6 into a suitable isolated host cell; and
   (b) culturing the host cell of step (a) under conditions which allow expression of said coccidian CKI protein from said expression vector.

9. The purified nucleic acid molecule of claim 1, wherein said nucleic acid molecule comprises a nucleotide sequence which encodes the amino acid sequence of SEQ ID NO:2.

* * * * *

SEQUENCE LISTING

<160> NUMBER OF SEQ ID NOS: 45

<210> SEQ ID NO 1
<211> LENGTH: 2182
<212> TYPE: DNA
<213> ORGANISM: Eimeria tenella
<220> FEATURE:
<221> NAME/KEY: CDS
<222> LOCATION: (715)...(1722)

<400> SEQUENCE: 1

| | |
|---|---|
| gcggccgcgt cgacgtctttt gctgccgcac agggagcagc agcagccgcc gacccgatcc | 60 |
| cttgggagcc caccaagtgc tgcgcttgct tagcagctac aggagctgcc gcggggttgc | 120 |
| tccctgaggc agcgtgcatg tatggtccgg cagccagctt ggtgtcgcag ccgtacttct | 180 |
| tggaagcgag agagactgtg ggagagcgca atcactcca gccgcttcca ggggagtctg | 240 |
| gggaccgcag gagcgttgga ggctgcctgc cggcataaac aggaacaagc gcattcttat | 300 |
| tcttctgtgg ttgctgagtt ctggctgcgt tcaagggggt tcacctcttc cccttctggc | 360 |
| gagttttttgc tgcgtctttc cctaagaagc agcgccacgt gcgtggcgtg cctcagcctg | 420 |
| acgcggtgca ccttttacgt aagagcgtcg atagcatcgg tcatctacag cagcgtgctg | 480 |
| ctgcttccgt gacctttaca ctgcttgtgg cgggccgtct tgtagagggg ccatctgctt | 540 |
| gttcgctgct ggacgcagac ccggcgcccg acatttccgg cagccgggca gttgagataa | 600 |
| accggctgcc cggtggccgt cgaaattgaa gcaggatctc tacagtaagg aacaaatcgc | 660 |
| gctattttta aggagtgtgt atacttgggg cgttactcgt gagtattgct gatg atg | 717 |
|    Met |  |
|     1 | |

| | |
|---|---|
| gac gtc cgt gtg ggg ggt aag tat cgt ttg ggg agg aag att ggg agc | 765 |
| Asp Val Arg Val Gly Gly Lys Tyr Arg Leu Gly Arg Lys Ile Gly Ser | |
|      5              10               15 | |
| gga tcc ttc ggc gac atc tac ctt ggt acg aac atc tca aca gga gat | 813 |
| Gly Ser Phe Gly Asp Ile Tyr Leu Gly Thr Asn Ile Ser Thr Gly Asp | |
|          20             25            30 | |
| gaa gtc gct atc aaa ttg gaa agc gtg cgg tct agg cat cca caa cta | 861 |
| Glu Val Ala Ile Lys Leu Glu Ser Val Arg Ser Arg His Pro Gln Leu | |
|       35             40              45 | |
| atc tat gaa agc aag ctg tac aaa atc cta acg ggt gga atc gga atc | 909 |
| Ile Tyr Glu Ser Lys Leu Tyr Lys Ile Leu Thr Gly Gly Ile Gly Ile | |
|  50            55             60               65 | |
| ccg act ctt tac tgg tat ggg atc gag ggg gat tac aac gtt atg att | 957 |
| Pro Thr Leu Tyr Trp Tyr Gly Ile Glu Gly Asp Tyr Asn Val Met Ile | |
|                70               75            80 | |
| att gag ctt ttg ggc ccg tct ctt gag gac ctc ttc agc att tgc aac | 1005 |
| Ile Glu Leu Leu Gly Pro Ser Leu Glu Asp Leu Phe Ser Ile Cys Asn | |
|              85              90            95 | |
| aga aag ctt tct ttg aag act gtt ctg atg ctc gcc gac caa atg cta | 1053 |
| Arg Lys Leu Ser Leu Lys Thr Val Leu Met Leu Ala Asp Gln Met Leu | |
|           100            105           110 | |
| aat cgt att gag ttc gtc cac agc aga cat ttc atc cat cga gac atc | 1101 |
| Asn Arg Ile Glu Phe Val His Ser Arg His Phe Ile His Arg Asp Ile | |
|     115            120           125 | |
| aag cct gac aat ttt ttg atc ggt agg ggc aaa aag atg tcc att gtt | 1149 |
| Lys Pro Asp Asn Phe Leu Ile Gly Arg Gly Lys Lys Met Ser Ile Val | |
| 130            135            140           145 | |
| ttt gct atc gac ttt ggc ctc gca aag aag tac aga gat ccc aga aca | 1197 |
| Phe Ala Ile Asp Phe Gly Leu Ala Lys Lys Tyr Arg Asp Pro Arg Thr | |

```
                   150                155                160
cag tcc cat att cct tat cga gaa ggg aag aac ctg aca ggt acc gcg    1245
Gln Ser His Ile Pro Tyr Arg Glu Gly Lys Asn Leu Thr Gly Thr Ala
            165                170                175 agg tac gcc tct gtg aac acc cac ttg gga ata gaa cag agc agg cgc    1293
Arg Tyr Ala Ser Val Asn Thr His Leu Gly Ile Glu Gln Ser Arg Arg
        180                185                190 gat gat ctg gaa gcg ctc ggc tac gtc tta atg tac ttc aac aga ggt    1341
Asp Asp Leu Glu Ala Leu Gly Tyr Val Leu Met Tyr Phe Asn Arg Gly
    195                200                205 tcc tta ccc tgg caa gga tta aag gcc act acg aag aaa gat aaa tat    1389
Ser Leu Pro Trp Gln Gly Leu Lys Ala Thr Thr Lys Lys Asp Lys Tyr
210                215                220                225 gac aag att atg gag aag aag atg tcc acc cct att gaa gtc ctt tgc    1437
Asp Lys Ile Met Glu Lys Lys Met Ser Thr Pro Ile Glu Val Leu Cys
                230                235                240 aaa caa ttt cca ttt gag ttt atc aca tat ctg aac tat tgc cgg tct    1485
Lys Gln Phe Pro Phe Glu Phe Ile Thr Tyr Leu Asn Tyr Cys Arg Ser
            245                250                255 ctg cga ttc gaa gat cgc ccg gac tat tcc tat ttg aga cgg ttg ttc    1533
Leu Arg Phe Glu Asp Arg Pro Asp Tyr Ser Tyr Leu Arg Arg Leu Phe
        260                265                270 aag gat ctt ttc ttc cgt gag gga tac cag tat gac ttt ata ttc gat    1581
Lys Asp Leu Phe Phe Arg Glu Gly Tyr Gln Tyr Asp Phe Ile Phe Asp
    275                280                285 tgg aca ttt ctg cat gct gag aga gag cgc gag cgt caa aga cga tcg    1629
Trp Thr Phe Leu His Ala Glu Arg Glu Arg Glu Arg Gln Arg Arg Ser
290                295                300                305 atg gtc aac caa ggc gca gaa tca ggg aac cag tgg aga cga gac gcg    1677
Met Val Asn Gln Gly Ala Glu Ser Gly Asn Gln Trp Arg Arg Asp Ala
                310                315                320 tcg ggc aga gat cca ctt gga cgg ttg cct cag tta gaa ccg taa       1722
Ser Gly Arg Asp Pro Leu Gly Arg Leu Pro Gln Leu Glu Pro *
            325                330                335 tctctttacg ggcagattgc cgtacgggtc ttctgctcat tcagtggcag tgccaccgca  1782
gtgctatctg aggctgtggc ttcaggatgt ggtagccagt taccatggtc acttgccctc  1842
gctaggacag ccttcgcagg gaaatgtcac agtagcctgc attatgtggt gtgagaactg  1902
ctagcgcatt cctgtagttg cttttacgaa gcaggatacg cagcgtgcat cacgcggtgg  1962
ttcgagcgct cgctacgcat cacagggctg tgaggcaagt tagtatcttt ggggacgag   2022
ttgagagtgt cagaatcgat agtctcaggg catgcaggcg aaatggaggc tgcgccagta  2082
gtgccagccg gtggcgaagg cgtcaaattt acttttttg ttgctgggga tattgttaga  2142
gcaacaactt gggtctagat gctactgata aaaaaaaaa                        2182

<210> SEQ ID NO 2
<211> LENGTH: 335
<212> TYPE: PRT
<213> ORGANISM: Eimeria tenella

<400> SEQUENCE: 2

Met Asp Val Arg Val Gly Gly Lys Tyr Arg Leu Gly Arg Lys Ile Gly
1               5                   10                  15

Ser Gly Ser Phe Gly Asp Ile Tyr Leu Gly Thr Asn Ile Ser Thr Gly
            20                  25                  30

Asp Glu Val Ala Ile Lys Leu Glu Ser Val Arg Ser Arg His Pro Gln
        35                  40                  45
```

```
Leu Ile Tyr Glu Ser Lys Leu Tyr Lys Ile Leu Thr Gly Gly Ile Gly
     50                  55                  60

Ile Pro Thr Leu Tyr Trp Tyr Gly Ile Glu Gly Asp Tyr Asn Val Met
 65                  70                  75                  80

Ile Ile Glu Leu Leu Gly Pro Ser Leu Glu Asp Leu Phe Ser Ile Cys
                 85                  90                  95

Asn Arg Lys Leu Ser Leu Lys Thr Val Leu Met Leu Ala Asp Gln Met
            100                 105                 110

Leu Asn Arg Ile Glu Phe Val His Ser Arg His Phe Ile His Arg Asp
        115                 120                 125

Ile Lys Pro Asp Asn Phe Leu Ile Gly Arg Gly Lys Lys Met Ser Ile
130                 135                 140

Val Phe Ala Ile Asp Phe Gly Leu Ala Lys Lys Tyr Arg Asp Pro Arg
145                 150                 155                 160

Thr Gln Ser His Ile Pro Tyr Arg Glu Gly Lys Asn Leu Thr Gly Thr
                165                 170                 175

Ala Arg Tyr Ala Ser Val Asn Thr His Leu Gly Ile Glu Gln Ser Arg
            180                 185                 190

Arg Asp Asp Leu Glu Ala Leu Gly Tyr Val Leu Met Tyr Phe Asn Arg
        195                 200                 205

Gly Ser Leu Pro Trp Gln Gly Leu Lys Ala Thr Thr Lys Lys Asp Lys
210                 215                 220

Tyr Asp Lys Ile Met Glu Lys Lys Met Ser Thr Pro Ile Glu Val Leu
225                 230                 235                 240

Cys Lys Gln Phe Pro Phe Glu Phe Ile Thr Tyr Leu Asn Tyr Cys Arg
                245                 250                 255

Ser Leu Arg Phe Glu Asp Arg Pro Asp Tyr Ser Tyr Leu Arg Arg Leu
            260                 265                 270

Phe Lys Asp Leu Phe Phe Arg Glu Gly Tyr Gln Tyr Asp Phe Ile Phe
        275                 280                 285

Asp Trp Thr Phe Leu His Ala Glu Arg Glu Arg Gln Arg Arg
290                 295                 300

Ser Met Val Asn Gln Gly Ala Glu Ser Gly Asn Gln Trp Arg Arg Asp
305                 310                 315                 320

Ala Ser Gly Arg Asp Pro Leu Gly Arg Leu Pro Gln Leu Glu Pro
                325                 330                 335

<210> SEQ ID NO 3
<211> LENGTH: 2076
<212> TYPE: DNA
<213> ORGANISM: Toxoplasma gondii
<220> FEATURE:
<221> NAME/KEY: CDS
<222> LOCATION: (898)...(1872)

<400> SEQUENCE: 3
cctcgttttg cttcattccc cgccttttct ctgtagctaa ccaaaggaac aaagtcagcg      60
gtagaagccg tttcttctgt ccgcttccca ctcttcccgt tcggctgccc ctgcagagcg     120 cccctttctat gcgttgccac ccgtctgcaa gtatcgcgtc tttcgtctca tcagtgattt    180
tctttgcgtg tcgcgttcgg gacgcccttt ctctcctca actaactagc agacgtttct     240
tccgtcccgc atgcgacagc gaagggcacg tccccccagt tcttcatcgc ccacctgttg    300
tgcaacttgt cgcccgtcgt tcttcacttc ttctctccca tcctctcgtg actcttcctc    360
tcgagaactc tttctgtcga actctcaacc cccacgactg ctggtttcgt ggccgtcccg    420
```

-continued

```
catgcacctt gtgtcccgcc gccttggcgc aaacacccgc tttctctgct gtccgcctcc     480
cggtggactt ctctccgtgt tttttcgtgt tgccaaaagt ttgtctgctt tgacgtttct     540
ctgctcaccc attgcccgct cttgatgagg aacgctccac attgacagcg aactcacagc     600
acgcaccctc cgcgagcgga ctttcacgag cgaggcaaga atccatcgtc accccgccta     660
cacgtacact actccacttg ggtgcccacg cgcggcttct gggagacaga gacggtcctc     720
gttttccgtg tcagaacttt gtcgaggaaa cgctgctgct ggcagcgggg attgtgaccc     780
ccctcggcga acgggcgaag ccgccctgtc gcgcgtcgcg actcagctga ggcgacaggc     840
ggtcggcggc gtgacctctc tttcttttg cattcggccc tgattgcagc acgaagg atg     900
                                                                  Met
                                                                   1
```

| | | | | | | | | | | | | | | | | |
|---|---|---|---|---|---|---|---|---|---|---|---|---|---|---|---|---|
| gag | gtc | agg | gtc | gga | ggc | aag | tac | cga | ctt | ggt | cgg | aag | atc | ggc | agc | 948 |
| Glu | Val | Arg | Val | Gly | Gly | Lys | Tyr | Arg | Leu | Gly | Arg | Lys | Ile | Gly | Ser | |
| | | 5 | | | | 10 | | | | 15 | | | | | | |

```
ggg tca ttc ggt gat att tat atc ggt gca aac att ttg acg ggg gat     996
Gly Ser Phe Gly Asp Ile Tyr Ile Gly Ala Asn Ile Leu Thr Gly Asp
         20                  25                  30 gag gtg gcg atc aag ttg gag tct atc aag tcg aag cac ccg cag ctg    1044
Glu Val Ala Ile Lys Leu Glu Ser Ile Lys Ser Lys His Pro Gln Leu
 35                  40                  45 ctc tat gag tcg aag ctg tac aaa ctg ctg gct ggc ggc att ggg att    1092
Leu Tyr Glu Ser Lys Leu Tyr Lys Leu Leu Ala Gly Gly Ile Gly Ile
 50                  55                  60                  65 ccc atg gtc cac tgg tac ggc atc gaa gga gac tac aat gtt atg gtt    1140
Pro Met Val His Trp Tyr Gly Ile Glu Gly Asp Tyr Asn Val Met Val
         70                  75                  80 atc gac ctt ctc ggc cct tct ctg gag gac ctt ttc agt atc tgc aat    1188
Ile Asp Leu Leu Gly Pro Ser Leu Glu Asp Leu Phe Ser Ile Cys Asn
         85                  90                  95 cgc aaa ctc tct ctc aag acg gtg ttg atg ctc gca gac cag atg ctc    1236
Arg Lys Leu Ser Leu Lys Thr Val Leu Met Leu Ala Asp Gln Met Leu
        100                 105                 110 aac cgc atc gag ttt gtc cat agc aag aac ttc atc cat cgc gat atc    1284
Asn Arg Ile Glu Phe Val His Ser Lys Asn Phe Ile His Arg Asp Ile
        115                 120                 125 aaa ccc gac aac ttc ctc att ggc cgt gga aag aag atg tcc gtc gtc    1332
Lys Pro Asp Asn Phe Leu Ile Gly Arg Gly Lys Lys Met Ser Val Val
130                 135                 140                 145 tac atc atc gat ttc ggt ttg gca aag aaa tat cga gac cca aag act    1380
Tyr Ile Ile Asp Phe Gly Leu Ala Lys Lys Tyr Arg Asp Pro Lys Thr
                150                 155                 160 cag caa cat atc cca tac agg gaa ggc aag aac cta aca ggc aca gcg    1428
Gln Gln His Ile Pro Tyr Arg Glu Gly Lys Asn Leu Thr Gly Thr Ala
                165                 170                 175 cgt tac gct tcc atc aac acc cac ctg ggg atc gag cag agt cgg cga    1476
Arg Tyr Ala Ser Ile Asn Thr His Leu Gly Ile Glu Gln Ser Arg Arg
        180                 185                 190 gac gac cta gag gcg ctc ggt tac gtt ctc atg tac ttc aat aga ggt    1524
Asp Asp Leu Glu Ala Leu Gly Tyr Val Leu Met Tyr Phe Asn Arg Gly
        195                 200                 205 tct ctt ccg tkg cag ggt ctg aag gcg acg acg aag aag gac aaa tac    1572
Ser Leu Pro Xaa Gln Gly Leu Lys Ala Thr Thr Lys Lys Asp Lys Tyr
210                 215                 220                 225 gac aag att atg gag aag aaa atg tct act ccc atc gaa att ttg tgc    1620
Asp Lys Ile Met Glu Lys Lys Met Ser Thr Pro Ile Glu Ile Leu Cys
                230                 235                 240 aag cat ttc cca ttc gag ttc atc acc tac ttg aat tac tgc cgg tcc    1668
Lys His Phe Pro Phe Glu Phe Ile Thr Tyr Leu Asn Tyr Cys Arg Ser
```

```
Lys His Phe Pro Phe Glu Phe Ile Thr Tyr Leu Asn Tyr Cys Arg Ser
            245                 250                 255 ctg cgc ttc gag gat cgt cct gac tac gca tac ttg cga cgc ctg ttc       1716
Leu Arg Phe Glu Asp Arg Pro Asp Tyr Ala Tyr Leu Arg Arg Leu Phe
            260                 265                 270 aaa gac ttg ttt ttt aga gag gga tat cag tac gac ttc atc ttc gac       1764
Lys Asp Leu Phe Phe Arg Glu Gly Tyr Gln Tyr Asp Phe Ile Phe Asp
    275                 280                 285 tgg act ttc atc aac acg gag aag gat cgc gcg agt cga aga agc cag       1812
Trp Thr Phe Ile Asn Thr Glu Lys Asp Arg Ala Ser Arg Arg Ser Gln
290                 295                 300                 305 caa gtt tat gtg gaa gac aac cgg caa gtt gag gag aat cag aac gag       1860
Gln Val Tyr Val Glu Asp Asn Arg Gln Val Glu Glu Asn Gln Asn Glu
            310                 315                 320 ttg ccg atg tag ggtggtcggt gtgcggaggc cggcggggag cgtggagtcc           1912
Leu Pro Met * gctgagtctg gaagtctgca gactgtgctc tggcactcga cccacttgtt tgtgtttccc    1972
tcgactcgcg caggtcgagg aaaacagaga cgaacaggtt acccaggagt gttttggtc     2032 aggacgcgcg tctccctctg agtttcgcaa agttgcccct ggaa                     2076

<210> SEQ ID NO 4
<211> LENGTH: 324
<212> TYPE: PRT
<213> ORGANISM: Toxoplasma gondii

<400> SEQUENCE: 4

Met Glu Val Arg Val Gly Gly Lys Tyr Arg Leu Gly Arg Lys Ile Gly
1               5                   10                  15

Ser Gly Ser Phe Gly Asp Ile Tyr Ile Gly Ala Asn Ile Leu Thr Gly
            20                  25                  30

Asp Glu Val Ala Ile Lys Leu Glu Ser Ile Lys Ser Lys His Pro Gln
        35                  40                  45

Leu Leu Tyr Glu Ser Lys Leu Tyr Lys Leu Leu Ala Gly Gly Ile Gly
    50                  55                  60

Ile Pro Met Val His Trp Tyr Gly Ile Glu Gly Asp Tyr Asn Val Met
65                  70                  75                  80

Val Ile Asp Leu Leu Gly Pro Ser Leu Glu Asp Leu Phe Ser Ile Cys
                85                  90                  95

Asn Arg Lys Leu Ser Leu Lys Thr Val Leu Met Leu Ala Asp Gln Met
            100                 105                 110

Leu Asn Arg Ile Glu Phe Val His Ser Lys Asn Phe Ile His Arg Asp
        115                 120                 125

Ile Lys Pro Asp Asn Phe Leu Ile Gly Arg Gly Lys Lys Met Ser Val
    130                 135                 140

Val Tyr Ile Ile Asp Phe Gly Leu Ala Lys Lys Tyr Arg Asp Pro Lys
145                 150                 155                 160

Thr Gln Gln His Ile Pro Tyr Arg Glu Gly Lys Asn Leu Thr Gly Thr
                165                 170                 175

Ala Arg Tyr Ala Ser Ile Asn Thr His Leu Gly Ile Glu Gln Ser Arg
            180                 185                 190

Arg Asp Asp Leu Glu Ala Leu Gly Tyr Val Leu Met Tyr Phe Asn Arg
        195                 200                 205

Gly Ser Leu Pro Trp Gln Gly Leu Lys Ala Thr Thr Lys Lys Asp Lys
    210                 215                 220

Tyr Asp Lys Ile Met Glu Lys Lys Met Ser Thr Pro Ile Glu Ile Leu
```

```
                    225                 230                 235                 240
Cys Lys His Phe Pro Phe Glu Phe Ile Thr Tyr Leu Asn Tyr Cys Arg
                245                 250                 255
Ser Leu Arg Phe Glu Asp Arg Pro Asp Tyr Ala Tyr Leu Arg Arg Leu
            260                 265                 270
Phe Lys Asp Leu Phe Phe Arg Glu Gly Tyr Gln Tyr Asp Phe Ile Phe
        275                 280                 285
Asp Trp Thr Phe Ile Asn Thr Glu Lys Asp Arg Ala Ser Arg Arg Ser
    290                 295                 300
Gln Gln Val Tyr Val Glu Asp Asn Arg Gln Val Glu Glu Asn Gln Asn
305                 310                 315                 320
Glu Leu Pro Met

<210> SEQ ID NO 5
<211> LENGTH: 2373
<212> TYPE: DNA
<213> ORGANISM: Toxoplasma gondii
<220> FEATURE:
<221> NAME/KEY: CDS
<222> LOCATION: (119)...(1417)

<400> SEQUENCE: 5
ttaaccctca ctaaagggaa caaaagctgg agctccaccg cggtggcggc gcaccgagga      60
aaacgcagct cgtaagagac agttctctcg gtgagaagag ctatccgaga aggacacc      118 atg gcg cac cat caa gac acc cgc aac cac acg ggg gtc gga ccc tct      166
Met Ala His His Gln Asp Thr Arg Asn His Thr Gly Val Gly Pro Ser
 1               5                  10                  15 tcg tct atc cct ctg aaa gat ttg aag atc gcc ggc gtc tgg aaa atc      214
Ser Ser Ile Pro Leu Lys Asp Leu Lys Ile Ala Gly Val Trp Lys Ile
             20                  25                  30 ggc aga aaa atc gga tcc ggt tcc ttc ggc gac ata tac aaa ggc ctg      262
Gly Arg Lys Ile Gly Ser Gly Ser Phe Gly Asp Ile Tyr Lys Gly Leu
         35                  40                  45 aat tct cag acc ggt cag gag gtg gcg ctg aag gtc gaa agc acc aag      310
Asn Ser Gln Thr Gly Gln Glu Val Ala Leu Lys Val Glu Ser Thr Lys
     50                  55                  60 gcg aag cat ccg cag ttg ctg tac gaa tac aaa ctt ttg aag cat ttg      358
Ala Lys His Pro Gln Leu Leu Tyr Glu Tyr Lys Leu Leu Lys His Leu
 65                  70                  75                  80 cag gga gga acg ggc att gct caa gtg ttc tgt tgc gag act gcg ggc      406
Gln Gly Gly Thr Gly Ile Ala Gln Val Phe Cys Cys Glu Thr Ala Gly
                 85                  90                  95 gac cat aac atc atg gcc atg gag ttg ctc gga cct tct tta gag gac      454
Asp His Asn Ile Met Ala Met Glu Leu Leu Gly Pro Ser Leu Glu Asp
            100                 105                 110 gtc ttc aac ttg tgc aat cgc acc ttc tct ctc aaa acc att ctt ctt      502
Val Phe Asn Leu Cys Asn Arg Thr Phe Ser Leu Lys Thr Ile Leu Leu
        115                 120                 125 ctc gcc gac cag ttt ctg caa cgc gtc gag tac atc cac tcc aag aat      550
Leu Ala Asp Gln Phe Leu Gln Arg Val Glu Tyr Ile His Ser Lys Asn
    130                 135                 140 ttc att cac aga gat atc aaa cca gat aac ttt ctt ctc ggc ggt gcc      598
Phe Ile His Arg Asp Ile Lys Pro Asp Asn Phe Leu Leu Gly Gly Ala
145                 150                 155                 160 ggc aat caa aac acg atc tac gtg atc gac ttc ggc ctg gcg aag aag      646
Gly Asn Gln Asn Thr Ile Tyr Val Ile Asp Phe Gly Leu Ala Lys Lys
                165                 170                 175 ttt cgc gat ccg aaa acg cac caa cat att ccg tac aga gaa aac aag      694
```

```
                        Phe Arg Asp Pro Lys Thr His Gln His Ile Pro Tyr Arg Glu Asn Lys
                                        180                 185                 190 aat ctc acg gga acg gcg cgc tac gcg tcc atc agt gcg cat ctg ggt                    742
Asn Leu Thr Gly Thr Ala Arg Tyr Ala Ser Ile Ser Ala His Leu Gly
            195                 200                 205 tcc gag cag agt cgc cga gat gac ctc gaa gca gtc ggc tac gtt ctc                    790
Ser Glu Gln Ser Arg Arg Asp Asp Leu Glu Ala Val Gly Tyr Val Leu
            210                 215                 220 atg tac ttc tgt cga gga ggc acg ctg cct tgg cag ggc atc aaa gcg                    838
Met Tyr Phe Cys Arg Gly Gly Thr Leu Pro Trp Gln Gly Ile Lys Ala
225                 230                 235                 240 aat acc aaa cag gag aag tac cac aag atc atg gag aag aag atg tcg                    886
Asn Thr Lys Gln Glu Lys Tyr His Lys Ile Met Glu Lys Lys Met Ser
                245                 250                 255 acg ccc gtc gag gtg cta tgc aag gga tat cca agc gaa ttt gcc aca                    934
Thr Pro Val Glu Val Leu Cys Lys Gly Tyr Pro Ser Glu Phe Ala Thr
            260                 265                 270 tac ttg cac tac tgc cgc tcc ttg cga ttc gag gac cga ccg gac tac                    982
Tyr Leu His Tyr Cys Arg Ser Leu Arg Phe Glu Asp Arg Pro Asp Tyr
            275                 280                 285 gcc tac ctc aag cga ctc ttt cga gat ctc tac atc aaa gag ggc tac                   1030
Ala Tyr Leu Lys Arg Leu Phe Arg Asp Leu Tyr Ile Lys Glu Gly Tyr
290                 295                 300 gat gac agt gac cgc gaa ttc gac tgg aca gtg aaa ctt tcg tcg cgc                   1078
Asp Asp Ser Asp Arg Glu Phe Asp Trp Thr Val Lys Leu Ser Ser Arg
305                 310                 315                 320 agt ctc gga ccg cca agc agt cga gcg caa cat gtt tta ctg agt caa                   1126
Ser Leu Gly Pro Pro Ser Ser Arg Ala Gln His Val Leu Leu Ser Gln
                325                 330                 335 gac acc cga acg cga ggg aag cgg gag aca gat cga cct gtc gct gcg                   1174
Asp Thr Arg Thr Arg Gly Lys Arg Glu Thr Asp Arg Pro Val Ala Ala
            340                 345                 350 cgg agt ggc gac cgc gaa cga gga atc cat ttc agc aac ggg aac gtg                   1222
Arg Ser Gly Asp Arg Glu Arg Gly Ile His Phe Ser Asn Gly Asn Val
            355                 360                 365 ggc aat cct tcg atg gca acg aac ccc ggc ggc ctg tca gtc atg gtg                   1270
Gly Asn Pro Ser Met Ala Thr Asn Pro Gly Gly Leu Ser Val Met Val
370                 375                 380 cat gaa cgc acg agt ctg gtg gat cag gga gac cgt ggg tcg cgc gaa                   1318
His Glu Arg Thr Ser Leu Val Asp Gln Gly Asp Arg Gly Ser Arg Glu
385                 390                 395                 400 act tct acg cgg aaa gaa gac gcg aag gac gga aga tgg cca gga ggc                   1366
Thr Ser Thr Arg Lys Glu Asp Ala Lys Asp Gly Arg Trp Pro Gly Gly
                405                 410                 415 aga ttt tct tgt ctt cca ctg tta tgt cgg cgc tct ccg acg aag gcc                   1414
Arg Phe Ser Cys Leu Pro Leu Leu Cys Arg Arg Ser Pro Thr Lys Ala
            420                 425                 430 tag atgaactgcg gaggcgctcc tgtccccgca gttggcatct ctctccttca                        1467
ttgtcgttgt tccctgcaa ctcgagtcca cccttgacat cctcgtctct ctcttcctgt                  1527
cggtttcctc tttctcgtcc tctcccccct agcttcgttc tctcctttct atcctgcttc                 1587
ggcgtcgcct cacttctctc ctcacttctc tccctttgt ttttcttcgc ggcgtctctc                  1647
cttcactctg tctccgcctc tgacgccgcg cgggagccgt ttcctgcagg cagctcaggc                 1707
aatacctgcc tgcaggtgcc tctccttttt gagcgtctct ctttcctcgt cgaaacggtc                 1767
ctcacagctt cctctccctg gggacgccgt gggcgtaagt tctttttttg acggtcccgg                 1827
tgggctggcg ttgttcgcct gccttccgcg catgcactcc gagcatttt gcctggcctg                  1887
```

```
gacttctccg agcgagagtt gcggtttggc ttctgcatcg tctcctgcgc tgctttcatt    1947
tctctaggtt tctgcttgcg gcctccgtgt acagaaatcg aaggtgaag gcgtagtggc     2007 cagagaacga agcaaacgag agaaccacgt tccaccttgt gcgcacgcat gcatctacgc    2067
atgcacggta tttaagccga ttttttgtgt atgtatatag atgtatatat atatgtatct    2127
acatgtatct acctatatat atgtgtgtgt gtaagtggaa gtgtattttt gcatgtgcag    2187
aaagctttct tttccgctgg catgctggaa gaagggcagg aggcgacgat cctgcgagtc    2247
agggcgttcc cttgtttcca gtgagttaac cgaattgttt attgatatgc gtttgcatgc    2307
atcgacaatg gatcctagac acgcccgttt aaaatcagag gtattcctaa aaaaaaaaaa    2367
aaaaaa                                                                2373
```

<210> SEQ ID NO 6
<211> LENGTH: 432
<212> TYPE: PRT
<213> ORGANISM: Toxoplasma gondii

<400> SEQUENCE: 6

```
Met Ala His His Gln Asp Thr Arg Asn His Thr Gly Val Gly Pro Ser
 1               5                  10                  15

Ser Ser Ile Pro Leu Lys Asp Leu Lys Ile Ala Gly Val Trp Lys Ile
             20                  25                  30

Gly Arg Lys Ile Gly Ser Gly Ser Phe Gly Asp Ile Tyr Lys Gly Leu
         35                  40                  45

Asn Ser Gln Thr Gly Gln Glu Val Ala Leu Lys Val Glu Ser Thr Lys
     50                  55                  60

Ala Lys His Pro Gln Leu Leu Tyr Glu Tyr Lys Leu Leu Lys His Leu
 65                  70                  75                  80

Gln Gly Gly Thr Gly Ile Ala Gln Val Phe Cys Cys Glu Thr Ala Gly
                 85                  90                  95

Asp His Asn Ile Met Ala Met Glu Leu Leu Gly Pro Ser Leu Glu Asp
            100                 105                 110

Val Phe Asn Leu Cys Asn Arg Thr Phe Ser Leu Lys Thr Ile Leu Leu
        115                 120                 125

Leu Ala Asp Gln Phe Leu Gln Arg Val Glu Tyr Ile His Ser Lys Asn
    130                 135                 140

Phe Ile His Arg Asp Ile Lys Pro Asp Asn Phe Leu Leu Gly Gly Ala
145                 150                 155                 160

Gly Asn Gln Asn Thr Ile Tyr Val Ile Asp Phe Gly Leu Ala Lys Lys
                165                 170                 175

Phe Arg Asp Pro Lys Thr His Gln His Ile Pro Tyr Arg Glu Asn Lys
            180                 185                 190

Asn Leu Thr Gly Thr Ala Arg Tyr Ala Ser Ile Ser Ala His Leu Gly
        195                 200                 205

Ser Glu Gln Ser Arg Arg Asp Asp Leu Glu Ala Val Gly Tyr Val Leu
    210                 215                 220

Met Tyr Phe Cys Arg Gly Gly Thr Leu Pro Trp Gln Gly Ile Lys Ala
225                 230                 235                 240

Asn Thr Lys Gln Glu Lys Tyr His Lys Ile Met Glu Lys Lys Met Ser
                245                 250                 255

Thr Pro Val Glu Val Leu Cys Lys Gly Tyr Pro Ser Glu Phe Ala Thr
            260                 265                 270

Tyr Leu His Tyr Cys Arg Ser Leu Arg Phe Glu Asp Arg Pro Asp Tyr
        275                 280                 285
```

```
Ala Tyr Leu Lys Arg Leu Phe Arg Asp Leu Tyr Ile Lys Glu Gly Tyr
    290                 295                 300

Asp Asp Ser Asp Arg Glu Phe Asp Trp Thr Val Lys Leu Ser Ser Arg
305                 310                 315                 320

Ser Leu Gly Pro Pro Ser Ser Arg Ala Gln His Val Leu Leu Ser Gln
                325                 330                 335

Asp Thr Arg Thr Arg Gly Lys Arg Glu Thr Asp Arg Pro Val Ala Ala
            340                 345                 350

Arg Ser Gly Asp Arg Glu Arg Gly Ile His Phe Ser Asn Gly Asn Val
        355                 360                 365

Gly Asn Pro Ser Met Ala Thr Asn Pro Gly Gly Leu Ser Val Met Val
    370                 375                 380

His Glu Arg Thr Ser Leu Val Asp Gln Gly Asp Arg Gly Ser Arg Glu
385                 390                 395                 400

Thr Ser Thr Arg Lys Glu Asp Ala Lys Asp Gly Arg Trp Pro Gly Gly
                405                 410                 415

Arg Phe Ser Cys Leu Pro Leu Leu Cys Arg Arg Ser Pro Thr Lys Ala
            420                 425                 430

<210> SEQ ID NO 7
<211> LENGTH: 543
<212> TYPE: DNA
<213> ORGANISM: Toxoplasma gondii (EST)

<400> SEQUENCE: 7
agaatttcat tcacagagat atcaaaccag ataactttct tctcggcggt gccggcaatc     60
aaaacacgat ctacgtgatc gacttcggcc tggcgaagaa gtttcgcgat ccgaaaacgc    120
accaacatat tccgtacaga gaaaacaaga atctcacggg aacggcgcgc tacgcgtcca    180
tcagtgcgca tctgtgttcc gagcagagtc gccgagatga cctcgaagca gtcggctacg    240
ttctcatgta cttctgtcga ggaggcacgc tgccttggca gggcatcaaa gcgaatacca    300
aacaggagaa gtaccacaag atcatggaga agaagatgtc gacgcccgtc gaggtgctat    360
gcaagggata tccaagcgaa tttgccacat acttgcacta ctgccgctcc ttgcgattcg    420
aggaccgacc ggactacgcc tacctcaagc gactctttcg agatctctac atcaaagagg    480
gctacgatga cagtgaccgc gaattcgact ggacagtgaa ctttcgtcg cgcagtctcg     540 gac                                                                 543

<210> SEQ ID NO 8
<211> LENGTH: 341
<212> TYPE: DNA
<213> ORGANISM: Toxoplasma gondii (EST)

<400> SEQUENCE: 8
gatatccaag cgaatttgcc acatacttgc actactgccg ctccttgcga ttcgaggacc     60
gaccggacta cgcctacctc aagcgactct ttcgagatct ctacatcaaa gagggctacg    120
atgacagtga ccgcgaattc gactggacag tgaaactttc gtcgcgcagt ctcggaccgc    180
caagcagtcg agcgcaacat gttttactga gtcaagacac ccgaacgcga gggaagcggg    240
agacagatcg acctgtcgct gtgcggagtg gcgaccgcga acgaggaatc catttcagca    300
acgggaacgt gggcaatccc tccgatggca acgaacccc g                        341

<210> SEQ ID NO 9
<211> LENGTH: 30
```

```
<212> TYPE: DNA
<213> ORGANISM: Artificial Sequence
<220> FEATURE:
<223> OTHER INFORMATION: oligonucleotide

<400> SEQUENCE: 9
gatatcaaac cagataactt tcttctcggc                                    30

<210> SEQ ID NO 10
<211> LENGTH: 23
<212> TYPE: DNA
<213> ORGANISM: Artificial Sequence
<220> FEATURE:
<223> OTHER INFORMATION: oligonucleotide

<400> SEQUENCE: 10
caaggagcgg cagtagtgca agt                                           23

<210> SEQ ID NO 11
<211> LENGTH: 21
<212> TYPE: PRT
<213> ORGANISM: Eimeria tenella (peptide)

<400> SEQUENCE: 11

Ala Lys Asp Leu Ile Arg Lys Met Leu Ala Tyr Val Pro Ser Met Arg
 1               5                  10                  15

Ile Ser Ala Arg Asp
             20

<210> SEQ ID NO 12
<211> LENGTH: 20
<212> TYPE: PRT
<213> ORGANISM: Eimeria tenella (peptide)

<400> SEQUENCE: 12

Ala Val Lys Val Ile Ser Lys Arg Gln Val Lys Gln Lys Thr Asp Lys
 1               5                  10                  15

Glu Leu Leu Leu
             20

<210> SEQ ID NO 13
<211> LENGTH: 18
<212> TYPE: PRT
<213> ORGANISM: Artificial Sequence
<220> FEATURE:
<223> OTHER INFORMATION: peptide

<400> SEQUENCE: 13

Arg Arg Lys Asp Leu His Asp Asp Glu Glu Asp Glu Ala Met Ser Ile
 1               5                  10                  15

Thr Ala

<210> SEQ ID NO 14
<211> LENGTH: 11
<212> TYPE: PRT
<213> ORGANISM: Artificial Sequence
<220> FEATURE:
<223> OTHER INFORMATION: peptide

<400> SEQUENCE: 14

Arg Arg Ala Asp Asp Ser Asp Asp Asp Asp
 1               5                  10

<210> SEQ ID NO 15
```

```
<211> LENGTH: 15
<212> TYPE: PRT
<213> ORGANISM: Artificial Sequence
<220> FEATURE:
<223> OTHER INFORMATION: peptide

<400> SEQUENCE: 15

Pro Leu Ala Arg Thr Leu Ser Val Ala Gly Leu Pro Gly Lys Lys
1               5                   10                  15

<210> SEQ ID NO 16
<211> LENGTH: 11
<212> TYPE: PRT
<213> ORGANISM: Artificial Sequence
<220> FEATURE:
<223> OTHER INFORMATION: peptide

<400> SEQUENCE: 16

Met His Lys Asn Glu Thr Val Glu Cys Leu Lys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: peptide

<400> SEQUENCE: 17

Asp Asp Asp Glu Glu Ser Ile Thr Arg Arg
1               5                   10

<210> SEQ ID NO 18
<211> LENGTH: 7
<212> TYPE: PRT
<213> ORGANISM: Artificial Sequence
<220> FEATURE:
<223> OTHER INFORMATION: peptide

<400> SEQUENCE: 18

Leu Arg Arg Ala Ser Leu Gly
1               5

<210> SEQ ID NO 19
<211> LENGTH: 14
<212> TYPE: PRT
<213> ORGANISM: Artificial Sequence
<220> FEATURE:
<223> OTHER INFORMATION: peptide

<400> SEQUENCE: 19

Lys Arg Arg Arg Ala Leu Ser Val Ala Ser Leu Pro Gly Leu
1               5                   10

<210> SEQ ID NO 20
<211> LENGTH: 10
<212> TYPE: PRT
<213> ORGANISM: Artificial Sequence
<220> FEATURE:
<223> OTHER INFORMATION: peptide

<400> SEQUENCE: 20

Arg Arg Arg Glu Glu Glu Thr Glu Glu Glu
1               5                   10

<210> SEQ ID NO 21
<211> LENGTH: 324
```

<212> TYPE: PRT
<213> ORGANISM: Plasmodium falciparum

<400> SEQUENCE: 21

```
Met Glu Ile Arg Val Ala Asn Lys Tyr Ala Leu Gly Lys Lys Leu Gly
 1               5                  10                  15

Ser Gly Ser Phe Gly Asp Ile Tyr Val Ala Lys Asp Ile Val Thr Met
             20                  25                  30

Glu Glu Phe Ala Val Lys Leu Glu Ser Thr Arg Ser Lys His Pro Gln
         35                  40                  45

Leu Leu Tyr Glu Ser Lys Leu Tyr Lys Ile Leu Gly Gly Ile Gly
     50                  55                  60

Val Pro Lys Val Tyr Trp Tyr Gly Ile Glu Gly Asp Phe Thr Ile Met
65                  70                  75                  80

Val Leu Asp Leu Leu Gly Pro Ser Leu Glu Asp Leu Phe Thr Leu Cys
                 85                  90                  95

Asn Arg Lys Phe Ser Leu Lys Thr Val Arg Met Thr Ala Asp Gln Met
            100                 105                 110

Leu Asn Arg Ile Glu Tyr Val His Ser Lys Asn Phe Ile His Arg Asp
        115                 120                 125

Ile Lys Pro Asp Asn Phe Leu Ile Gly Arg Gly Lys Lys Val Thr Leu
    130                 135                 140

Ile His Ile Ile Asp Phe Gly Leu Ala Lys Lys Tyr Arg Asp Ser Arg
145                 150                 155                 160

Ser His Thr Ser Tyr Pro Tyr Lys Glu Gly Lys Asn Leu Thr Gly Thr
                165                 170                 175

Ala Arg Tyr Ala Ser Ile Asn Thr His Leu Gly Ile Glu Gln Ser Arg
            180                 185                 190

Arg Asp Asp Ile Glu Ala Leu Gly Tyr Val Leu Met Tyr Phe Leu Arg
        195                 200                 205

Gly Ser Leu Pro Trp Gln Gly Leu Lys Ala Ile Ser Lys Lys Asp Lys
    210                 215                 220

Tyr Asp Lys Ile Met Glu Lys Lys Ile Ser Thr Ser Val Glu Val Leu
225                 230                 235                 240

Cys Arg Asn Ala Ser Phe Glu Phe Val Thr Tyr Leu Asn Tyr Cys Arg
                245                 250                 255

Ser Leu Arg Phe Glu Asp Arg Pro Asp Tyr Thr Tyr Leu Arg Arg Leu
            260                 265                 270

Leu Lys Asp Leu Phe Ile Arg Glu Gly Phe Thr Tyr Asp Phe Leu Phe
        275                 280                 285

Asp Trp Thr Cys Val Tyr Ala Ser Glu Lys Lys Lys Met Leu
    290                 295                 300

Glu Asn Lys Asn Arg Phe Asp Gln Thr Ala Asp Gln Glu Gly Arg Asp
305                 310                 315                 320

Gln Arg Asn Asn
```

<210> SEQ ID NO 22
<211> LENGTH: 353
<212> TYPE: PRT
<213> ORGANISM: Leshmania major

<400> SEQUENCE: 22

```
Met Asn Val Glu Leu Arg Val Gly Asn Arg Tyr Arg Ile Gly Gln Lys
 1               5                  10                  15

Ile Gly Ser Gly Ser Phe Gly Glu Ile Phe Arg Gly Thr Asn Ile Gln
```

```
                20                  25                  30
Thr Gly Asp Pro Val Ala Ile Lys Leu Glu Gln Val Lys Thr Arg His
            35                  40                  45
Pro Gln Leu Thr Tyr Glu Ser Arg Phe Tyr Arg Ile Leu Gly Ser Gly
        50                  55                  60
Gly Gly Ala Val Gly Ile Pro Met Met Phe Tyr His Gly Val Glu Gly
65                  70                  75                  80
Glu Phe Asn Val Met Val Ile Glu Leu Leu Gly Pro Ser Leu Glu Asp
                85                  90                  95
Leu Phe Ser Phe Cys Gly Arg Arg Leu Ser Leu Lys Thr Thr Leu Met
            100                 105                 110
Leu Ala Asp Gln Met Ile Ser Arg Ile Glu Phe Val His Ser Lys Ser
        115                 120                 125
Val Leu His Arg Asp Ile Lys Pro Asp Asn Phe Leu Met Gly Thr Gly
    130                 135                 140
Lys Lys Gly His His Val Tyr Ile Ile Asp Phe Gly Leu Ala Lys Lys
145                 150                 155                 160
Tyr Arg Asp Pro Arg Thr His Ala His Ile Pro Tyr Lys Glu Gly Lys
                165                 170                 175
Ser Leu Thr Gly Thr Ala Arg Tyr Cys Ser Ile Asn Thr His Met Gly
            180                 185                 190
Val Glu Gln Gly Arg Arg Asp Asp Met Glu Gly Ile Gly Tyr Ile Leu
        195                 200                 205
Met Tyr Phe Leu Arg Gly Ser Leu Pro Trp Gln Gly Leu Lys Ala His
    210                 215                 220
Thr Lys Gln Glu Lys Tyr Asn Arg Ile Ser Glu Arg Lys Gln Thr Thr
225                 230                 235                 240
Pro Val Glu Leu Leu Cys Lys Gly Phe Pro Ser Glu Phe Ala Ala Tyr
                245                 250                 255
Met Asn Tyr Val Arg Ala Leu Arg Phe Glu Asp Lys Pro Asp Tyr Ser
            260                 265                 270
Tyr Leu Lys Arg Met Phe Arg Asp Leu Phe Val Arg Glu Gly Tyr His
        275                 280                 285
Val Asp Tyr Val Phe Asp Trp Thr Leu Lys Arg Ile His Glu Ser Leu
    290                 295                 300
Gln Glu Gln Gln Ser Phe Pro Gly Gly Ser Asn Gly Gly Gly Ala Ala
305                 310                 315                 320
Gly Asn Gly Ser Pro Val Asn Gln Ser Pro Ala Gln Gly Gly Asn Gly
                325                 330                 335
Gly Ala Pro Asn Ser Ala Asn Asn Gln Glu Ser Gly Ala Pro Glu Gln
            340                 345                 350
Gln

<210> SEQ ID NO 23
<211> LENGTH: 330
<212> TYPE: PRT
<213> ORGANISM: Trypanosoma cruzi

<400> SEQUENCE: 23

Met Ser Leu Glu Leu Arg Val Gly Asn Arg Phe Arg Leu Gly Gln Lys
1               5                   10                  15
Ile Gly Ala Gly Ser Phe Gly Glu Ile Phe Arg Gly Thr Asn Ile Gln
            20                  25                  30
Thr Gly Glu Thr Val Ala Ile Lys Leu Glu Gln Ala Lys Thr Arg His
```

-continued

```
            35                  40                  45
Pro Gln Leu Ala Leu Glu Ala Arg Phe Tyr Arg Ile Leu Asn Ala Gly
    50                  55                  60
Gly Gly Val Val Gly Ile Pro Asn Ile Leu Phe Tyr Gly Val Glu Gly
65                  70                  75                  80
Glu Phe Asn Val Met Val Met Asp Leu Leu Gly Pro Ser Leu Glu Asp
                85                  90                  95
Leu Phe Ser Phe Cys Asp Arg Lys Leu Ser Leu Lys Thr Thr Leu Met
            100                 105                 110
Leu Ala Glu Gln Met Ile Ala Arg Ile Glu Phe Val His Ser Lys Ser
        115                 120                 125
Val Ile His Arg Asp Met Lys Pro Asp Asn Phe Leu Met Gly Thr Gly
    130                 135                 140
Lys Lys Gly His His Val Tyr Val Val Asp Phe Gly Leu Ala Lys Lys
145                 150                 155                 160
Tyr Arg Asp Pro Arg Thr His Gln His Ile Pro Tyr Lys Glu Gly Lys
                165                 170                 175
Ser Leu Thr Gly Thr Ala Arg Tyr Cys Ser Ile Asn Thr His Leu Gly
            180                 185                 190
Ile Glu Gln Ser Arg Arg Asp Asp Leu Glu Gly Ile Gly Tyr Ile Leu
        195                 200                 205
Met Tyr Phe Leu Arg Gly Ser Leu Pro Trp Gln Gly Leu Lys Ala His
    210                 215                 220
Thr Lys Gln Glu Lys Tyr Ser Arg Ile Ser Glu Arg Lys Gln Thr Thr
225                 230                 235                 240
Pro Val Glu Thr Leu Cys Lys Gly Phe Pro Ala Glu Phe Ala Ala Tyr
                245                 250                 255
Leu Asn Tyr Ile Arg Ser Leu Arg Phe Glu Asp Lys Pro Asp Tyr Ser
            260                 265                 270
Tyr Leu Lys Arg Leu Phe Arg Glu Leu Phe Ile Arg Glu Gly Tyr His
        275                 280                 285
Val Asp Tyr Val Phe Asp Trp Thr Leu Lys Arg Ile His Glu Asn Leu
    290                 295                 300
Lys Ala Glu Gly Ser Gly Gln Gln Glu Gln Lys Gln Gln Gln Gln Gln
305                 310                 315                 320
Gln Arg Glu Arg Gly Asp Val Glu Gln Ala
                325                 330
```

<210> SEQ ID NO 24
<211> LENGTH: 55
<212> TYPE: DNA
<213> ORGANISM: Artificial Sequence
<220> FEATURE:
<223> OTHER INFORMATION: oligonucleotide

<400> SEQUENCE: 24
atggactaca aagacgatga cgacaaggag gtcagggtcg gaggcaagta ccgac        55

<210> SEQ ID NO 25
<211> LENGTH: 34
<212> TYPE: DNA
<213> ORGANISM: Artificial Sequence
<220> FEATURE:
<223> OTHER INFORMATION: oligonucleotide

<400> SEQUENCE: 25
cggtctagat cagagggaga cgcgcgtcct gacc        34

<210> SEQ ID NO 26
<211> LENGTH: 51
<212> TYPE: DNA
<213> ORGANISM: Artificial Sequence
<220> FEATURE:
<223> OTHER INFORMATION: oligonucleotide

<400> SEQUENCE: 26
atggactaca aagacgatga cgacaaggcg caccatcaag acacccgcaa c        51

<210> SEQ ID NO 27
<211> LENGTH: 37
<212> TYPE: DNA
<213> ORGANISM: Artificial Sequence
<220> FEATURE:
<223> OTHER INFORMATION: oligonucleotide

<400> SEQUENCE: 27
cggtctagat caaaaaaaga acttacgccc acggcgt                         37

<210> SEQ ID NO 28
<211> LENGTH: 68
<212> TYPE: DNA
<213> ORGANISM: Artificial Sequence
<220> FEATURE:
<223> OTHER INFORMATION: oligonucleotide

<400> SEQUENCE: 28
ggcggatccg aaaatggact acaaagacga tgacgacaag gaggtcaggg tcggaggcaa    60
gtaccgac                                                             68

<210> SEQ ID NO 29
<211> LENGTH: 64
<212> TYPE: DNA
<213> ORGANISM: Artificial Sequence
<220> FEATURE:
<223> OTHER INFORMATION: oligonucleotide

<400> SEQUENCE: 29
ggcgtgatca aaaatggact acaaagacga tgacgacaag gcgcaccatc aagacacccg    60
caac                                                                 64

<210> SEQ ID NO 30
<211> LENGTH: 41
<212> TYPE: DNA
<213> ORGANISM: Artificial Sequence
<220> FEATURE:
<223> OTHER INFORMATION: oligonucleotide

<400> SEQUENCE: 30
ggcctcgagg gccttcgtcg gagagcgccg acataacagt g                    41

<210> SEQ ID NO 31
<211> LENGTH: 39
<212> TYPE: DNA
<213> ORGANISM: Artificial Sequence
<220> FEATURE:
<223> OTHER INFORMATION: oligonucleotide

<400> SEQUENCE: 31
ggcgtcgacg atgttatggt cgcccgcagt ctcgcaaca                       39

<210> SEQ ID NO 32

-continued

<210> SEQ ID NO 32
<211> LENGTH: 50
<212> TYPE: DNA
<213> ORGANISM: Artificial Sequence
<220> FEATURE:
<223> OTHER INFORMATION: oligonucleotide

<400> SEQUENCE: 32
ggcgtcgacg atcttgtggt acttctcctg tttggtattc gctttgatgc    50

<210> SEQ ID NO 33
<211> LENGTH: 41
<212> TYPE: DNA
<213> ORGANISM: Artificial Sequence
<220> FEATURE:
<223> OTHER INFORMATION: oligonucleotide

<400> SEQUENCE: 33
ggcctcgagc acgttcccgt tgctgaaatg gattcctcgt t    41

<210> SEQ ID NO 34
<211> LENGTH: 57
<212> TYPE: DNA
<213> ORGANISM: Artificial Sequence
<220> FEATURE:
<223> OTHER INFORMATION: oligonucleotide

<400> SEQUENCE: 34
atggactaca aagacgatga cgacaaggac gtccgtgtgg ggggtaagta tcgtttg    57

<210> SEQ ID NO 35
<211> LENGTH: 40
<212> TYPE: DNA
<213> ORGANISM: Artificial Sequence
<220> FEATURE:
<223> OTHER INFORMATION: oligonucleotide

<400> SEQUENCE: 35
cggtctagat cacggttcta actgaggcaa ccgtccaagt    40

<210> SEQ ID NO 36
<211> LENGTH: 70
<212> TYPE: DNA
<213> ORGANISM: Artificial Sequence
<220> FEATURE:
<223> OTHER INFORMATION: oligonucleotide

<400> SEQUENCE: 36
ggcagatctg aaaatggact acaaagacga tgacgacaag gacgtccgtg tgggggtaa    60 gtatcgtttg    70

<210> SEQ ID NO 37
<211> LENGTH: 11
<212> TYPE: PRT
<213> ORGANISM: Eimeria tenella (peptide)

<400> SEQUENCE: 37

Ser Arg His Pro Gln Leu Ile Tyr Glu Ser Lys
 1               5                  10

<210> SEQ ID NO 38
<211> LENGTH: 12
<212> TYPE: PRT
<213> ORGANISM: Eimeria tenella (peptide)

<400> SEQUENCE: 38

-continued

Thr Val Leu Met Leu Ala Asp Gln Met Leu Asn Arg
 1               5                  10

<210> SEQ ID NO 39
<211> LENGTH: 11
<212> TYPE: PRT
<213> ORGANISM: Eimeria tenella (peptide)

<400> SEQUENCE: 39

Asp Ile Lys Pro Asp Asn Phe Leu Ile Gly Arg
 1               5                  10

<210> SEQ ID NO 40
<211> LENGTH: 8
<212> TYPE: PRT
<213> ORGANISM: Eimeria tenella (peptide)

<400> SEQUENCE: 40

Thr Gln Ser His Ile Pro Tyr Arg
 1               5

<210> SEQ ID NO 41
<211> LENGTH: 14
<212> TYPE: PRT
<213> ORGANISM: Eimeria tenella (peptide)

<400> SEQUENCE: 41

Tyr Ala Ser Val Asn Thr His Leu Gly Ile Glu Gln Ser Arg
 1               5                  10

<210> SEQ ID NO 42
<211> LENGTH: 11
<212> TYPE: PRT
<213> ORGANISM: Eimeria tenella (peptide)

<400> SEQUENCE: 42

Phe Glu Asp Arg Pro Asp Tyr Ser Tyr Leu Arg
 1               5                  10

<210> SEQ ID NO 43
<211> LENGTH: 5
<212> TYPE: PRT
<213> ORGANISM: Eimeria tenella (peptide)

<400> SEQUENCE: 43

Asp Leu Phe Phe Arg
 1               5

<210> SEQ ID NO 44
<211> LENGTH: 30
<212> TYPE: DNA
<213> ORGANISM: Artificial Sequence
<220> FEATURE:
<223> OTHER INFORMATION: oligonucleotide

<400> SEQUENCE: 44
aaaatggggc agcaggaaag cactcttggg                                    30

<210> SEQ ID NO 45
<211> LENGTH: 29
<212> TYPE: DNA
<213> ORGANISM: Artificial Sequence
<220> FEATURE:
<223> OTHER INFORMATION: oligonucleotide -continued

```
<400> SEQUENCE: 45
gtttccgcag agcttcaaga gcatctgtt                                          29
```